(12) United States Patent
Tyler

(10) Patent No.: US 11,707,636 B2
(45) Date of Patent: *Jul. 25, 2023

(54) METHODS AND DEVICES FOR MODULATING CELLULAR ACTIVITY USING ULTRASOUND

(71) Applicant: Arizona Board of Regents on Behalf of Arizona State University, Scottsdale, AZ (US)

(72) Inventor: William James P. Tyler, Cave Creek, AZ (US)

(73) Assignee: Arizona Board of Regents on Behalf of Arizona State University, Scottsdale, AZ (US)

(*) Notice: Subject to any disclaimer, the term of this patent is extended or adjusted under 35 U.S.C. 154(b) by 489 days.

This patent is subject to a terminal disclaimer.

(21) Appl. No.: 16/779,442

(22) Filed: Jan. 31, 2020

(65) Prior Publication Data

US 2020/0246641 A1     Aug. 6, 2020

Related U.S. Application Data

(63) Continuation of application No. 15/192,749, filed on Jun. 24, 2016, now Pat. No. 10,556,132, which is a
(Continued)

(51) Int. Cl.
*A61N 7/00*     (2006.01)
*A61B 5/00*     (2006.01)
(Continued)

(52) U.S. Cl.
CPC .............. *A61N 7/00* (2013.01); *A61B 5/0036* (2018.08); *A61B 5/369* (2021.01); *A61B 5/4836* (2013.01);
(Continued)

(58) Field of Classification Search
CPC ........ A61N 7/00; A61N 5/062; A61N 5/0622; A61N 5/0613; A61N 5/067;
(Continued)

(56) References Cited

U.S. PATENT DOCUMENTS 3,762,396 A  10/1973 Ballentine et al.
4,002,221 A   1/1977 Buchalter
(Continued)

FOREIGN PATENT DOCUMENTS

CN    1096703 A    12/1994
CN    1507333 A     6/2004
(Continued)

OTHER PUBLICATIONS

Additional figures for cog enhancement NPA. Jan. 1, 2013.
(Continued)

*Primary Examiner* — Sanjay Cattungal
(74) *Attorney, Agent, or Firm* — Shay Glenn LLP

(57) ABSTRACT

The present invention comprises methods and devices for modulating the activity or activities of living cells, such as cells found in or derived from humans, animals, plants, insects, microorganisms and other organisms. Methods of the present invention comprise use of the application of ultrasound, such as low intensity, low frequency ultrasound, to living cells to affect the cells and modulate the cells' activities. Devices of the present invention comprise one or more components for generating ultrasound waves, such as ultrasonic emitters, transducers or piezoelectric transducers, composite transducers, CMUTs, and which may be provided as single or multiple transducers or in an array configurations. The ultrasound waves may be of any shape, and may be focused or unfocused.

20 Claims, 20 Drawing Sheets

Related U.S. Application Data continuation of application No. 14/460,007, filed on Aug. 14, 2014, now Pat. No. 9,403,038, which is a continuation of application No. 14/025,586, filed on Sep. 12, 2013, now Pat. No. 8,858,440, which is a continuation of application No. 13/003,853, filed as application No. PCT/US2009/050560 on Jul. 14, 2009, now Pat. No. 8,591,419.

(60) Provisional application No. 61/175,413, filed on May 4, 2009, provisional application No. 61/080,666, filed on Jul. 14, 2008.

(51) Int. Cl.
| | | |
|---|---|---|
| *A61B 5/369* | (2021.01) | |
| *A61N 5/06* | (2006.01) | |
| *C12N 5/0793* | (2010.01) | |
| *C12N 13/00* | (2006.01) | |
| *A61N 5/067* | (2006.01) | |

(52) U.S. Cl.
CPC ............ *A61N 5/062* (2013.01); *A61N 5/0622* (2013.01); *C12N 5/0619* (2013.01); *C12N 13/00* (2013.01); *A61N 5/067* (2021.08); *A61N 5/0613* (2013.01); *A61N 2005/0651* (2013.01); *A61N 2005/0652* (2013.01); *A61N 2005/0653* (2013.01); *A61N 2007/0021* (2013.01); *A61N 2007/0026* (2013.01); *A61N 2007/0073* (2013.01); *A61N 2007/0078* (2013.01)

(58) Field of Classification Search
CPC .... A61N 2005/0651; A61N 2005/0652; A61N 2005/0653; A61N 2007/0021; A61N 2007/0026; A61N 2007/0073; A61N 2007/0078; A61B 5/0036; A61B 5/369; A61B 5/4836; C12N 5/0619; C12N 13/00
See application file for complete search history.

(56) References Cited

U.S. PATENT DOCUMENTS

| | | | |
|---|---|---|---|
| 4,059,098 | A | 11/1977 | Murdock |
| 4,309,575 | A | 1/1982 | Zweig et al. |
| 4,556,066 | A | 12/1985 | Semrow |
| 4,646,744 | A | 3/1987 | Capel |
| 4,723,552 | A | 2/1988 | Kenyon et al. |
| 4,886,068 | A | 12/1989 | Kaneko et al. |
| 5,103,129 | A | 4/1992 | Slayton et al. |
| 5,127,410 | A | 7/1992 | King et al. |
| 5,342,410 | A | 8/1994 | Braverman |
| 5,394,877 | A | 3/1995 | Orr et al. |
| 5,413,550 | A | 5/1995 | Castel |
| 5,476,438 | A | 12/1995 | Rich et al. |
| 5,494,038 | A | 2/1996 | Wang et al. |
| 5,505,205 | A | 4/1996 | Solomon et al. |
| 5,520,612 | A | 5/1996 | Winder et al. |
| 5,522,878 | A | 6/1996 | Montecalvo et al. |
| 5,540,736 | A | 7/1996 | Haimovich et al. |
| 5,558,092 | A | 9/1996 | Unger et al. |
| 5,752,924 | A | 5/1998 | Kaufman et al. |
| 5,782,767 | A | 7/1998 | Pretlow |
| 5,951,476 | A | 9/1999 | Beach |
| 6,039,694 | A | 3/2000 | Larson et al. |
| 6,078,838 | A | 6/2000 | Rubinstein |
| 6,182,341 | B1 | 2/2001 | Talbot |
| 6,328,694 | B1 | 12/2001 | Michaeli |
| 6,394,969 | B1 | 5/2002 | Lenhardt |
| 6,432,069 | B1 | 8/2002 | Godo et al. |
| 6,478,754 | B1 | 11/2002 | Babaev |
| 6,526,318 | B1 | 2/2003 | Ansarinia |
| 6,536,440 | B1 | 3/2003 | Dawson |
| 6,575,922 | B1 | 6/2003 | Fearnside et al. |
| 6,584,357 | B1 | 6/2003 | Dawson |
| 6,733,450 | B1 | 5/2004 | Alexandrov et al. |
| 6,735,475 | B1 | 5/2004 | Whitehurst et al. |
| 6,770,031 | B2 | 8/2004 | Hynynen et al. |
| 6,846,290 | B2 | 1/2005 | Lizzi et al. |
| 6,964,684 | B2 | 11/2005 | Ortiz et al. |
| 6,978,179 | B1 | 12/2005 | Flagg et al. |
| 7,104,947 | B2 | 9/2006 | Riehl |
| 7,108,663 | B2 | 9/2006 | Talish et al. |
| 7,190,998 | B2 | 3/2007 | Shalev et al. |
| 7,283,861 | B2 | 10/2007 | Bystritsky |
| 7,350,522 | B2 | 4/2008 | Dawson |
| 7,363,076 | B2 | 4/2008 | Yun et al. |
| 7,410,469 | B1 | 8/2008 | Talish et al. |
| 7,429,248 | B1 | 9/2008 | Winder et al. |
| 7,431,704 | B2 | 10/2008 | Babaev |
| 7,510,536 | B2 | 3/2009 | Foley et al. |
| 7,532,935 | B2 | 5/2009 | Maschino et al. |
| 7,699,768 | B2 | 4/2010 | Kishawi et al. |
| 7,699,778 | B2 | 4/2010 | Adam |
| 7,713,218 | B2 | 5/2010 | Babaev et al. |
| 7,914,470 | B2 | 3/2011 | Babaev |
| 7,938,780 | B2 * | 5/2011 | Ragauskas ........... A61B 8/4227 600/459 |
| 7,974,845 | B2 | 7/2011 | Spiridigliozzi et al. |
| 8,123,707 | B2 | 2/2012 | Huckle et al. |
| 8,150,537 | B2 | 4/2012 | Tanaka et al. |
| 8,190,248 | B2 | 5/2012 | Besio et al. |
| 8,235,919 | B2 | 8/2012 | Babaev |
| 8,239,030 | B1 | 8/2012 | Hagedorn et al. |
| 8,591,419 | B2 | 11/2013 | Tyler et al. |
| 8,858,440 | B2 | 10/2014 | Tyler et al. |
| 9,042,201 | B2 | 5/2015 | Tyler et al. |
| 9,403,038 | B2 | 8/2016 | Tyler |
| 10,556,132 | B2 | 2/2020 | Tyler |
| 2001/0040214 | A1 | 11/2001 | Friedman et al. |
| 2002/0042574 | A1 | 4/2002 | Manor et al. |
| 2002/0198577 | A1 | 12/2002 | Jaillet |
| 2003/0009153 | A1 | 1/2003 | Brisken et al. |
| 2003/0032900 | A1 | 2/2003 | Ella |
| 2003/0060711 | A1 | 3/2003 | Michaeli |
| 2003/0199944 | A1 | 10/2003 | Chapin et al. |
| 2004/0049134 | A1 | 3/2004 | Tosaya et al. |
| 2004/0059241 | A1 | 3/2004 | Suffin |
| 2004/0082857 | A1 | 4/2004 | Schonenberger et al. |
| 2004/0143390 | A1 | 7/2004 | Rogers |
| 2004/0249416 | A1 | 12/2004 | Yun et al. |
| 2004/0254443 | A1 | 12/2004 | Gott et al. |
| 2004/0254469 | A1 | 12/2004 | Shkarlet et al. |
| 2005/0020918 | A1 | 1/2005 | Wilk et al. |
| 2005/0020945 | A1 | 1/2005 | Tosaya et al. |
| 2005/0033140 | A1 | 2/2005 | de la Rosa et al. |
| 2005/0085748 | A1 | 4/2005 | Culp et al. |
| 2005/0195103 | A1 | 9/2005 | Davis et al. |
| 2005/0249667 | A1 | 11/2005 | Tuszynski et al. |
| 2005/0277824 | A1 | 12/2005 | Aubry et al. |
| 2006/0058678 | A1 | 3/2006 | Vitek et al. |
| 2006/0074355 | A1 | 4/2006 | Slayton et al. |
| 2006/0111754 | A1 | 5/2006 | Rezai et al. |
| 2006/0163964 | A1 | 7/2006 | Kojima et al. |
| 2006/0173321 | A1 | 8/2006 | Kubota et al. |
| 2006/0173509 | A1 | 8/2006 | Lee et al. |
| 2006/0184070 | A1 | 8/2006 | Hansmann et al. |
| 2006/0201090 | A1 | 9/2006 | Guevara et al. |
| 2006/0273509 | A1 | 12/2006 | Davis et al. |
| 2007/0016041 | A1 | 1/2007 | Nita |
| 2007/0038100 | A1 | 2/2007 | Nita |
| 2007/0043401 | A1 | 2/2007 | John |
| 2007/0093702 | A1 | 4/2007 | Yu et al. |
| 2007/0173902 | A1 | 7/2007 | Maschino |
| 2007/0179557 | A1 | 8/2007 | Maschino |
| 2007/0179570 | A1 | 8/2007 | De Taboada et al. |
| 2007/0299370 | A1 | 12/2007 | Bystritsky |
| 2008/0033297 | A1 | 2/2008 | Sliwa |
| 2008/0045882 | A1 | 2/2008 | Finsterwald |
| 2008/0154332 | A1 | 6/2008 | Rezai |
| 2008/0194967 | A1 | 8/2008 | Sliwa et al. |
| 2008/0200810 | A1 | 8/2008 | Buchalter |
| 2008/0319376 | A1 | 12/2008 | Wilcox et al. |

(56) References Cited

U.S. PATENT DOCUMENTS

| | | |
|---|---|---|
| 2009/0012577 A1 | 1/2009 | Rezai et al. |
| 2009/0024189 A1 | 1/2009 | Lee et al. |
| 2009/0099482 A1 | 4/2009 | Furuhata et al. |
| 2009/0099483 A1 | 4/2009 | Rybyanets |
| 2009/0105581 A1 | 4/2009 | Widenhorn |
| 2009/0112133 A1 | 4/2009 | Deisseroth et al. |
| 2009/0112278 A1 | 4/2009 | Wingeier et al. |
| 2009/0114849 A1 | 5/2009 | Schneider et al. |
| 2009/0149782 A1 | 6/2009 | Cohen |
| 2009/0163964 A1 | 6/2009 | Boyden et al. |
| 2009/0221902 A1 | 9/2009 | Myhr |
| 2009/0222059 A1 | 9/2009 | Hillis et al. |
| 2009/0276005 A1 | 11/2009 | Pless |
| 2010/0016707 A1 | 1/2010 | Amara et al. |
| 2010/0022889 A1 | 1/2010 | Caberg et al. |
| 2010/0030299 A1 | 2/2010 | Covalin |
| 2010/0087698 A1 | 4/2010 | Hoffman |
| 2010/0125207 A1 | 5/2010 | Kim et al. |
| 2010/0125312 A1 | 5/2010 | Stevenson et al. |
| 2010/0145215 A1 | 6/2010 | Pradeep et al. |
| 2010/0324440 A1 | 12/2010 | Moore et al. |
| 2011/0009734 A1 | 1/2011 | Foley et al. |
| 2011/0040171 A1 | 2/2011 | Foley et al. |
| 2011/0040190 A1 | 2/2011 | Jahnke et al. |
| 2011/0082326 A1 | 4/2011 | Mishelevich et al. |
| 2011/0092800 A1 | 4/2011 | Yoo et al. |
| 2011/0112394 A1 | 5/2011 | Mishelevich |
| 2011/0130615 A1 | 6/2011 | Mishelevich |
| 2011/0144716 A1 | 6/2011 | Bikson et al. |
| 2011/0178442 A1 | 7/2011 | Mishelevich |
| 2011/0190668 A1 | 8/2011 | Mishelevich |
| 2011/0196267 A1 | 8/2011 | Mishelevich |
| 2011/0208094 A1 | 8/2011 | Mishelevich |
| 2011/0213200 A1 | 9/2011 | Mishelevich |
| 2011/0270138 A1 | 11/2011 | Mishelevich |
| 2011/0288610 A1 | 11/2011 | Brocke |
| 2012/0029393 A1 | 2/2012 | Lee |
| 2012/0053391 A1 | 3/2012 | Mishelevich |
| 2012/0083719 A1 | 4/2012 | Mishelevich |
| 2012/0197163 A1 | 8/2012 | Mishelevich |
| 2012/0209346 A1 | 8/2012 | Bikson et al. |
| 2012/0245653 A1 | 9/2012 | Bikson et al. |
| 2012/0265261 A1 | 10/2012 | Bikson et al. |
| 2012/0283502 A1 | 11/2012 | Mishelevich et al. |
| 2012/0289869 A1 | 11/2012 | Tyler |
| 2013/0066239 A1 | 3/2013 | Mishelevich |
| 2013/0066350 A1 | 3/2013 | Mishelevich |
| 2013/0079682 A1 | 3/2013 | Mischelevich |
| 2013/0144192 A1 | 6/2013 | Mischelevich et al. |
| 2013/0178765 A1 | 7/2013 | Mishelevich |
| 2013/0184728 A1 | 7/2013 | Mishelevich |
| 2014/0194726 A1 | 7/2014 | Mishelevich et al. |
| 2015/0135840 A1 | 5/2015 | Sato et al. |
| 2015/0151142 A1 | 6/2015 | Tyler et al. |
| 2015/0174418 A1 | 6/2015 | Tyler et al. |
| 2016/0220850 A1 | 8/2016 | Tyler |
| 2019/0105517 A1 | 4/2019 | Tyler |
| 2020/0107725 A1 | 4/2020 | Tyler |

FOREIGN PATENT DOCUMENTS

| | | |
|---|---|---|
| CN | 201098346 Y | 8/2008 |
| CN | 101288600 A | 10/2008 |
| CN | 101500644 A | 8/2009 |
| JP | 62035906 U | 3/1987 |
| JP | H11-290386 A | 10/1999 |
| JP | 2000040191 A | 2/2000 |
| JP | 2001327495 A | 11/2001 |
| JP | 2002000613 A | 1/2002 |
| JP | 2006192181 A | 7/2006 |
| JP | 2006195872 A | 7/2006 |
| JP | 2007517534 A | 7/2007 |
| WO | WO94/006380 A1 | 3/1994 |
| WO | WO98/007367 A1 | 2/1998 |
| WO | WO2007/130308 A2 | 11/2007 |
| WO | WO2008/017998 A2 | 2/2008 |
| WO | WO2008/089003 A2 | 7/2008 |
| WO | WO2009/017264 A1 | 2/2009 |
| WO | WO2009/117323 A2 | 9/2009 |
| WO | WO2013/059833 A1 | 4/2013 |
| WO | WO2018/227088 A1 | 12/2018 |
| WO | WO2019/046757 A1 | 3/2019 |

OTHER PUBLICATIONS

Abbott; Microscopic marvels: The glorious resolution; Nature, vol. 459; pp. 638-639 <DOI:10.1038/459638a>; Jun. 2009.

Andrews; Neuroprotection Trek'The Next Generation: Neuromodulation I. Techniques' Deep Brain Stimulation, Vagus Nerve Stimulation, and Transcranial Magnetic Stimulation; Annals of the New York Academy of Sciences; 993(1); pp. 1-13 <DOI:10.1111/j.1749-6632.2003.tb07506.x>; May 2003.

Arroyo et al.; Mirth, laughter and gelastic seizures; Brain; 116(4); pp. 757-780; Aug. 1, 1993.

Ayling et al.; Automated light-based mapping of motor cortex by photoactivation of channelrhodopsin-2 transgenic mice; Nature Methods; vol. 6; pp. 219-224 <D01:10.1038/nmeth.1303>; Mar. 2009.

Bachtold et al.; Focused ultrasound modifications of neural circuit activity in a mammalian brain; Ultrasound in Medicine and Biology; 24(4); pp. 557-565; May 1, 1998.

Barker; An introduction to the basic principles of magnetic nerve stimulation; Journal of Clinical Neurophysiology; 8(1); pp. 26-37; Jan. 1991.

Bartsch et al.; Stimulation ofthe greater occipital nerve induces increased central excitability of dural afferent input; Brain; 125(7); pp. 1496-1509; Jul. 1, 2002.

Baker et al.; Deep brain stimulation for obsessive-compulsive disorder: using functional magnetic resonance imaging and electrophysiological techniques: technical case report; Neurosurgery; 10 pages; 61(Suppl2); ONSE367-368; Nov. 1, 2007.

Boddaert et al.; Autism: functional brain mapping of exceptional calendar capacity; The British Journal of Psychiatry; 187(1); pp. 83-86; Jul. 1, 2005.

Bragin et al.; Gamma (40-100 Hz) oscillation in the hippocampus of the behaving rat; The Journal of Neuroscience; vol. 15, No. 15, No. 1. pp. 47-60; <DOE:10.1523/JNEUROSCI.15-01-00047.1995>; Jan. 1995.

Bragin et al.; Termination of Epileptic Afterdischarge in the Hippocampus; The Journal of Neuroscience; 17(7); pp. 2567-2579 <DOI:10.1523/JNEUROSCI.17-07-02567.1997>; Apr. 1997.

Breneman et al.; Piezo- and Flexoelectric Membrane Materials Underlie Fast Biological Motors in the Ear; Mater Res Soc Symp Proc; 1186E doi:10.1557/PROC-1186-JJ06-04; (Author Manuscript) Spring 2009.

Burns et al.; Treatment of medically intractable cluster headache by occipital nerve stimulation: long-term follow-up of eight patients; Lancet; 369(9567); pp. 1099-1106; Mar. 31, 2007.

Bystritsky et al.; A review of low-intensity focused ultrasound pulsation; Brain Stimulation: Basic, Translational, and Clinical Research in Neuromodulation; 4(3); pp. 125-136; Jul. 1, 2011.

Buzsáki; Two-stage model of memory trace formation: A role for fnoisyf brain states; Neuroscience; 31(3); pp. 551-570 <DOI:10.1016/0306-4522(89)90423-5>; Jan. 1989.

Buzsáki et al.; High-frequency network oscillation in the hippocampus; Science; 256(5059); pp. 1025-1027 <DOI:10.1126/science.1589772>; May 1992.

Buzsáki; The Hippocampo-Neocortical Dialogue, Cerebral Cortex, 6(2); pp. 81-92 <DOI:10.1093/cercor/6.2.81>; Mar.-Apr. 1996.

Clarke et al.; Transcranial magnetic stimulation for migraine: clinical effects; Journal of Headache and Pain; 7(5); pp. 341-346; Oct. 1, 2006.

Clement et al.; A non-invasive method for focusing ultrasound through the human skull; Physics in Medicine and Biology; 47(8); pp. 1219-1236; Apr. 5, 2002.

clinical trials.gov; Deep brain stimulation (DBS) for treatment resistant bipolar disorder (DBS-BIPO); Oct. 2012; 4 pages; retreived

(56) References Cited

OTHER PUBLICATIONS from the internet ( https://web.archive.org/web/20121214183548/https://clinicaltrials.gov/ct2/show/NCT01372722); on Dec. 17, 2012.
Cooper et al.; A Probe Technique for Determining the Thermal Conductivity of Tissue; Journal of Heat Transfer; 94(2); pp. 133-140 <DOI:10.1115/1.3449883>; May 1972.
Dalecki; Mechanical bioeffects of ultrasound; Annu Rev Biomed Eng.: 6; pp. 229-248; Aug. 15, 2004.
Dinno et al.; The significance of membrane changes in the safe and effective use of therapeutic and diagnostic ultrasound; Physics in Medicine and Biology; 34(11); pp. 1543-1552 <DOI:10.1088/0031-9155/34/11/003>; Nov. 1989.
Dmochowski et al.; Optimized multi-electrode stimulation increases focality and intensity at target; Journal of Neural Engineering; 8(4); 16 pages; doi:10.1088/1741-2560/8/4/046011; Jun. 10, 2011.
Farrell et al.; Study of the human visual cortex: direct cortical evoked potentials and stimulation; Journal of Clinical Neurophysiology; 24(1); pp. 1-10; Feb. 1, 2007.
Feurra, et al. Frequency specific modulation of human somatosensory cortex. Frontiers in Psychology; 6 pages; doi: 10.3389/fpsyg.2011.00013; Feb. 2, 2011.
Fleury et al.; New piezocomposite transducers for therapeutic ultrasound; 2nd International Symposium on Therapeutic Ultrasound ,Seattle, 31/07; 4 pages; Feb. 8, 2002.
Fry et al.; Production of reversible changes in the central nervous system by ultrasound; Science; 127(3289); pp. 83-84; (Author Manuscript); Jan. 10, 1958.
Gavrilov et al.; Application of focused ultrasound for the stimulation of neural structures; Ultrasound in Medicine and Biology; 22(2); pp. 179-192; Jan. 1, 1996.
Gavrilov et al.; The effect of focused ultrasound on the skin and deep nerve structures of man and animal; In Progress in Brain research; 43; pp. 279-292; Jan. 1, 1976.
George et al. Daily repetitive transcranial magnetic stimulation (rTMS) improves mood in depression; Neuroreport; 6(14); pp. 1853-1856; Oct. 2, 1995.
George et al.; Changes in mood and hormone levels after rapid-rate transcranial magnetic stimulation (rTMS) of the prefrontal cortex; The Journal of Neuropsychiatry and Clinical Neurosciencoes; 8(2); pp. 172-180: Spring 1996.
George et al.; Vagus nerve stimulation: a new tool for brain research and therapy; Biological Psychiatry; 47(4); pp. 287-295; Feb. 15, 2000.
Ghanam et al.; Vagal nerve stimulator implantation: an otolaryngologist's perspective; Otolaryngol Head Neck Surgery; 135(1); pp. 46-51; Jul. 2006.
Goss et al.; Comprehensive compilation of empirical ultrasonic properties of mammalian tissues; The Journal of the Acoustical Society of America, 64(2); pp. 423-457 <DOI:10.1121/1.382016>; Aug. 1978.
Griesbauer et al.; Wave propagation in lipid monolayers; Biophysical Journal; 97(10); pp. 2710-2716; Nov. 15, 2009.
Haar et al.; Therapeutic ultrasound; European Journal of Ultrasound; 9(1); pp. 3-9; Mar. 1, 1999.
Hamani et al.; Deep Brain Stimulation for the Treatment of Epilepsy; International Journal of Neural Systems; 19(3); pp. 213-226 <DOI:10.1142/S0129065709001975>; Jun. 2009.
Hauptman et al.; Potential surgical targets for deep brain stimulation in treatment-resistant depression; Neurosurg Focus; 25(1); E3, doi: 10.3171/FOC/2008/25/7/E3; 9 pages; (year of pub. sufficiently earlier than effective US filing date and any foreign priority date) 2008.
Hayner et al.; Numerical analysis of ultrasonic transmission and absorption of oblique plane waves through the human skull; The Journal of the Acoustical Society of America; 110(6); pp. 3319-3330 <DOI:10.1121/1.1410964>; Dec. 2001.
Heimburg; Lipid ion channels; Biophysical Chenistry; 150(1); pp. 2-22; Aug. 1, 2010.
Huerta et al.; Transcranial magnetic stimulation, synaptic plasticity and network oscillations; Journal of NeuroEngineering and Rehabilitation; 6(7); 10 pages <DOI:10.1186/1743-0003-6-7>; Mar. 2009.
Hynynen et al.; 500-element ultrasound phased array system for noninvasive focal surgery of the brain: a preliminary rabbit study with ex vivo human skulls; Magnetic Resonance in Medicine; 52(1); pp. 100-107; Jul. 2004.
Hynynen et al.; Clinical applications of focused ultrasound—the brain; International Journal of Hyperthermia; 23(2); pp. 193-202; Jan. 1, 2007.
Hynynen et al.; Demonstration of potential noninvasive ultrasound brain therapy through an intact skull; Ultrasound in Medicine and Biology; 24(2); pp. 275-283; Feb. 1, 1998.
Jefferys et al.; Synchronized bursting of CA1 hippocampal pyramidal cells in the absence of synaptic transmission; Nature; vol. 300; pp. 448-450 <DOI:10.1038/300448a0>; Dec. 1982.
Johansen-Berg et al.; Anatomical connectivity of the subgenual cingulate region targeted with deep brain stimulation for treatment-resistant depression; Cerebral Cortex: 18(6); pp. 1374-1383; Oct. 10, 2007.
Komisaruk et al.; Brain activation during vaginocervical self-stimulation and orgasm in women with complete spinal cord injury: fMRI evidence of mediation by the vagus nerves; Brain Research; 1024(1-2); pp. 77-88; Oct. 22, 2004.
Komisaruk et al.; Functional MRI ofthe brain during orgasm in women; Annual review of Sex Research; 16(1); pp. 62-86; Mar. 1, 2005.
Latikka et al; Conductivity of living intracranial tissues; Physics in Medicine and Biology; 46(6); pp. 1611-1616; Jun. 2001.
Lee et al.; Neural correlates of affective processing in response to sad and angry facial stimuli in patients with major depressive disorder; Psychopharmacology and Biological Psychiatry; 32(3); pp. 778-785; Apr. 1, 2008.
Lee et al.; The neural substrates of affective processing toward positive and negative affective pictures in patients with major depressive disorder; Progress in Neuro-Psychopharmacology and Biological Psychiatry; 31(7); pp. 1487-1492; Oct. 1, 2007.
Lessmann et al.; Neurotrophin secretion: current facts and future prospects; Progress in Neurobiology; 69(5); pp. 341-374 <DOI:10.1016/S0301-0082(03)00019-4>; Apr. 2003.
Li et al.; Synaptic vesicle recycling studies in transgenic mice expressing synaptophluorin; Proc. Natl. Acad. Sci. USA; 102(17); pp. 6131-6136; Apr. 26, 2005.
Lipton et al.; Single-pulse transcranial magnetic stimulation for acute treatment of migraine with aura: a randomised, double-blind, parallel-group, sham-controlled trial; Lancet Neurology; 9(4); pp. 373-380; Apr. 1, 2010.
Mayberg et al.; Deep brain stimulation for treatment-resistant depression; Neuron; 45(5); pp. 651-660; Mar. 3, 2005.
Mayo Clinic; Bipolar disorder: treatments drugs. Mayo Clinic. Aug. 2012. 10 pages; www.mayoclinic.com. Accessed Dec. 17, 2012.
McNamara; Cellular and molecular basis of epilepsy; The Journal of Neuroscience; 14(6); pp. 3413-3425 <DOI:10.1523/JNEUROSCI.14-06-03413.1994>; Jun. 1994.
Meloy et al.; Neurally augmented sexual function in human females: a preliminary investigation; Neuromodulation: Technology at the Neural Interface; 9(1); pp. 34-40: Jan. 1, 2006.
Mendelsohn et al.; Neurosurgeons' perspectives on psychosurgery and neuroenhancement: a qualitative study at one center; Journal of Neurosurgery; 113(6); pp. 1212-1218; Dec. 2010.
Menkes et al.; Right frontal lobe slow frequency repetitive transcranial magnetic stimulation (SF r-TMS) is an effective treatment for depression: a case-control pilot study of safety and efficacy; Journal of Neurology, Neurosurgery and Psychiatry; 67(1); pp. 113-115; Jul. 1, 1999.
Mihran et al.; Temporally-specific modification of myelinated axon excitability in vitro following a single ultrasound pulse; Ultrasound in Medicine and Biology; 16(3): pp. 297-309; 26 pages; (Author Manuscript); Jan. 1, 1990.
Milad et al.; The rote of the orbitofrontal cortex in anxiety disorders; Annals of the New York Academy of Sciences; 1121(1); pp. 546-561; Dec. 1, 2007.

(56) References Cited

OTHER PUBLICATIONS

Miller et al.: Enhanced artistic creativity with temporal lobe degeneration: Lancet; 348(9043); pp. 1744-1745; Dec. 21, 1996.
Miller et al.; Assessment tools for adult bipolar disorder; Clinical Psychology: Science and Practice; 16(2); pp. 188-201; 18 pages; (Author Manuscript); Jun. 1, 2009.
Morris et al.; Lipid Stress at Play: Mechanosensitivity of Voltage-Gated Channels; Current Topics in Membranes; 59; pp. 297-338; Jan. 1, 2007.
Morris et al.; Nav channel mechanosensitivity: activation and inactivation accelerate reversibly with stretch; Biophysical Journal; 93(3); pp. 822-833; Aug. 1, 2007.
Muehlberger et al. Lasting outcome of the surgical treatment of migraine headaches—a four year follow-up. Meeting of the American Society of Plastic Surgery. Abstract #14728 Nov. 3, 2008.
Nakashiba et al.; Hippocampal CA3 Output Is Crucial for Ripple-Associated Reactivation and Consolidation of Memory; Neuron; 62(6); pp. 781-787 <DOI:10.1016/j.neuron.2009.05.013>; Jun. 2009.
Nakao et al.; Working memory dysfunction in obsessive-compulsive disorder: a neuropsychological and functional MRI study; Journal of Psychiatric Research; 43(8); pp. 784-791; May 1, 2009.
Nitsche et al.; Excitability changes induced in the human motor cortex by weak transcranial direct current stimulation; The Journal of Physiology; 527(3); pp. 633-639; Sep. 1, 2000.
Norton; Can ultrasound be used to stimulate nerve tissue?; Biomedical Engineering Online; 2(1); 6; 9 pages; Mar. 4, 2003.
O'Brien; Ultrasound-biophysics mechanisms; Progress in Biophysics and Molecular Biology; 93(1-3); pp. 212-255; (Author Manuscript) Jan. 1, 2007.
Pascual-Leone et al.; Responses to rapid-rate transcranial magnetic stimulation of the human motor cortex; Brain: A Journal of Neurology; 117(4); pp. 847-858 <DOI:10.1093/brain/117.4.847>; Aug. 1994.
Patoine; Deep brain stimulation for severe depression: new results suggest it works, but how? Dana Foundation; retrieved May 30, 2018 from the internet (https://web.archive.org/web/20141228035621/http://www.dana.org:80/News/Details.aspx?id=43521); 5 pages; Mar. 5, 2012.
Petrov et al.; Flexoelectric effects in model and native membranes containing ion channels; European Biophysics Journal; 22(4); pp. 289-300; Oct. 1, 1993.
Poo: Neurotrophins as synaptic modulators; Nature Reviews Neuroscience; 2(1); pp. 24-32 <DOI:10.1038/35049004>; Jan. 2001.
Racine; Modification of seizure activity by electrical stimulation: I. after-discharge threshold; Electroencephalography and Clinical Neurophysiology; 32(3); pp. 269-279 <DOI:10.1016/0013-4694(72)90176-9>; Mar. 1972.
Reiman et al.; Neuroanatomical correlates of a lactate-induced anxiety attack; Arch Gen Psychiatry; 46(6); pp. 493-500; Jun. 1, 1989.
Rinaldi et al., Modification by focused ultrasound pulses of electrically evoked responses from an in vitro hippocampal preparation; Brain Research; 558(1); pp. 36-42; Aug. 30, 1991.
Sailer et al.; Effects of peripheral sensory input on cortical inhibition in humans; The Journal of Physiology; 544(2); pp. 617-629; Oct. 1, 2002.
Sankaranarayanan et al.; The use of phluorins for optical measurements of presynaptic activity; Biophys. J.; 79(4); pp. 2199-2208; Oct. 2000.
Satow et al.; Mirth and laughter arising from human temporal cortex; Journal of Neurology, Neurosurgery and Psychiatry; 74(7); pp. 1004-1005; Jul. 1, 2003.
Schienle et al.: Symptom provocation and reduction in patients suffering from spider phobia: an fMRI study on exposure therapy; European Archives of Pschiatry and Clinical Neuroscience; 257(8); pp. 486-493; doi 10.1007/s00406-007-0754-y; 8 pages; Dec. 1, 2007.
Shealy et al.; Reversible effects of ultrasound on spinal reflexes: Archives of Neurology; 6(5); pp. 374-386; May 1962.

Shirvalkar et al.; Cognitive enhancement with central thalamic electrical stimulation, Proceedings of the National Academy of Sciences USA; 103(45); pp. 17007-17012; Nov. 7, 2006.
Snyder et al.; Concept formation: 'object' attributes dynamically inhibited from conscious awareness; Journal of Integrative Neuroscience; 3(1); pp. 31-46; Mar. 2004.
Snyder et al.; Savant-like skills exposed in normal people by suppressing the left fronto-temporal lobe; Journal of Integrative Neuroscience; 2(2); pp. 149-158; 9 pages; (Author Manuscript); Dec. 2003.
Sperli et al.; Contralateral smile and laughter, but no mirth, induced by electrical stimulation of the cingulate cortex; Epilepsia; 47(2); pp. 440-443; Feb. 1, 2006.
Stoppini et al.; A simple method for organotypic cultures of nervous tissue: Journal of Neuroscience Methods; 37(2); pp. 173-182; Apr. 1, 1991.
Sukharev et al.; Mechanosensitive channels: multiplicity of families and gating paradigms; Sci STKE; 2004(219); 25 pages; ref4-; doi 10.1126/stke.2192004re4; Feb. 10, 2004.
Ter Haar; Therapeutic applications of ultrasound; Progress in Biophysics and Molecular Biology; 93(1-3); pp. 111-129; Jan.-Apr. 2007.
Tsui et al.; In vitro effects of ultrasound with different energies on the conduction properties of neural tissue; Ultrasonics; 43(7); pp. 560-565; Jun. 1, 2005.
Tufail et al.; Transcranial pulsed ultrasound stimulates intact brain circuits; Neuron; 66(5); pp. 681-694; Jun. 10, 2010.
Tufail et al.; Ultrasonic neuromodulation by brain stimulation with transcranial ultrasound; Nature Protocols; 6(9); pp. 1453-1470; Sep. 2011.
Tyler et al.; From Acquisition to Consolidation: On the Role of Brain-Derived Neurotrophic Factor Signaling in Hippocampal-Dependent Learning; Learning & Memory; 9(5); pp. 224-237 <DOI:10.1101/lm.51202>; Sep.-Oct. 2002.
Tyler; Machining physiological intelligence; QT Quarterly; 2(1); pp. 33-37; (year of pub. sufficiently earlier than effective US filing date and any foreign priority date) Summer 2010.
Tyler et al.; Remote excitation of neuronal circuits using low-intensity, low-frequency ultrasound. PLoS One; 3(10); e3511; doi 10.1371/journal.pone.0003511; 11 pages; Oct. 29, 2008.
Velling et al.; Modulation of the functional state of the brain with the aid of focused ultrasonic action; Neuroscience and Behavioral Physiology; 18(5); pp. 369-375; Sep.-Oct. 1988.
Wagner et al.; Noninvasive human brain stimulation; Annu. Rev. Biomed. Eng.; 9; pp. 527-565; Aug. 15, 2007.
White et al.; Local frequency dependence in transcranial ultrasound transmission: Physics in Medicine & Biology; 51(9); pp. 2293-2305 <DOI:10.1088/0031-9155/51/9/013>; Apr. 2006.
White et al.; Longitudinal and shear mode ultrasound propagation in human skull bone; Ultrasound in Medicine & Biology; 32(7); pp. 1085-1096 <DOI:10.1016/j.ultrasmedbio.2006.03.015>; Jul. 2006.
Yang et al.; Transcranial ultrasound stimulation: a possible therapeutic approach to epilepsy; Medical Hypotheses; 76(3); pp. 381-383; Mar. 1, 2011.
Ylinen et al.; Sharp wave-associated high-frequency oscillation (200 Hz) in the intact hippocampus: network and intracellular mechanisms: Journal of Neuroscience; 15(1): pp. 30-46 <DOI:10.1523/JNEUROSCI.15-01-00030.1995>; Jan. 1995.
Yoo et al.; Focused ultrasound modulates region-specific brain activity; Neuroimage; 56(3); pp. 1267-1275; Jun. 1, 2011.
Yoo et al.; Transcranial focused ultrasound to the thalamus alters anesthesia time in rats; Neuroreport; 22(15); pp. 783-787: Oct. 26, 2011.
Young et al.; Functional Effects of Focused Ultrasound on Mammalian Nerves; Science; 134(3489); pp. 1521-1522 <DOI:10.1126/science.134.3489.1521>; Nov. 1961.
Yucel et al.; Anterior cingulate dysfunction: implications for psychiatric disorders?; Journal of Psychiatry and Neuroscience; 28(5); pp. 350354; Sep. 2003.
Zaehle et al.; Transcranial alternating current stimulation enhances individual alpha activity in human EEG; PLoS One; 5(11); e13766; doi 10.1371/journal.pone.0013766; 7 pages; Nov. 1, 2010.

(56) References Cited

OTHER PUBLICATIONS

Zaghi et al.; Noninvasive brain stimulation with low-intensity electrical currents: putative mechanisms of action for direct and alternating current stimulation; Neuroscientist; 16(3); pp. 285-307; Jun. 2010.

Zhang et al.: Focusing Ultrasound with an Acoustic Metamaterial Network; Physical Review Letters; 102(19) pp. 194301-194304 <DOI:10.1103/PhysRevLett.102.194301>; May 2009.

Zang et al.; Multimodal fast optical interrogation of neural circuirtry; Nature; 446(7136); pp. 633-639; Apr. 2007.

Zhao et al.; Altered default mode network activity in patient with anxiety disorders: an fMRI study; European Journal of Radiology; 63(3); pp. 373-378; Sep. 1, 2007.

Tyler; U.S. Appl. No. 16/618,101 entitled "Systems and methods for generating an elastogram of brain tissue using mesoscopic wavelength ultrasound," filed Nov. 27, 2019.

Hool et al.; U.S. Appl. No. 16/642,750 entitled "In-ear electrode assembly for non-invasive nerve stimulation," filed Feb. 27, 2020.

Nelson et al.; Ultrasound biosafety considerations for the practicing sonographer and sonologist; The American Institute of Ultrasound in Medicine; J Ultrasound Medicine; vol. 28; pp. 139-150; 2009.

\* cited by examiner

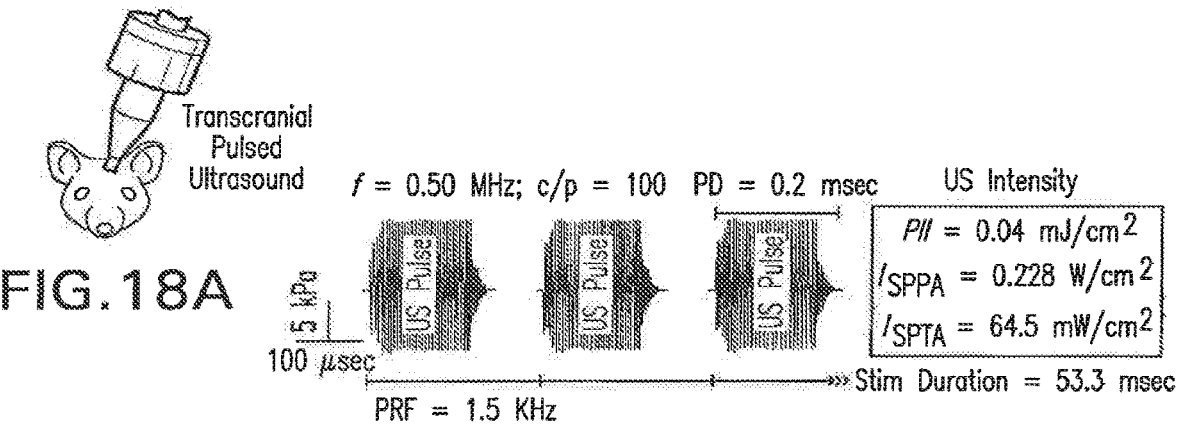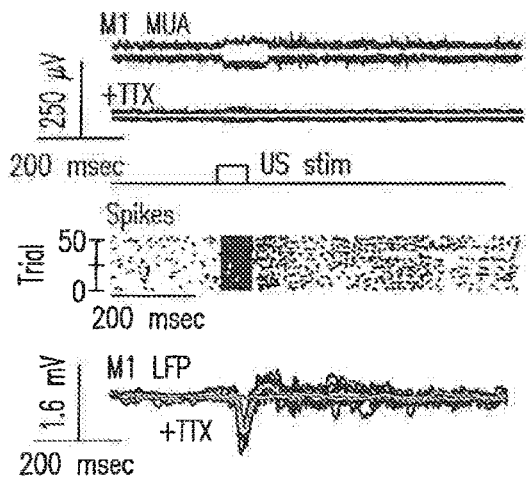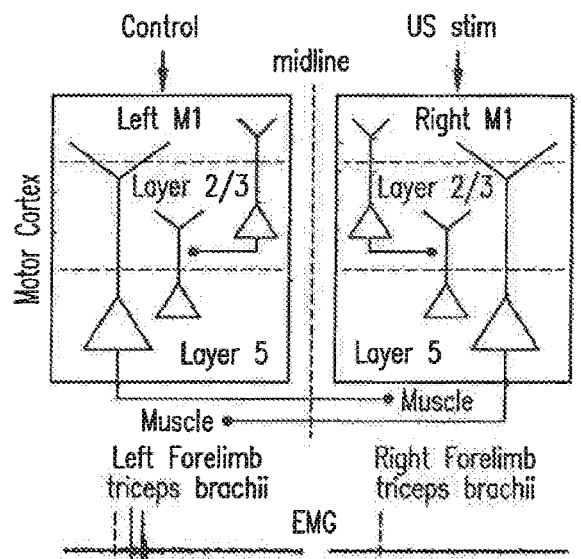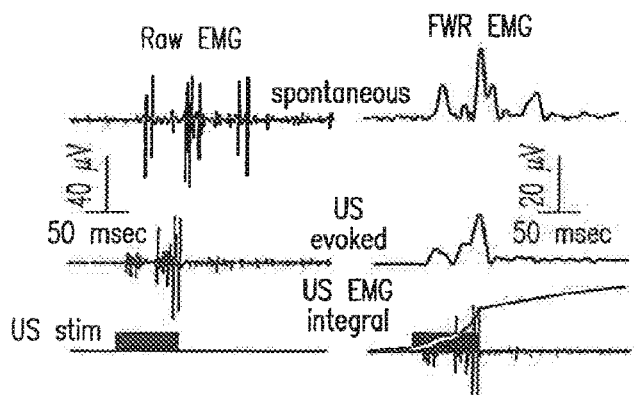

Sine wave-generated 0.50 MHz 10 cycle pulses repeated

FIG.28A

Sine wave-generated 0.25 MHz 10 cycle pulses repeated

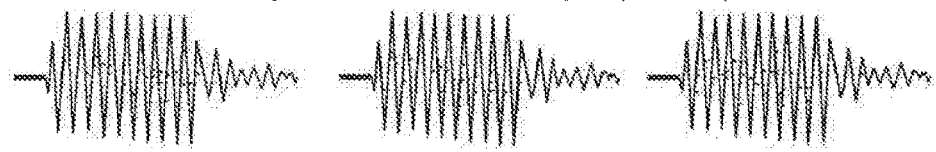

FIG.28B

Sine wave-generated 0.25 MHz 10 cycle pulses repeated

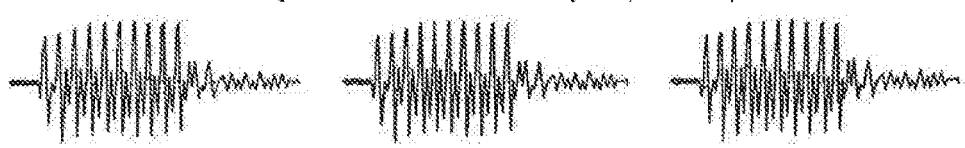

FIG.28C

Alternating sine wave-generated 0.50 and 0.25 MHz 10 cycle pulses repeated

FIG.28D

Alternating square wave-generated 0.25 and sine wave-generated 0.50 MHz 10 cycle pulses repeated

FIG.28E

Alternating sine wave-generated 0.25 and square wave-generated 0.20 MHz 10 cycle pulses repeated

FIG.28F

METHODS AND DEVICES FOR MODULATING CELLULAR ACTIVITY USING ULTRASOUND

CROSS REFERENCE TO RELATED APPLICATIONS

This application is a continuation of U.S. patent application Ser. No. 15/192,749, filed Jun. 24, 2016, now U.S. Pat. No. 10,556,132, which is a continuation of U.S. patent application Ser. No. 14/460,007, filed Aug. 14, 2014, now U.S. Pat. No. 9,403,038, which is a continuation of U.S. patent application Ser. No. 14/025,586, filed Sep. 12, 2013, now U.S. Pat. No. 8,858,440, which is a continuation of U.S. patent application Ser. No. 13/003,853, filed Apr. 6, 2011, now U.S. Pat. No. 8,591,419, which is a National Stage Entry of PCT/US2009/050560, filed Jul. 14, 2009, which claims priority to U.S. Provisional Application Ser. No. 61/080,666, filed Jul. 14, 2008, and to U.S. Provisional Application Ser. No. 61/175,413, filed May 4, 2009, the full disclosures of which are incorporated herein by reference.

FIELD

The present invention relates to ultrasound modulation of cellular activities, including nerves and other cells found in human and animals.

BACKGROUND

Ultrasound (US) has been used for many medical applications, and is generally known as cyclic sound pressure with a frequency greater than the upper limit of human hearing. The production of ultrasound is used in many different fields, typically to penetrate a medium and measure the reflection signature or supply focused energy. For example, the reflection signature can reveal details about the inner structure of the medium. A well known application of this technique is its use in sonography to produce a picture of a fetus in a womb. There are other applications which may provide therapeutic effects, such as lithotripsy for ablation of kidney stones or high-intensity focused ultrasound for thermal ablation of brain tumors.

A benefit of ultrasound therapy is its non-invasive nature. For example, methods for modulating neural activity include both invasive and non-invasive techniques. Neuromodulation techniques such as deep brain stimulation (DBS) and repetitive transcranial magnetic stimulation have gained attention due to their therapeutic utility in the management of numerous neurological/psychiatric diseases. These methods for stimulating neuronal circuits have been demonstrated to hold promise for the treatment of such diseases and disorders as Parkinson's, Alzheimer's, coma, epilepsy, stroke, depression, schizophrenia, addiction, neurogenic pain, cognitive/memory dysfunction, and others. In the laboratory setting, recent work demonstrated efficacy for millisecond optical control of individual neurons and synapses in intact brain circuits.

The current goals of neurostimulation techniques are to modulate neuronal activity and thereby nervous system function by delivering exogenous energy to intact circuits. However, many of these techniques, such as DBS and vagus nerve stimulation (VNS) require the surgical implantation of stimulating electrodes, an invasive, expensive and even dangerous procedure. For example, the surgical implantation of stimulating electrodes increases secondary medical risks such as infection. The primary cost associated with the surgical implantation of neurostimulation devices is approximately $17,000 to $60,000 per patient, which costs do not take into account the significant costs of pre- and post-operative care.

Ultrasound refers to cyclical vibrations in a frequency range above human hearing, i.e., above about 20 thousand cycles per second (kilohertz, kHz) and including vibrational frequencies of tens and hundreds of millions of cycles per second (MegaHertz, MHz), e.g., a range from about 0.02 to 200 MHz. Ultrasound was first shown to be capable of modulating neuronal activity by inducing reversible suppression. It was earlier demonstrated that ultrasound delivered to the lateral geniculate nucleus of cats in vivo, reversibly suppressed light-evoked potentials in the visual cortex.

Approaches to affecting neural activity in the brain using ultrasound have employed ultrasound frequencies above about 0.6 MHz applied for extended periods of times (several seconds to several minutes), and at intensity levels above about 10 Watts per square centimeter (mW/cm$^2$, where 1 mW=$10^{-3}$ Watts, and 1 cm=$10^{-2}$ meters). Many of these approaches are intended to produce macroscopic effects, such as tissue ablation during high intensity focused ultrasound (HIFU). Ultrasound frequencies used for imaging typically range from 2.5 to 7.5 MHz.

What are needed are non-invasive and effective therapies for modulating cellular activity, including the activity of neural cells and other types of cells.

SUMMARY OF THE DISCLOSURE

The present invention comprises methods and devices for modulating the activity or activities of living cells, such as cells found in or derived from humans, animals, plants, insects, microorganisms and other organisms. Methods of the present invention comprise use of the application of ultrasound (US), such as low-intensity, low-frequency ultrasound, to living cells to affect the cells and modulate the cells' activities. Devices of the present invention comprise one or more components for generating ultrasound waves, such as ultrasonic emitters, transducers or piezoelectric transducers, composite transducers, CMUTs (capacitive micromachined ultrasound transducers), and may be provided as single or multiple transducers or in an array configurations. The ultrasound waves may be of any shape, and may be focused or unfocused, depending on the application desired. The ultrasound may be at an intensity in a range of about 0.0001 to about 900 mW/cm$^2$ and an ultrasound frequency in a range of about 0.02 to about 1.0 MHz at the site of the tissue to be modulated.

Methods of the present invention comprise modulating cellular activity by providing ultrasound waves to cells or tissues at an effective intensity and for effective time range so that the cell activity is altered. Methods comprise treatment of physiological or pathological conditions including, but not limited to, Parkinson's disease, Alzheimer's disease, coma, epilepsy, stroke, depression, schizophrenia, addiction, neurogenic pain, cognitive/memory dysfunction, diabetes, obesity, obsessive compulsive disorders, traumatic brain injury, post-traumatic stress disorder (PTSD), coma, minimally conscious or vegetative states, locked in syndrome, spinal cord injuries, peripheral neuropathies, migraine, epilepsy, and other pathologies associated with organs of the human or animal body. Methods comprise mapping of the brain, stimulating or inhibiting nerve activity such as the vagus nerve, stimulating physiological responses of cells, tissues, or organs, photoacoustic tomography, and other uses of ultrasound waves in the body.

A method of the present invention comprises acoustically coupling component for generating ultrasound waves, such as an ultrasound transducer, to an external surface or inside the body of an animal, human, insect, plant, or to plates or containers of cells or tissues. The ultrasound transducer is driven to form in the cells, tissues, or organs pressure fluctuations, a stimulus waveform, with an intensity above about 0.001 milliWatts per square centimeter ($mW/cm^2$) and below about 900 $mW/cm^2$ and an ultrasound frequency below about 1.0 MegaHertz (MHz), from about 0.02 MHz to about 1.0 MHz, at the site of the tissue to be manipulated.

A method of the present invention comprises treating disorders comprising acoustically coupling an ultrasound transducer to an external surface of a subject or container to be treated. The ultrasound transducer is driven to deliver an effective dose of ultrasound at an intensity above about 20 $mW/cm^2$ and below about 900 $mW/cm^2$ and an ultrasound frequency below about 1.0 MHz at the site of the tissue or cells to be manipulated.

A device of the present invention may comprise logic encoded in tangible form that is configured to perform one or more steps of the above methods.

DESCRIPTION OF THE DRAWINGS

The accompanying drawings, which are incorporated in and constitute a part of this specification, illustrate several embodiments and together with the description illustrate the disclosed compositions and methods.

FIG. 18A shows the illustration of the method used to transmit laterally focused ultrasound stimulus waveforms to intact motor cortex.

FIG. 18B shows an example of the strategy and parameters used in constructing low-intensity US stimulation waveforms.

FIG. 18C shows raw and average ultrasound-evoked multi-unit activity (MUA) recorded from M1 cortex.

FIG. 18D shows an approach to stimulating descending corticospinal tracts with transcranial ultrasound.

FIG. 18E shows electromyogram (EMG) traces for a spontaneous and ultrasound-evoked event.

FIG. 28A shows an illustration of the repetition of 10 cycles of sine wave-generated ultrasound pulses at 0.50 MHz.

FIG. 28B shows an illustration of the repetition of 10 cycles of sine wave-generated ultrasound pulses at 0.25 MHz.

FIG. 28C shows an illustration of the repetition of 10 cycles of square wave-generated ultrasound pulses at 0.25 MHz.

FIG. 28D shows an illustration of the repetition of alternating 10 cycles of sine wave-generated ultrasound pulses at 0.50 and 0.25 MHz.

FIG. 28E shows an illustration of the repetition of alternating 10 cycles of square wave-generated ultrasound pulses at 0.25 MHz and sine wave-generated ultrasound pulses at 0.50 MHz.

FIG. 28F shows an illustration of the repetition of alternating 10 cycles of sine wave-generated ultrasound pulses at 0.25 MHz and square wave-generated ultrasound pulses at 0.20 MHz.

DETAILED DESCRIPTION

Figure 1:
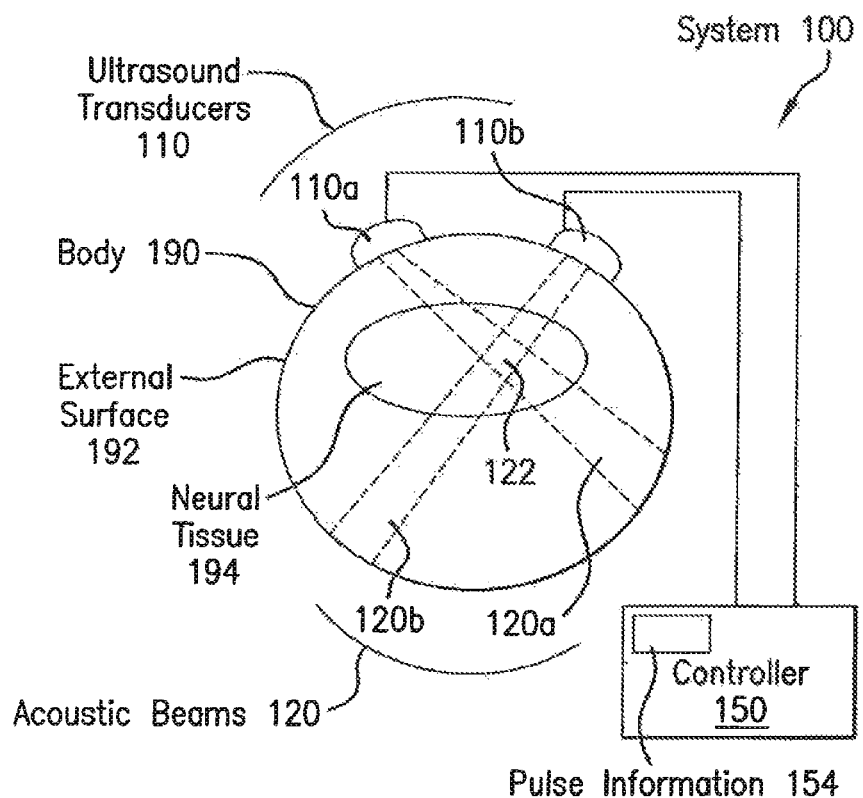
FIG. 1 shows a block diagram that illustrates an example system for modulating neural activity.

The present invention comprises methods and devices for modulating the activity of cells. The methods and devices comprise use of ultrasound waves directed to cells which may be found in cell cultures or in vivo in living bodies. Methods of the present invention comprise use of the application of ultrasound waves, such as low intensity, low frequency ultrasound, or low intensity ultrasound, to living cells to affect the cells and modulate the cells' activities. Devices of the present invention comprise one or more components for generating ultrasound waves, including but not limited to ultrasonic emitters, transducers or piezoelectric transducers, composite transducers, CMUTs (capacitive micromachined ultrasound transducers), and which may be provided as single or multiple transducers or in array configurations. The ultrasound waves may be of any shape, and may be focused or unfocused, depending on the application desired. The ultrasound may be at an intensity in a range of about 0.0001 to about 900 $mW/cm^2$ and an ultrasound frequency in a range of about 0.02 to about 1.0 MHz at the site of the cells or tissue to be modulated.

As disclosed herein, aspects of the invention are described in the context of providing ultrasound to mammalian brain tissue in vitro and in vivo. However, the invention is not limited to this context. Aspects of the invention comprise providing ultrasound to cells, where ever located in a living body, such as human, animal, insect, avian bodies, or to cells found in cell culture, or microbial or one celled organisms. For example, the activity of neural tissue may be modulated in vivo in the brain or elsewhere in the body of a living organism, or in an in vitro sample mounted in a vessel of any kind for any purposes, including elucidating the functioning of normal or disordered neural tissue, or diagnosing or treating a neural disorder in a living organism. As used herein a neural disorder includes any functional or physiological abnormality or injury or psychiatric disorder, such as stress and depression. As used herein neural tissue includes tissue with neurons within it, or neural precursor cells, such as neural stem cells, neurons, axons, neural cell bodies, ganglia, dendrites, synaptic regions, neuronal tissue, or other cells positioned in a living organism among neurons, such as glial cells, oligodendrites, or astrocytes. Treatment of neural tissue is exemplary and is not intended to limit the invention.

Ultrasound has been shown to influence neuronal activity by suppressing the amplitudes and/or conduction velocity of evoked action potentials. Detailed investigations are lacking however and the underlying mechanisms of these effects remain unknown. Moreover, nearly all of these previous studies examining the effects of ultrasound on neuronal activity have implemented long irradiation times (minutes) with high-frequency (>1 MHz) ultrasound delivered at moderate intensity levels (>500 $mW/cm^2$). The use of moderate and high intensity, high-frequency ultrasound and long exposure times to control neuronal activity minimizes ultrasound's practicality for modulating neuronal activity in living organisms. The present invention comprises methods for low-intensity (<500 $mW/cm^2$), low-frequency ultrasound (<0.9 MHz) and effects on cellular modulation, such as methods for influencing neuronal activity. For example, low intensity may comprise about 450 $mW/cm^2$, 400 $mW/cm^2$, 350 $mW/cm^2$, 300 $mW/cm^2$, 250 $mW/cm^2$, 200 $mW/cm^2$, 150 $mW/cm^2$, 100 $mW/cm^2$, 50 $mW/cm^2$, 25 $mW/cm^2$, 10 $mW/cm^2$, and levels of ultrasound intensity within these stated amounts, including from about 450 $mW/cm^2$ to about 1 $mW/cm^2$. Low frequency ultrasound may comprise ranges from about 0.88 MHz to about 0.01 MHz, from about 0.80 MHz to about 0.01 MHz, 0.80 MHz to about 0.1 MHz, from about 0.70 MHz to about 0.1 MHz, from about 0.60 MHz to about 0.1 MHz, from about 0.50 MHz to about 0.1 MHz, from about 0.40 MHz to about 0.1 MHz, from about 0.30 MHz to about 0.1 MHz, from about 0.20 MHz to about 0.1 MHz, from about 0.10 MHz to about 0.1 MHz, and levels of ultrasound frequency within these stated amounts.

As used herein, the cited intensities and frequencies are the intensity and frequency levels at the effective tissue site, not the actual output number of the transducer. For example, the pressure waveform experienced at the site of the target tissue is below about 0.9 Mhz or 900 $mW/cm^2$. The output of a transducer may have to be much larger than the resulting effective amount at the target tissue site. For example, a transducer may output 90 W for transmission to an intact skull for the effective amount at the brain to be below about 0.9 Mhz or 900 mW/cm$^2$, as the skull absorbs a significant portion of ultrasound waves. Thus, the frequencies and intensities stated and claimed herein are the frequencies and intensities experienced at the target tissue site, not the output of the ultrasound transducers.

As used herein, providing ultrasound treatment or ultrasound to a target site to modulate cellular activity comprises providing an ultrasound stimulus waveform to a subject. The ultrasound stimulus waveform may also alternatively be referred to herein as a waveform, and the two terms are used interchangeably as can be understood by those skilled in the art. A stimulus waveform may be provided to a subject, human, animal or other subjects, once or multiple times in a single treatment, or in a continuous treatment regimen that continues for a day, days, weeks, months, years, or for the life of the subject. Determining the length of treatment needed is within the skills of medical and/or research professionals. It is contemplated by the present invention that a stimulus waveform may be pulsed or continuous, have one or multiple frequencies, and other characteristics as described herein. For example, in particular treatments, a pulsed ultrasound stimulus waveform may be transmitted for about 10 microseconds, for about 25 microseconds, for about 50 microseconds, for about 100 microseconds, for about 250 microseconds, for about 500 microseconds, for about 1000 microseconds, for about 2000 microseconds, for about 3000 microseconds, for about 4000 microseconds, for about 5000 microseconds, for about 1 second, for about 2 seconds, for about 3 seconds, for about 4 seconds, for about 5 seconds, for about 6 seconds, for about 7 seconds, for about 8 seconds, for about 9 seconds, for about 10 seconds, and then this treatment may be repeated for the same or a different length of time, one or more times. For example, a stimulus waveform may be provided every 11 seconds for a duration of about 250 microseconds for years, or for the life of the subject.

FIG. 1 is a block diagram that illustrates an example system 100 for modulating cellular activity, according to an embodiment wherein the target site is neural tissue. To illustrate the operation of system 100, a body 190 with an external surface 192 that encompasses neural tissue 194 is depicted. However, the system 100 does not include the body 190 or its external surface 192 or neural tissue 194. In some embodiments, the body 190 is a living organism, such as a human or animal or other subject, or a portion thereof, such as a head and skull. In some embodiments, the body is a vessel that contains an in vitro sample, such as a glass cylinder filled with water or artificial cerebrospinal fluid and a suspended slice extracted from the brain of an organism.

The system 100 includes components for generating ultrasound waves such as ultrasound transducers 110, including transducer 110a and transducer 110b, and controller 150. In some aspects, the transducer may be an emitting transducer, a receiving and transmitting transducer, or a receiving transducer. The ultrasound transducers 110 are connected to controller 150 for receiving waveform and power, and the transducers are driven by the controller. The transducers are acoustically coupled to the external surface 192 of body 190 in order to introduce acoustic energy into the body 190. The transducers 110 use the received waveform and power to emit ultrasound frequency acoustic beams 120, such as beam 120a from transducer 110a and beam 120b from transducer 110b. The controller 150 includes a process 154 for waveform formation, which determines the waveform to be emitted by transducers 110a into body 190. In some embodiments, the transducers are battery powered and receive only waveform information from controller 150.

Although a particular number of transducers and controllers are depicted in FIG. 1 for purposes of illustration, in other embodiments, more or fewer or the same number of transducers is included, and controller 150 is replaced by one or more devices that each perform a different or redundant function of controller 150, including the waveform formation process 154. Although FIG. 1 depicts separate wired connections between transducers 110 and controller 150 to send power and waveforms to transducers 110, in other embodiments one or more connections may be wireless, or carry power or waveforms for multiple transducers 110.

In the illustrated embodiment, the two transducers 110 each transmit an acoustic beam into body 190, which intersect in beam intersection region 122. In some embodiments, the waveform transmitted in a beam is effective in modulating neural activity everywhere the beam intersects the neural tissue. In some embodiments, the waveform transmitted in a beam is only effective (or more effective) in an intersection region 122 with another beam. In some embodiments, the transmitted waveforms are effective in only a portion of the intersection region 122, dependent upon interference patterns of constructive and destructive interference among the waveforms in the intersecting beams.

The intensity of the acoustic beam is given by the amount of energy that impinges on a plane perpendicular to the beam per unit time divided by the area of the beam on the plane, and is given in energy per unit time per unit area, i.e., the power density per unit area, e.g., Watts per square centimeter (W/cm$^2$). This is the spatial-peak temporal-average intensity (Ispta); and is used routinely for intensity hereinafter. In illustrated embodiments, the Ispta is less than 500 mW/cm$^2$. Another definition of intensity widely used in the art is spatial-peak pulse-average intensity (Ipa); for the multiple cycle pulses used in the illustrated embodiment the Ipa is typically less than 10 W/cm$^2$.

Any means known in the art may be used to transmit an acoustic beam 120 into a body 190. For example, Archimedes SI transducers (Array Therapeutic, Scottsdale, Ariz., USA) may be used, which are a type of piezo-electric transducers (PZT). An Archimedes SI has two peak response frequencies at which the transmitted acoustic pressure is 71% (−3 dB) of its maximum value. For example, Archimedes transducers had one peak at 0.44 MHz and another at 0.67 MHz. Other ultrasound transducers may be used, including but not limited to, Olympus NDT/Panametrics 0.5 MHz center frequency transducers, as well as Ultran 0.5 and 0.35 MHz center frequency transducers.

In some embodiments, capacitive micro-machined ultrasonic transducer (CMUT) technology may be applied. For example, CMUTs may be arranged in flexible array designs that comfortably permit adaptive beam forming and focusing. And in other embodiments the CMUTs may be mounted inside a body cavity to transmit ultrasound to cells, tissues, or organs. Furthermore, CMUTs may be mounted to the skull to transmit ultrasound to various brain regions.

Any devices known in the art may be used in controller 150. In an illustrated embodiment, waveforms were generated using an Agilent 33220A function generator (Agilent Technologies, Inc., Santa Clara, Calif., USA) and amplified using an ENI 240L RF amplifier. Pulses in some waveforms were triggered using a second Agilent 33220A function generator. Data controlling the above devices may be generated by waveform formation process 154 using a general purpose computer with software instructions, as described in more detail in a later section.

Although system 100 is depicted with two transducers and corresponding beams, more or fewer transducers or beams or both may be included in a system.

Systems and devices for providing ultrasound for the present invention may comprise materials that bend light or sound and can focus the waves. Such materials have been used to make super-lenses. Such materials, super-lenses and other similar components may be used to focus the ultrasound waves in the methods and devices of the present invention. For example, transducers, of any type, in conjunction with a focusing element such as a super-lens or metamaterial are used for focusing the ultrasound waves used to modulate cellular activity. Such materials can refract light backward, or have a negative index of refraction and have been referred to as a "metamaterial." An example of a metamaterial is a sound-focusing device comprising an aluminum array of narrow-necked resonant cavities with dimensions that are tuned to interact with ultrasound waves. The cavities may be filled with water. A focusing element, such as a metamaterial, may be used in conjunction with one or more transducers, and/or with phased arrays of transducers.

Figure 2:
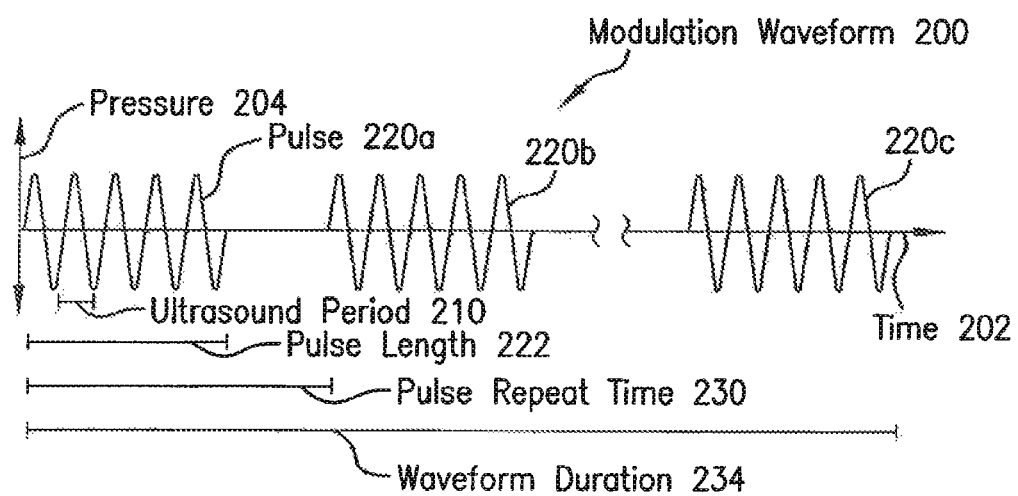
FIG. 2 shows a graph that illustrates an example ultrasound waveform for modulating neural activity.

FIG. 2 is a graph that illustrates an example ultrasound waveform 200 for modulating neural activity, according to an embodiment. The horizontal axis 202 indicates time, and the vertical axis 204 indicates pressure, both in arbitrary units. The modulating waveform 200 contains one or more pulses, such as pulse 220a and pulse 220b and pulse 220c. Each pulse includes one or more cycles at an ultrasound frequency. For example, pulse 220a includes five cycles of an ultrasound frequency with a period ($\tau$) 210 in seconds equal to the reciprocal of the frequency (f) in Hertz (i.e., $\tau=1/f$). The number of cycles in a pulse is designated cycles per pulse (c/p). The pulse length 222 is designated PL and is given in seconds by the product of the period r and number of cycles per pulse c/p, i.e., $PL=\tau*c/p$.

Pulses are separated by quiescent periods that are related to the time between pulse starts, shown in FIG. 2 as pulse repeat time 230. The reciprocal of the pulse repeat time 230 in seconds is the pulse repeat rate in Hertz, designated herein the pulse repeat frequency PRF, to distinguish it from the ultrasound frequency f. In some embodiments, the pulse repeat frequency PRF is a constant for a waveform 200. In some embodiments, the pulse repeat frequency PRF increases from a minimum (PRF min) to a maximum (PRF max) over a time interval called a ramp time. For example, in some embodiments, PRF increases from PRF min=0 to PRF max=3000 Hz over ramp time=5 seconds. In other embodiments the PRF may range from 0.001 to 10 KHz. The waveform continues for a waveform duration 234 that ends with the last pulse n the wave form. The number of pulses in the waveform is designated Np.

The pressure amplitude of the ultrasound wave is proportional to a voltage range used to drive a piezoelectric transducers (PZT). For example, in the illustrated embodiments, the voltage range is selected between 100 milliVolts (mV, $1 mV=10^{-3}$ Volts) and 500 mV, which correspond to intensity levels less than 500 $mW/cm^2$. Although pulses are shown in FIG. 1 as sine waves having a single ultrasound frequency, in various other embodiments, other oscillating shapes may be used, such as square waves, or a pulse includes multiple ultrasound frequencies composed of beat frequencies, harmonics, or a combination of frequencies generated by constructive or deconstructive interference techniques, or some or all of the aforementioned.

Figure 3:
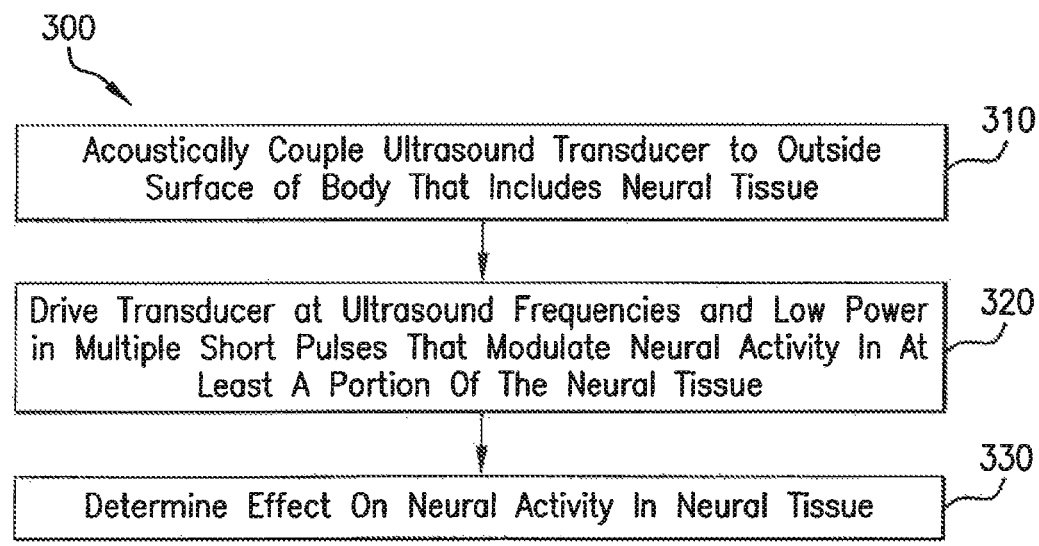
FIG. 3 shows a flow diagram that illustrates, at a high level, a method for modulating neural activity.

FIG. 3 is a flow diagram that illustrates, at a high level, a method 300 for modulating neural activity according to an embodiment. Although a particular number of steps are shown in a particular order for purposes of illustration, in other embodiments, one or more steps may be performed in a different order or overlapping in time, in series or in parallel, or one or more steps may be omitted or added, or changed in some combination of ways.

In step 310, one or more ultrasound transducers are acoustically coupled to an outside surface of a body which may include or encompass neural tissue, or other tissues. In some embodiments, one or more transducers are phase transducer arrays. In some embodiments the body is a vessel with artificially produced brain fluid in which is suspended a slice of neural tissue. In several of these embodiments, the coupling is direct contact of an ultrasound piezoelectric hydrophone with the fluid in the vessel, or a mechanical coupling of a piezoelectric material to a wall of the vessel. In therapeutic embodiments, the body is a patient and the transducers are acoustically coupled to the skin of the patient, such as on the head or back. In some embodiments, acoustic coupling is affected by a gel or other substance, well known in the art, which prevents loss of acoustic energy to the air surrounding the patient. In some embodiments, step 310 includes shaving hair from a portion of a patient's head. In some embodiments, air-coupled ultrasound transducers transmit ultrasound pulses through the air in a manner to target the neural tissue by penetrating the skin, bone, muscle, and underlying fascia. In some embodiments, one or more ultrasound transducers may be bolted directly to a structure such as the skull underneath the skin. In some embodiments, ultrasound transducers may be mounted inside the cavity of a patient, such as in the peritoneal or thoracic cavity.

In step 320, the one or more transducers (or phase transducer arrays) coupled to the body are driven at ultrasound frequencies and low intensity in multiple short pulses that are effective in modulating neural activity in at least a portion of the neural tissue. For example, the beam intersects only a portion of the neural tissue, or multiple beams intersect in a portion of the neural tissue and only tissue in regions of constructive and or deconstructive interference is modulated. It is noted that the scale of constructive interference patters is millimeters based on the wavelength of ultrasound in neural tissue. For example, the speed of sound in water approximates the speed of sound in soft body tissue and is about 1500 meters per second. Thus at ultrasound frequencies from 0.1 to 1 MHz, the wavelength of ultrasound is between about 1.5 mm and about 15 mm. Constructive and or deconstructive interference patterns are on the same order as these wavelengths.

Ultrasound frequencies may be selected to penetrate to the neural tissue or target tissue. For samples suspended in vessels and transducers attached to the outside all of the vessel, the ultrasound frequency is selected in a range that effectively passes through the vessel (e.g., glass) wall with little attenuation. For transducers that directly contact the brain fluid, penetrating a different material is not a significant issue. For transducers placed on a patient's head, the ultrasound frequency should pass through the skull with little absorption to prevent heating the skull, which can cause discomfort or injury to the patient. It has been found that ultrasound frequencies between about 0.2 MHz and about 0.9 MHz pass through the skull with little deleterious heating even at high intensity if proper cooling precautions are implemented. The ultrasound intensity is chosen to have a modulating effect on neural tissue without damage to the tissue. It has been found that intensities below about 500 mW/cm² are effective in modulating neural activity without detected damage to neurons and other cells in brain tissue.

In step 330, an effect on neural activity is determined. In various embodiments, the effect is stimulation or suppression of neural activity. For example, in some embodiments, an increase or decrease in fluorescence that indicates neural activity is detected. In some embodiments, a membrane voltage change is detected. In various other embodiments, other phenomena that reflect neural activity are monitored, such as Positron Emission Tomography (PET) scans and brain metabolites signatures in nuclear magnetic resonance imaging (MRI) scans or other measures of neural activity such as electroencephalogram (EEG) or magnetoencephalography (MEG). In therapeutic embodiments, a change in a progression or symptom of a disease or disorder is determined. In some embodiments, for example in embodiments in which therapeutic effectiveness is well established, step 330 may be omitted.

Figure 4A:
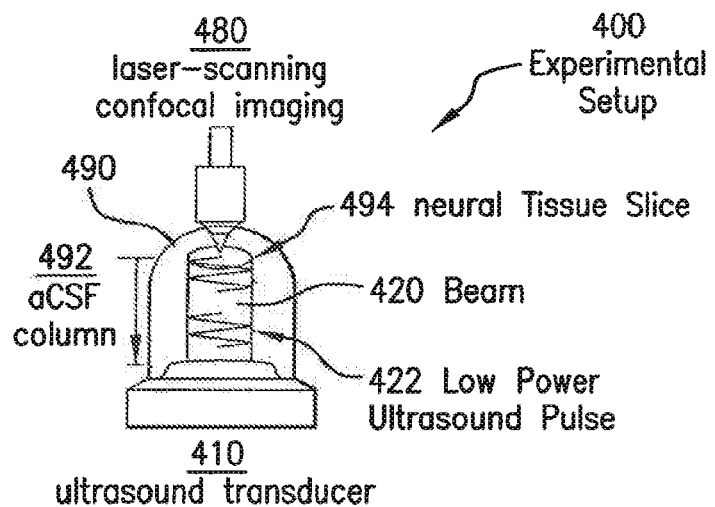
FIG. 4A shows an illustration of an experimental setup to demonstrate effects on neural activity from an ultrasound waveform.

FIG. 4A is a block diagram that illustrates an example experimental setup 400 to demonstrate effects on neural activity from an ultrasound waveform, according to an embodiment. The setup 400 includes a vessel that contains artificial cerebrospinal fluid (aCSF) 490 and neural tissue slice 494 loaded with a fluorescent marker that is used to detect neural activity. An ultrasound transducer 410 is coupled to the aCSF and introduces one or more low power ultrasound pulses 422 in an acoustic beam 420 directed onto the neural tissue slice 494. The slice is mounted a distance from the transducer that is indicated in FIG. 4 by the aCSF column 492. The setup includes a laser-scanning confocal imaging microscope 480 that views the neural tissue before, during and after ultrasound exposure to detect neural activity changes.

In some embodiments, a whole brain is mounted in the aCSF 490 in place of the slice 494. To determine the acoustic intensity impinging at the location of slice 494, in a calibration step performed in some embodiments of step 320, a hydrophone replaces the slice 494 while the transducer 410 is driven. The height of aCSF column 492 is adjusted in various embodiments. For example, in various embodiments, the height of column 492 was varied from 4.5 to 45 mm.

Figures 4B, 4C:
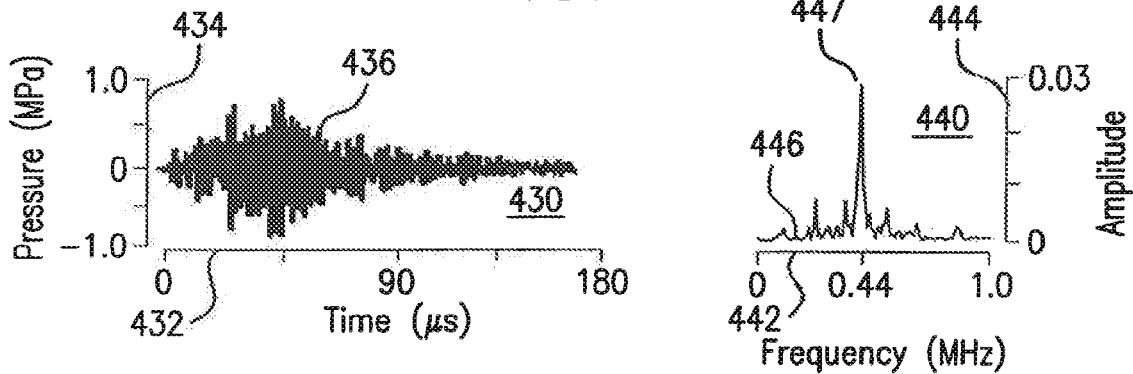
FIG. 4B shows a graph that illustrates an example acoustic signal received at a location of neural tissue.
FIG. 4C shows a graph that illustrates an example spectrum of the acoustic signal depicted in FIG. 4B.

FIG. 4B is a graph 430 that illustrates an example acoustic signal 436 received at a location of neural tissue, according to an embodiment, as measured by a hydrophone. The horizontal axis 432 indicates time in microseconds (μs, 1 μs=$10^{-6}$ seconds). The vertical axis 434 indicates pressure in MegaPascals (MPa, 1 MPa=$10^6$ Pascals=$10^6$ Newtons per square meter and is about ten time atmospheric pressure). The signal 436 was measured at height about 2 mm above transducer 410 which was driven at ultrasound frequency 0.44 MHz in a single pulse including 10 cycles and voltage range of 500 mV p-p pulses and further amplified using a 50 dB gain RF amplifier.

FIG. 4C is a graph 440 that illustrates an example spectrum 446 of the acoustic signal depicted in FIG. 4B, according to an embodiment. The horizontal axis 442 indicates frequency in MegaHertz. The vertical axis 444 indicates amplitude in arbitrary units. The spectrum 446 was computed from the pressure signal 436 using a digital Fast Fourier Transform (FFT), and contains one salient peak 447 at 0.44 MHz, the ultrasound driving frequency for transducer 410.

In several illustrated embodiments, an ultrasound waveform designated USW-1 consists of 250 ultrasound pulses, each pulse consisting of 10 square wave cycles at 0.44 MHz, for a pulse length of 22.7 microseconds. The pulse repeat frequency (PRF) ramps up over five seconds from PRF min=0 to PRF max=100 Hz (thus averaging 50 pulses a second over the first 5 seconds). The total waveform duration is therefore 5 seconds. The peak to peak square wave amplitude driving the transducer of the illustrated embodiment was 500 mV. The corresponding pulse average ultrasound intensity is 23 mW/cm².

According to an embodiment, histology can be used to observe modulated neural activity. For example, at the end of the waveform, 5 seconds after the start of modulation by USW-1, fluorescent emissions in CA1 SP and CA1 SR regions are greater than fluorescent emissions in the same regions at 2 seconds before modulation by ultrasound waveform. Such a histological comparison indicates significant modulation of neural activity by this ultrasound waveform at this low intensity.

Figure 5:
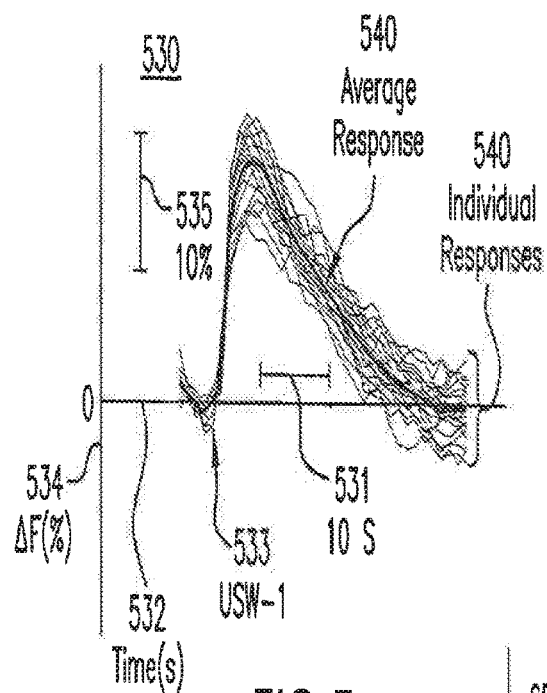
FIG. 5 shows a graph that illustrates example temporal response of neural activity after modulation.

FIG. 5 is a graph 530 that illustrates example temporal response of neural activity after modulation, according to an embodiment. The horizontal axis 532 is time in seconds; and the horizontal scale is given by segment 531 that corresponds to 10 seconds. The vertical axis 534 indicates ΔF in percent (%); and the vertical scale is given by segment 535 that corresponds to 10%. The start of USW-1 is indicated by tick 533. Individual responses after each ultrasound waveform are given by traces 540. A thick light curve 540 indicates the average temporal response. As can be seen in graph 530, the neural activity indicated by spH increases strongly during the five second duration of the ultrasound waveform up to almost 20%, and stays elevated, though at an ever diminishing level, for more than 10 seconds after the waveform ends. This indicates significant and persistent modulation of neural activity by this ultrasound waveform at this low intensity.

Figure 11:
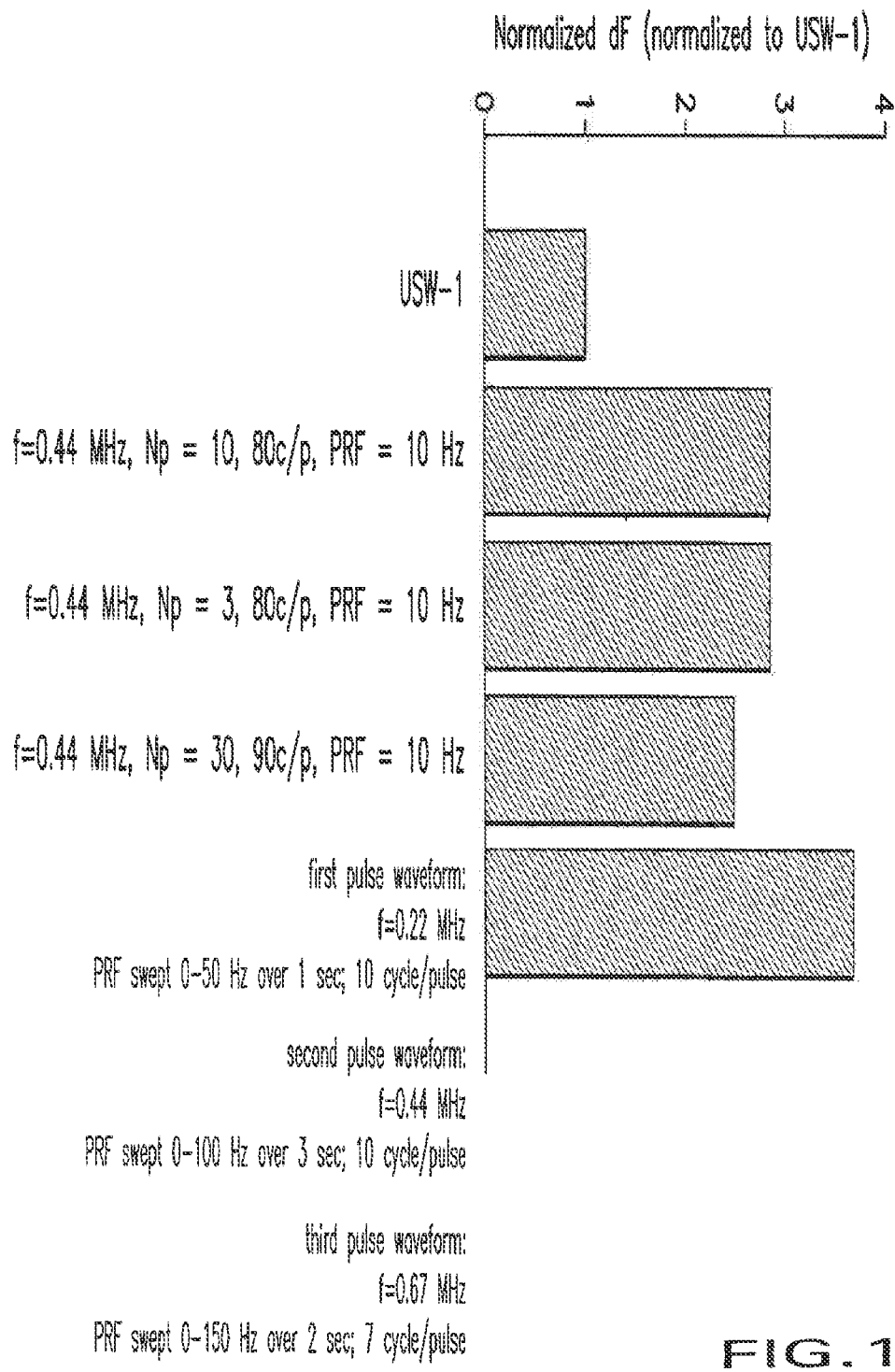
FIG. 11 shows a graph that illustrates example enhanced effects on neural activity by modulation with particular ultrasound waveforms.

FIG. 11 is a bar graph that illustrates example enhanced effects on neural activity by modulation with particular ultrasound waveforms, according to several embodiments. The horizontal axis indicates different low intensity waveforms, at intensities less than 500 mW/cm². The vertical axis indicates the mean peak ΔF obtained for many neurons in response to the waveform, normalized by the mean peak ΔF obtained from many neurons in response to USW-1.

Bar 1210 indicates the normalized ΔF for USW-1 and is equal to 1 by definition. Recall that USW-1 is characterized by f=0.44 MHz, c/p=10, Np=250, PRF=ramp (for a waveform duration of 5 seconds). Bar 1220 indicates the normalized ΔF for a waveform (called USW-1220 hereinafter) characterized by f=0.44 MHz, c/p=80, Np=10, PRF=10 Hz (for a waveform duration of 1 second). Bar 1230 indicates the normalized ΔF for a waveform (called USW-1230 hereinafter) characterized by f=0.44 MHz, c/p=80, Np=3, PRF=10 Hz (for a waveform duration of only 0.3 seconds). Bar 1240 indicates the normalized ΔF for a waveform (called USW-1240 hereinafter) characterized by f=0.44 MHz, c/p=80, Np=30, PRF=10 Hz (for a waveform duration of 3 seconds). Bar 1250 indicates the normalized ΔF for a composite waveform (called USW-1250 hereinafter) characterized by multiple ultrasound frequencies, cycles per pulse and pulse repeat frequencies, as described in more detail below.

USW-1 produces effects comparable to therapeutic effects produced by electrical stimulation from surgically implanted electrodes. As can be seen in graph 1200, several waveforms produce effects, about three times the effect of USW-1 and more, without the intrusion and danger of implanted electrodes.

The effects of USW-1220 and USW-1230 show that fewer pulses at the same frequency are effective. The effect of USW-1240 at the same ultrasound frequency but longer duration is slightly diminished, and the effect of USW-1 at the same frequency but even longer duration is substantially diminished, suggesting a saturation effect on particular cell membrane components affected by this ultrasound frequency.

To avoid such saturation, USW-1250 changes several aspects of the pulses. Specifically USW-1250 is characterized by f=0.22 MHz, c/p=10, Np=25, PRF=ramp from 0 to 50 Hz over 1 second; followed by f=0.44 MHz, c/p=10, Np=150, PRF=ramp from 0 to 100 Hz over 3 seconds; followed by f=0.67 MHz, c/p=7, Np=150, PRF=ramp from 0 to 150 Hz over 2 seconds (for a waveform duration of 6 seconds). USW-1250 produces nearly four times the effect of USW-1 and none of the saturation suggested by USW-1240 and USW-1.

Other waveforms with multiple pulse characteristics are effective in modulating neural activity and cellular activity. Another effective waveform is characterized by f=0.44 MHz, c/p=10 Np=10, PRF=1 Hz (for a duration of ten seconds). This waveform produced depression of neural activity in experiments.

The present invention comprises methods and devices for modulating cellular activity in a subject. Methods comprise providing ultrasound to a subject, for example, by the use of one or more low intensity, low frequency ultrasound and/or low intensity ultrasound transducers. For example, the ultrasound (US) transducer can be acoustically coupled to an external surface of a subject, or alternatively, the US transducer can be in an acoustically effective range of the target tissue, and the ultrasound transducer can then be driven to form stimulus waveforms in the tissue, cell, or organ with an intensity below about 900 milliWatts per square centimeter (mW/cm$^2$). The ultrasound waveforms may comprise one or multiple frequency components.

In an embodiment, driving the ultrasound transducer further comprises driving the ultrasound transducer to form pressure fluctuation waveform or a stimulus waveform including a plurality of pulses, each pulse of duration less than about 10000 microseconds (µs). Pulse duration may be variable depending on a particular method or device, and may have a duration of about 10 seconds or less, such as about 100 to 10000 microseconds. Driving the ultrasound transducer can further comprise driving the ultrasound transducers to form a pressure fluctuation waveform or a stimulus waveform with a plurality of pulses within a waveform duration that is less than about ten second (s). This comprises only one stimulus waveform and this waveform maybe repeated a nearly infinite number of times. As used herein, pressure fluctuation waveform and stimulus waveform are used interchangeably.

Driving the ultrasound transducer may further comprise driving the ultrasound transducers to form a stimulus waveform at a frequency above about 0.20 MHz. The waveform may be one or more of known waveforms arbitrary or not, including but not limited to, sine, square, sawtooth and triangle. The ultrasound waves may be focused to provide action at a particular site in or on the subject, or the waves may be unfocused and provide action at multiple sites. The waves may be continuous or pulsed, depending on the desired application. The frequency or intensity may be uniform throughout a treatment period, or may alternate or sweep from one number to another, and back to the original number. Those skilled in the art are able to determine such parameters for the desired application. Examples are disclosed herein.

The low-intensity, low-frequency ultrasound described herein can be used to stimulate cellular molecular pathways in cells, and for example, to cause them to (i) secrete signaling molecules (i.e., insulin from beta cells, BDNF, GDNF from neurons and glia, CCK from intestinal cells etc), (ii) increase cell proliferation, (iii) induce cell differentiation, (iv) modulate transcription, (v) modulate translation, or (vi) a combination thereof. These actions can involve a calcium-dependent process. For example, calcium can come from intracellular stores such as IP3, RyR and TRP, or from other membrane ion channels, such as voltage sensitive, mechanosensitive, and TRP channels.

The use of low-intensity, low-frequency ultrasound can activate calcium signaling pathways for the use of various therapies in various tissue/cell types (such beta cells in pancreas for treatment of diabetes, cardiac cells for treatment of heart disorders and others, as described herein). The action of the ultrasound described herein can function in both neural and non-neural cells to activate signaling pathways, and thereby have a therapeutic value. For treating traumatic brain injury, for example, methods comprise using ultrasound to stimulate the release of neuroprotective agents without causing cells to fire action potentials, although ultrasound may be used induce action potentials, if desired. For a treatment of diabetes, methods comprise providing ultrasound for the stimulation of insulin secretion (through direct actions on the beta cells or through neurostimulation of vagal efferents), as well as causing beta cells to proliferate by stimulating the pancreas directly with ultrasound.

The methods and devices of the present invention may modify the fluid dynamics of organs and fluids within organs, such as brain fluids and/or viscoelastic neuronal membranes, in a manner that increases or decreases neuronal activity. The ultrasound treatments of the present invention may modify channels to regulate ions, as well as fluid mechanics in a manner to then directly modify the activity of cells residing in the extracellular fluids or ultrasound waves may modify the fluid dynamics and membrane permeability of cells directly. Providing ultrasound waves to a target tissue may modify the fluid dynamics of that target tissue such that is affected. US may act on extracellular and intracellular fluids, as well as on cell membranes themselves, resulting in at least modifying the activity of cells.

Modulation of cellular activity by ultrasound may comprise a change in the secretion of signaling molecules, the proliferation of cells, the differentiation of cells, the modulation of protein transcription, the modulation of protein translation, modulation of protein phosphorylation, modulation of protein structure such as by changing the protein structure itself or through dimerization or other formation of protein multimers, activating caspases or other proteins, or a combination thereof. Such changes in cellular activity or activities may be detected in the cells themselves, in the results of such cellular changes on structures such as changes in nerve activity, or other physical changes such as altered insulin use or release by cells, restored brain activity or cessation of brain activity, or other physical parameters that may be measured for the treated subject. Methods for detecting cellular activity change are known to those skilled in the art. Such tests include tests from the molecular biological level to gross anatomical determinations, for example, DNA transcription rates, protein phosphorylation changes, and physiological determinations such as blood tests, hormone release and usage tests, nerve function tests, and subject reports of health, pain, cessation or increase of desires or drives.

An aspect of the present invention comprises modulating cellular activity, such as neural cells or other cells, by providing pulsed or continuous ultrasound waveforms having arbitrary or particular forms. A method of the present invention comprises modulating cellular activity in a non-invasive manner by transmitting specific sets of pulsed ultrasound (US) waveforms, for example, to intact neuronal circuits. Though not wishing to be bound by any particular theory, it is currently believed that spatiotemporal pattern(s) of the US energy itself, as well as its actions on a neuronal circuit may be related to modulating neuronal activity. The pulse sequence(s) delivered to the tissue may be related to successful stimulation/inhibition of neuronal activity. The present invention comprises methods and devices for modulation of cells, including neuronal cells, in brain slices, whole ex vivo brains, and intact brain circuits. Such methods and devices may comprise different ultrasound transducer types, and may be acquired from different manufacturers, for example, Array Therapeutic, LLC, Olympus NDT/Panametrics, and Ultran. The effects of the treatments and methods described herein are not dependent on the device, equipment, or brain preparation, but on the ultrasound delivery.

An aspect of the present invention comprises in vivo use of US pulses having lower pulse intensity integrals when compared to those used in vitro. To achieve a temporal average intensity similar to those used in vitro, US pulses were delivered to intact brain with a higher pulse repetition frequency than those used in vitro. Intensities ranging from about 0.0001 to 900 mW/cm$^2$ with frequencies (single or multiple-component; see FIGS. 27 and 28) ranging from about 0.1 to 0.9 MHz are effective for modulating neuronal activity. An aspect of the invention comprises using temporal average intensity ($I_{TA}$) for US pulses of greater than 20 mW/cm$^2$, and about 50 mW/cm$^2$ at the cellular site, are useful for stimulating neuronal activity. An aspect of the invention comprises using intensity values less than about 100 W/cm$^2$ and frequencies less than about 0.9 MHz occurring at the neural circuit being targeted for modulating neuronal activity in the intact brain of an organism.

The present invention comprises use of low-intensity, low-frequency pulsed ultrasound for affecting modulation of cells. US may be provided alone or with other agents. Such other agents may be provided to the subject before, during or after US exposure. Such agents include, but are not limited to, exogenous genes, chemicals, proteins, pharmaceuticals, gases, antibiotics, substrate molecules, ionic molecules, or other active agents.

Pulsed US waveforms useful for modulating cellular activity such as neuronal activity may be created using different methods. For example, neuronal circuits can be excited in a clear and robust manner using pulsed ultrasound having <0.9 and >0.2 MHz. For example, it has been found that a continuous wave of US at a frequencies 0.2 to 0.9 MHz do not produce neuronal stimulation, but rather inhibition of activity such that no responses are obtained. An aspect of the invention comprises using US in a specific set of pulse sequences for the stimulation of neuronal activity within that frequency range. The US may be delivered in focused ultrasound pulses, or may be delivered as collimated or unfocused planar waves. Such ultrasound waves may be delivered using single ultrasound components, such as a transducer, or from 1 to 299 transducers, and some component devices may contain up to 1000 transducers for focusing and resolution control.

An aspect of the present invention comprises stimulating brain activity, or other cellular modulation, by using US waveforms constructed of distinct US pulses (from 1 to 50,000 cycles) having a particular frequency and then alternating the length and frequency of US pulses so that the entire stimulus waveform is composed of US pulses having varying fundamental frequencies and durations. Though not wishing to be bound by any particular theory, it is currently believed that by alternating the frequencies of US within a stimulus waveform it keeps the neuronal membrane and its environment from adapting to acoustic pressure changes, which then permits more effective and robust modulation compared to US waveforms composed of a single fundamental frequency.

For example, methods of the present invention for intact brain circuits, in vivo, used ultrasound PZT transducers (manufactured by Ultran and/or Olympus NDT/Panametrics), with a mean optimal resonant center frequency of 0.5 MHz. To create US stimulus waveforms which had multiple frequency components, transducers were driven at a fundamental frequency off of the center frequency using square-wave voltage pulses, which produced US stimulus waveforms having various beat frequencies and harmonic frequencies.

The present invention contemplates US pulses as shown in FIGS. 27 and 28, which may be driven using 10 cycle voltage pulses, but that the number of voltage cycles driving transducers can range from 1 to 50,000 or higher. The number of US pulses per US waveform may similarly range from 1 to 10000000 repeated at pulse repetition frequencies from 0.0001 to 100 MHz for a total stimulus waveforms duration from about 0.000001 sec to a continuous application of the stimulus wave.

Figure 27A:
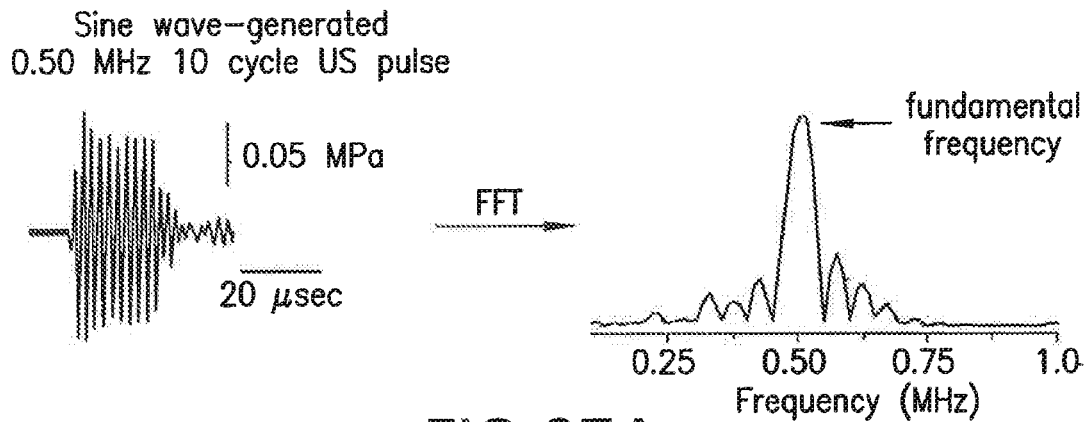
FIG. 27A shows an illustration of 10 cycles of a sine wave-generated ultrasound pulse at 0.50 MHz.
Figure 27B:
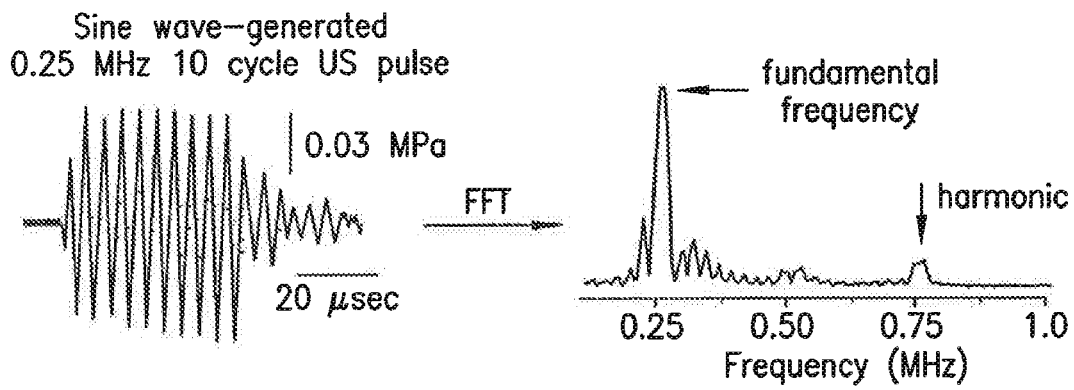
FIG. 27B shows an illustration of 10 cycles of a sine wave-generated ultrasound pulse at 0.25 MHz.
Figure 27C:
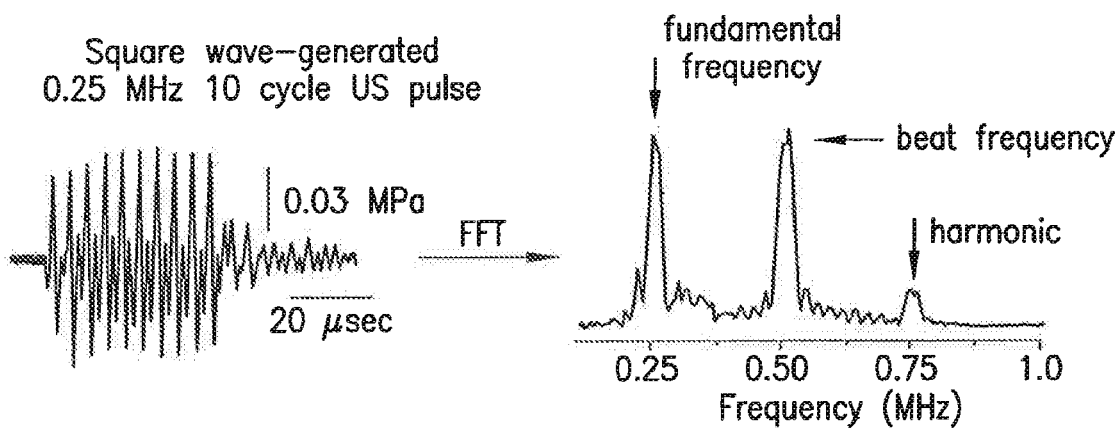
FIG. 27C shows an illustration of 10 cycles of a square wave-generated ultrasound pulse at 0.25 MHz.

FIG. 27A illustrates a 10 cycle US pulse generated using a 0.5 MHz 10 cycle sine wave voltage pulse delivered to the transducer. The transducer has a center frequency of 0.5 MHz. The FFT power spectrum (right) of this waveform, shows a single peak representing the fundamental frequency of 0.5 MHz. FIG. 27B similarly illustrates a 10 cycle US pulse generated using a 0.25 MHz 10 cycle sine wave pulse delivered to the same transducer. The FFT power spectrum at right a peak corresponding to the fundamental frequency (0.25 MHz), as well as the harmonic (0.75 MHz) is observed. Driving the transducer off its center frequency introduces off-resonant energy. US stimulus waveforms composed of mixed frequency components appeared may be effective for many applications of the methods and devices of the present invention. For example, transducers using square waves at fundamental frequencies off of their center frequency are shown in FIG. 27C. FIG. 27C illustrates a 10 cycle US pulse generated using a 0.25 MHz 10 cycle square wave pulse delivered to the same transducer as above. The FFT power spectrum, at right, has a peak corresponding to the fundamental frequency (0.25 MHz), as well as a beat frequency (0.5 MHz) and the harmonic (0.75 MHz) can be observed. Thus the US pulse itself introduces multiple frequency components.

The present invention contemplates methods comprising ultrasound pulses composed of a fundamental frequency, and alternating with US pulses having different fundamental frequencies. The present invention contemplates methods comprising US pulses composed of multiple frequencies in a stimulus waveform by generating US pulses having different frequency components rather than only the fundamental frequency. For example, the same US pulse may be repeated across time at some pulse repetition frequency, rather than delivering different pulses composed of different fundamental frequencies. Driving the transducers with a square wave having a fundamental frequency matched to the center frequency does not produce the type of effect as illustrated in FIG. 27C. An aspect of the invention comprises methods wherein square waves are used, but the transducers are driven very close to their center frequency, for example where the transducer has two peak frequencies 0.44 and 0.67 MHz. Pulse sequences as illustrated in FIG. 27D result, but at different frequencies more closely matching the optimal resonant frequencies of those transducers (0.44 and 0.67 MHz). The present invention contemplates multiple ways that are useful for creating specific pulse sequences, each of which are effective for modulating cellular activity, such as stimulating neuronal activity, depending on the desired outcome.

FIGS. 28A-F illustrates how different pulse sequences can be generated to use ultrasound for the purposes of modulating cellular activity. In FIGS. 28A-F, each segment illustrates 3 US pulses repeated at some pulse repetition frequency (PRF). Each pulse may contain between 1 and 50,000 or higher US cycles per pulse (c/p) driven by a sine wave, square wave, saw-tooth pattern, or arbitrary waveform to produce a fundamental frequency of 0.1 to 0.9 MHz with or without other beat and/or harmonic frequencies ranging from 0.02 to 100 MHz. The number of US pulses per US waveform may similarly range from 1 to 10,000,000 repeated at pulse repetition frequencies from 0.0001 to 100 MHz for total stimulus waveforms duration from about 0.00001 sec to a continuous application to the subject. FIG. 28A illustrates a US waveform having three pulses of US with each pulse having 10 US cycles produced using a 0.5 MHz sine wave and a 0.5 MHz transducer. FIG. 28B illustrates a US waveform having three pulses of US with each pulse having 10 US cycles produced using a 0.25 MHz sine wave and a 0.5 MHz transducer. FIG. 28C illustrates US pulses used in creating the US stimulus waveform introducing multiple frequency components in the waveform as previously discussed (FIG. 27C above). The waveform illustrated has three pulses of US with each pulse produced using a 0.25 MHz square wave and a 0.5 MHz transducer. FIG. 28D-E illustrate similar method outcomes for creating US stimulus waveforms, which use multiple US frequencies to achieve modulation of cellular activity such as neuronal activity. The US stimulus waveforms illustrated in FIG. 28D use square waves to drive the transducers very near the transducers optimal resonant frequencies. An aspect of the present invention comprises use of frequencies (i.e., 0.25 MHz farther away from center frequency of the transducers, when the center frequency equals 0.5 MHz) for modulating neuronal activity. Square waves, sine waves, and/or arbitrary waves may be used to drive the transducers.

Though not wishing to be bound by a particular theory, it is currently thought that ultrasound modulation of activity of cells or tissues may occur by changing the membranes of cells such as altering the activity of ion channels or ion transporter activity. Additionally, ultrasound modulation of activity of cells or tissues may occur by alterations of structures surrounding cells that then lead to alterations of cellular activity. These concepts, and others, are encompassed in the present invention's contemplations of modulation of activity or activities of cells. For example, application of ultrasound may modify the fluid dynamics of brain fluids and/or viscoelastic neuronal membranes in a manner that increases or decreases neuronal activity. Ultrasound will modify channels to regulate ions, as well as fluid mechanics in a manner to then directly modify the activity of cells residing in the extracellular fluids.

An aspect of the present invention comprises methods, devices and systems for modulating cellular activity wherein an algorithm is used in a closed- or open-loop manner to evaluate feedback of cellular, tissue or organ activity, such as brain activity or hormone release or use, and then modifying the stimulus waveform and treatment of the cells, tissue, organ or subject, based on the feedback. Use of open or closed loop feedback devices or systems are contemplated by the present invention.

An aspect of the present invention comprises methods, devices and systems for modulating cellular activity wherein light emitting devices are used. For example, in a continuous wave or pulsed ultrasound treatment, in which certain types of imaging and/or modulation of cellular activity is desired, a light energy emitting source, such as a LASER, LED or OLED, may be used. Ultrasound treatments may be used in combination with light treatment methods to modulate cellular activity. Such light treatment methods for modulating cellular activity may comprise an active agent, such as pharmaceutical or exogenous gene product or protein or chemical compound activity present in a subject, and are known to those skilled in the art and may be incorporated in the present invention. For example, light emitting devices may be used for photoactivation of compounds, or light modulation of cellular activity using exogenous proteins such as channel rhodopsin-2, or laser ablation therapies. Such light treatment methods may be provided concurrently with ultrasound waves, subsequently to ultrasound waves, or prior to ultrasound wave treatment. Such light therapy or light treatment methods may comprise light sources, including but not limited to, LASER, LED and OLED, may use pulsed or continuous light waveforms.

The methods, devices and systems of the present invention for modulation of cellular activity by applying ultrasound waves to a subject may be used in conjunction with or as an adjunct to other treatments to the subject. For example, low intensity or high intensity ultrasound waves may be used for imaging methods that generate data about the structure of a subject that are used as a map or to provide other information that is helpful when providing ultrasound stimulus waveforms for modulation of cellular activity in that subject. Ultrasound stimulus waveforms may be provided prior to, concurrently with, or after other treatment regimens. For example, when a subject is undergoing brain surgery using standard surgical techniques, ultrasound imaging as described herein, or ultrasound stimulus waveforms as described herein may be used before, during or after one or more surgical techniques. For example, in a diabetic subject who is using constant glucose monitoring devices, which may or may not be monitoring glucose but are referred to glucose monitoring devices, and/or an insulin pump, may also undergo ultrasound stimulus waveform treatment continuously, or in an intermittent, or regular treatment regimen of ultrasound. For example, a subject undergoing pharmaceutical or chemical treatment of a condition, such as cancer, for example, a subject with a brain tumor, wherein chemotherapy is being administered, may also undergo ultrasound treatments as described herein, prior to concurrently with or after each dosage of chemotherapy or each chemotherapy cycle, or the entire chemotherapy treatment regimen.

Methods and Devices for Eliminating Brain Tumor Tissue Using Low-Intensity, Low-Frequency Ultrasound The present invention comprises methods of treating a subject with a brain tumor using the ultrasound devices disclosed herein. A "brain tumor" is understood to be an abnormal growth of cells within the brain or inside the skull, which can be cancerous or non-cancerous (benign). It may be any intracranial tumor created by abnormal and uncontrolled cell division, normally either in the brain itself involving neurons, glial cells, astrocytes, oligodendrocytes, ependymal cells, lymphatic tissue, blood vessels; in the cranial nerves (myelin-producing Schwann cells), in the brain membranes (meninges), skull, pituitary and pineal gland, or spread from cancers primarily located in other organs (metastatic tumors). Types of brain tumors include, but are not limited to, glioma, astrocytoma, meningioma and blastoma.

For treatment of brain tumors, low-intensity, low-frequency ultrasound includes acoustic intensities ranging from about 0.1 mW/cm$^2$ to 100 W/cm$^2$ which are generated in the treatment region of the brain tumor tissue. Here, low-intensity, low-frequency ultrasound includes a range of ultrasound acoustic frequencies spanning from about 0.02 MHz to about 10.0 MHz and ranges therein. An aspect of the invention comprises methods for providing low intensity ultrasound to treat the brain, and methods for low intensity, low frequency ultrasound that will cross the skull bones to transmit ultrasound to the brain to treat the brain tumor.

Ultrasound waves may be applied in a pulsed or continuous manner. Ultrasound may be focused in the brain tumor treatment region using data acquired with medical imaging techniques such as MRI (magnetic resonance imaging), CT (computed tomography), PET (positron emission tomography), or sonography including acoustic radiation force imaging. Alternatively, ultrasound may be applied to the brain tumor treatment region in an unfocused manner. The ultrasound can be applied to the brain tumor treatment region such that the ultrasound energy acts on brain tumor cells in a manner to induce cell-death and/or apoptosis in the brain tumor cells in the absence of a deleterious increase in temperature. The outer skin and skull may be cooled to prevent temperature damage, if any. For example, ultrasound methods of the present invention comprise temperature changes where the brain and/or brain tumor tissue (excluding skull) temperature does create thermal lesions in the brain, where the temperature of the brain tissue does not exceed 44° C., or may be 35, 36, 37, 38, 39, 40, 41, 42, 43, 44° C. for more than 2, 3, 4, 5, 6, 7, 8, 9, 10, 11, 12, 13, 14, 15, 16, 17, 18, 19, or 20 seconds at any point during the treatment. In one example, the temperature in the brain remains between 30° C. and 44° C. during the delivery of ultrasound to the brain tumor treatment region. In a more specific example, the temperature does in the brain does not exceed more than 44° C. for more than 10 seconds during treatment.

It is known that the heating of diseased tissue induces coagulative necrosis and thus destroys the brain tumor cells. High temperatures may also be generated in surrounding tissues such as vasculature, skull, or normal brain tissue, which poses a patient being treated to unnecessary medical risks. Thus, increasing the temperature of brain tumors by delivering high-intensity ultrasound to destroy them may inadvertently damage surrounding cranial nerves (i.e., the optic nerve near the skull base), the vasculature (near the cranium and/or skull base), or normal brain tissue. Methods may include combination therapies where low intensity, low frequency ultrasound methods are used to induce cell death by activation of cells leading to activation of cell death pathways, and application of high frequency ultrasound that provides high temperatures to the tissue for ablation and/or cell death due to high temperatures.

Ultrasound induced cell modulation or activation may comprise activation of cell death pathways including the activation of caspases and/or other cytotoxic proteins (the so called death enzymes) by ultrasound-induced modulation of ion channels or ion transporters, which act to regulate the ion conductance and/or transport of calcium, potassium, chloride, or sodium across the cell membrane or across the membrane of cellular organelles such as mitochondria, nuclei, and endoplasmic reticulum found in brain tumor cells.

Brain tumors consist of numerous different histopathological brain cell types. Brain tumors can be cellular identified as originating primarily from glial cells including astrocytes and oligodendrocytes, neuroblasts, or other cell type found in brain tissues. The cell types making up brain tumors have many fundamental differences, however all these cell types can be subjected to cell death and/or apoptosis, which is activated by various molecular cellular signaling cascades including activation of caspase proteins and/or other cytotoxic proteins.

It is currently believed that using low-intensity, low-frequency ultrasound reduces the risk of damaging normal brain tissue due to either thermal effects and/or cavitational effects. Treating brain tumors using low-intensity, low-frequency ultrasound reduces the probability of increasing the temperature of either the brain tumor treatment region or the surrounding tissues (cranial nerves, vasculature, and bone). Treating brain tumors using low-intensity ultrasound as described herein reduces the probability of inducing cavitation in brain tissue. The intensities currently described for treating brain tumors by inducing coagulative necrosis through thermal mechanisms while transmitting ultrasound through the intact skull are typically >100 W/cm$^2$. These high acoustic intensities and associated acoustic pressures can cause undesirable thermal and/or cavitational damage to normal brain tissue. The probability of inducing cavitation in brain tissue is also greatly reduced at acoustic intensities <100 W/cm$^2$ whereby peak acoustic pressures are <10 MPa.

The present invention comprises methods and devices for transmitting low-intensity, low-frequency ultrasound in a range from about 0.1 mW/cm$^2$ to about 100 W/cm$^2$ to a brain tumor treatment region, through the skull or to exposed tissue, in a focused or unfocused manner. The intensity of ultrasound refers to the intensity generated during the delivery of a single treatment event or ultrasound transmission event (pulsed or continuous wave).

The present invention comprises methods and devices for transmitting low-intensity ultrasound to a brain tumor treatment region, through the skull or to exposed tissue, through intact or craniotomized skull, in a continuous wave or pulsed manner ranging in duration from 0.000001 seconds to 100,000 seconds during the delivery of any one ultrasound treatment event (a single ultrasound transmission event). An ultrasound treatment event may be repeated at repetition frequencies ranging from once about every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 60, 100, 120, 150, 180, 200, 240, 280, or 360 days, or more. In one example, treatment is given every 30 days up to 10 KHz for a total cumulative ultrasound treatment event time not to exceed 94,700,000 seconds (~3 years) using any repetition frequency or a combination of repetition frequencies in either single or multiple treatment sessions.

The present invention comprises methods and devices for transmitting low-intensity ultrasound where the ultrasound applied to a brain tumor treatment region induces peak acoustic pressures in the brain treatment tumor region is less than 5, 6, 7, 8, 9, 10, 11, 12, 13, 14, or 15 MPa, for example. In one embodiment, the peak acoustic pressure is less than 10 MPa.

The present invention comprises methods and devices for transmitting low-intensity ultrasound to a brain tumor treatment region in which the acoustic frequencies of ultrasound delivered to the brain tumor region represent a single or combination of acoustic frequencies ranging minimally from about 0.05 to 10 MHz.

The present invention comprises methods and devices composed of 1 to 1000 ultrasound transducer elements where plate voltages are applied to the ultrasound transducer elements using analog or digitized waveforms composed singly or as a combination of square, sine, saw-tooth, or arbitrary waveforms while the transducers are activated in a synchronized or phased manner. In an embodiment, the number of ultrasound transducer elements is less than 300.

Low-intensity ultrasound can be administered to a brain tumor treatment region whereby the action of ultrasound alone induce cell death and/or apoptosis in brain tumor cells by activating cellular molecular signaling proteins such as caspases by modulating the ionic conductance or transport of any of the following ions calcium, potassium, sodium, and chloride in tumor cells by regulating the activity of endogenous protein ion channels or ion transporters on the tumor cell membrane or the membrane of organelles found in the brain tumor cell such as the nucleus, mitochondria, or endoplasmic reticulum.

The methods disclosed herein can be administered alone, or in combination with other devices, compositions, or methods for use in treating brain tumors, other tumors, or cell death in particular cells. The present invention comprises methods and compositions which can enhance the effectiveness of the ultrasound treatment or may be used to augment brain tumor treatment without a specific facilitation of the ultrasound effect. For example, the methods of use of ultrasound taught herein may be combined with compositions comprising recombinant proteins or small organic molecules to induce cell death and/or apoptosis in brain tumor cells or other tumors or cell types by activating cellular molecular signaling proteins such as caspases by modulating the ionic conductance or transport of any of the following ions: calcium, potassium, sodium, and chloride in tumor cells by regulating the activity of endogenous protein ion channels or ion transporters on the cell membrane or the membrane of organelles found in the brain tumor cell such as the nucleus, mitochondria, or endoplasmic reticulum.

Data from medical imaging modalities can be used to focus the ultrasonic energy, including but not limited to, ultrasound imaging, acoustic radiation force imaging, photoacoustictomography, MRI, CT, PET, or a combination thereof. These can be used before, during, or after ultrasound treatment as described herein.

Methods and Device for Treating Diabetes Using Low-Intensity, Low-Frequency Ultrasound "Diabetes" as used herein refers to both Type I and Type II diabetes mellitus. It is currently believed that the vagus nerve plays an integral role in regulating nutrient metabolism and physiological homeostasis by innervating the stomach, intestines, pancreas, and liver. Ascending vagal afferents from these organs transmit information regarding nutrients and food intake to the hypothalamus and other brain regions while descending vagal efferents serve to carry signals from the hypothalamus and brain back to the stomach, intestines, pancreas, and liver to govern the synthesis and secretion of metabolic factors such as insulin, glucagon, and others. This gut-brain-gut loop is referred to as the vago-vagal loop. In the vago-vagal loop, vagal efferent activity is triggered by nutrient consumption (fat, carbohydrate, and/or protein) as receptors in the oropharyngeal cavity, stomach, and small intestines sense the intake of these nutrients. In response to nutrient intake and glucose buildup the activity of vagal efferents innervating the pancreas stimulate early-phase insulin release as well as serve to optimize postprandial insulin synthesis and secretion by the β-cells of pancreatic islets. Diabetes is a metabolic disease characterized either by pathologically low-levels of insulin synthesis and/or secretion in response to glucose buildup (Type-I Diabetes or Juvenile Diabetes) or by abnormal cellular responses to synthesized and/or secreted insulin (Type-II Diabetes or Adult-Onset Diabetes).

Electrical stimulation of vagal efferents is known to stimulate the synthesis and secretion of insulin from the β-cells of pancreatic islets. The present invention comprises methods and devices for treating diabetes by stimulating the activity of vagal efferents and/or cells in gastrointestinal, nervous or related organs using low intensity ultrasound. Low-intensity ultrasound may increase the activity of nervous tissues by inducing action potentials and neurotransmitter release. In one embodiment, the invention comprises a method and a device by which low-intensity ultrasound is delivered in a focused or unfocused manner to vagal afferents and or efferents in an effective manner to increase activity of vagal afferents and or efferents and in a manner sufficient so that insulin synthesis and/or secretion by the β-cells of pancreatic islets in diabetics is stimulated.

The present invention comprises methods and devices for the treatment of diabetes by which low-intensity ultrasound is delivered in a focused or unfocused manner directly to the pancreas in a manner to stimulate proliferation (division) of pancreatic β-cells to promote insulin production/secretion and/or to stimulate the production/secretion of insulin by existing pancreatic β-cells.

In these embodiments low-intensity ultrasound is used for stimulating the vagus nerve to stimulate pancreatic β-cell activity or by delivering low-intensity ultrasound directly to the pancreas itself in a manner to stimulate β-cell activity or by combining both approaches in conjunction with one another. The methods are designated for delivering low-intensity ultrasound in a manner to promote insulin secretion by pancreatic β-cells by at a minimum increasing the calcium concentration in the β-cells. Low-intensity ultrasound can increase the calcium concentration in many cell types including in neurons to modulate neurotransmitter release as previously shown. Increasing calcium concentrations and calcium activity in β-cells using low-intensity ultrasound will stimulate the physiological activity of the β-cells such that these cells either undergo division to increase their cellular density to promote increased insulin production and/or secretion or such that the increase in calcium stimulates the production and/or secretion of insulin from existing β-cells.

Figure 13:
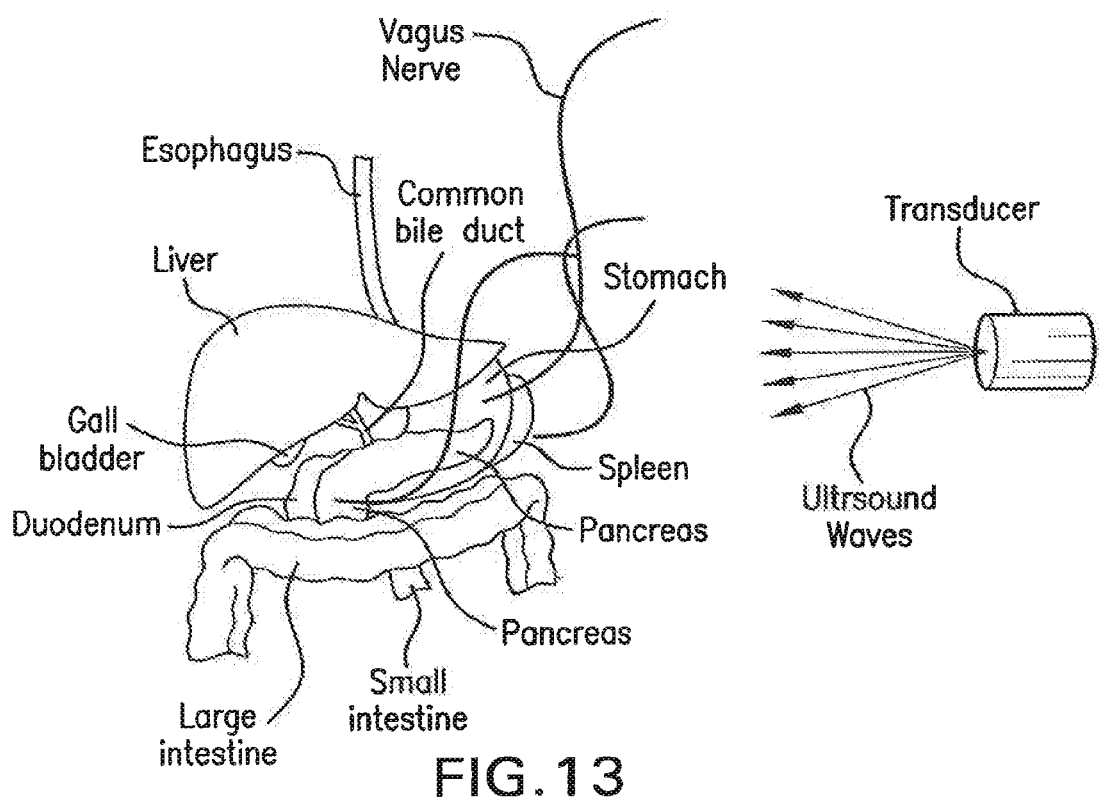
FIG. 13 shows a drawing of methods of the present invention for stimulating the vagus nerve efferents to stimulate insulin synthesis and/or pancreatic secretions and/or activating β cells or other cells of the pancreas.
Figure 14:
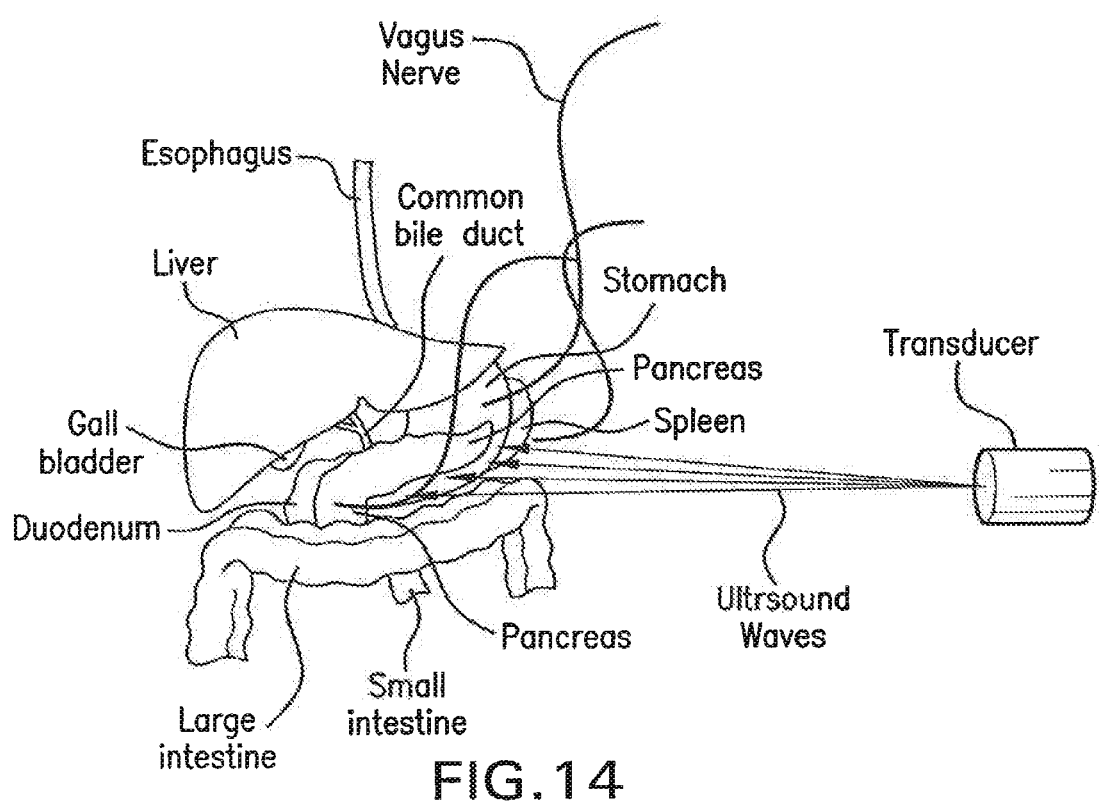
FIG. 14 shows a drawing of methods of the present invention for direct stimulation of the pancreas and its cells to stimulate insulin synthesis and/or pancreatic secretions and/or activating β cells or other cells of the pancreas. Such a method may be used alone or in conjunction with stimulation of the vagal nerve.

Ultrasound treatments and methods of the present invention may comprise use of other devices, such as those used for blood glucose monitoring or insulin level detectors. Such devices may provide feedback information to ultrasound devices so that ultrasound devices comprising transducers may provide ultrasound, or increase or decrease ultrasound treatments in response to such feedback information. The present invention contemplates control of ultrasound transducers by feedback devices, and includes devices capable of measuring a body parameter, transmitting that information to an ultrasound producing device to alter or maintain the ultrasound treatment provided, and includes applications for conditions known by those skilled in the art and those disclosed herein. Examples of aspects of methods and devices for diabetes treatment are shown in FIGS. 13-14. In FIG. 13, the vagus nerve, with afferents to the brain and efferents to multiple organs, for example, the gastrointestinal tract and related organs. An ultrasound transducer, comprising from 1 to 1000 elements, for providing low intensity ultrasound is shown providing ultrasound waves to efferents of the vagus nerve. The ultrasound modulates the activity of the vagus nerve and the vagus nerve stimulates the pancreas to cause synthesis of insulin, secretion or insulin or other cellular factors produced by the pancreas. Low intensity ultrasound activates the vago-vagal reflex innervating the pancreas, which in turn activates at least β-cells. The low intensity ultrasound may be focused or unfocused. In FIG. 14, low intensity ultrasound is shown activating the pancreas directly. The methods of FIG. 13, activation of the vagal efferents and the methods of FIG. 14, direct activation of the pancreas, may be used in combination, sequentially or simultaneously. In FIG. 14, an ultrasound transducer, comprising from 1 to 1000 elements, for providing low intensity ultrasound is shown providing ultrasound waves to the pancreas to stimulate β-cell insulin synthesis, secretion of insulin, and/or β-cell division and proliferation. As is known, other cell types are present in the pancreas and these cells may or may not be stimulated, depending on the desired treatment. The low intensity ultrasound may be focused or unfocused. The number of transducers may be 1 to 1000, and may have a mixed range of frequencies. The frequencies of the transducers used may be in a simple design, such that all frequency ranges are the same, or may be in a complex design, in which different transducers have different frequency ranges. For example, one transducer may be at 0.5 MHz, the adjacent transducer at 0.7 MHz, and the adjacent transducer at 0.5 MHz. The transducers may be physically arranged in any known functional design, such as sequentially along a line, or spatially arranged in two or three dimensions to provide unique devices.

The present invention comprises methods and devices for stimulating the vagus nerve using low-intensity ultrasound (0.001 mW/cm$^2$ to 100 W/cm$^2$; focused or unfocused) in a manner which triggers the β-cells of pancreatic islets to increase insulin synthesis and/or insulin secretion to treat diabetes. The intensity of ultrasound refers to the intensity generated at the vagus nerve during the delivery of a single treatment event. Low-intensity ultrasound can be transmitted to the vagus nerve and/or the pancreas in a continuous wave or pulsed manner ranging in duration from 0.000001 seconds to 100,000 seconds during the delivery of any one ultrasound treatment event (a single ultrasound transmission event). An ultrasound treatment event may be repeated at repetition frequencies ranging from once about every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 60, 100, 120, 150, 180, 200, 240, 280, or 360 days, or more. In one example, treatment is given every 30 days up to 10 KHz for a total cumulative ultrasound treatment not to exceed the life of the patient being treated.

The present invention comprises methods and devices for stimulating cell division of the β-cells of pancreatic islets by focusing low-intensity ultrasound directly on the pancreas to treat diabetes. Also disclosed are methods for stimulating insulin synthesis in β-cells of pancreatic islets by focusing low-intensity ultrasound directly on the pancreas to treat diabetes. Further disclosed are methods for stimulating insulin secretion by the β-cells of pancreatic islets by focusing low-intensity ultrasound directly on the pancreas to treat diabetes.

The present invention comprises methods and devices for treatment of diabetes whereby the actions of ultrasound alone induce insulin synthesis and/or secretion by increasing the calcium concentration in β-cells of pancreatic islets. The present invention comprises methods and devices for transmitting low-intensity ultrasound to the vagus nerve and/or pancreas for the treatment of diabetes whereby the actions of ultrasound in conjunction with recombinant proteins and/or small organic molecules induce insulin synthesis and/or secretion by increasing the calcium concentration in β-cells of pancreatic islets.

The present invention comprises methods and devices for transmitting low-intensity ultrasound to the vagus nerve and/or the pancreas for the treatment of diabetes in which the acoustic frequencies of ultrasound delivered to the pancreas represent a single or combination of acoustic frequencies ranging minimally from 0.05 to 50 MHz. In one embodiment a single or multiple transducers is externally coupled to the patient. In another embodiment a single or multiple transducers is surgically implanted. In another embodiment, the activation of ultrasound transducers is controlled by a device for sensing glucose levels. In the present invention, one or more transducers may be implanted or permanently or semi-permanently attached to a body or surface by methods known to those skilled in the art, such as by sutures or bolts, such as titanium or titanium alloy bolts. Such attachment elements are known to those skilled in the art, and are not limiting to the invention.

Methods and Device for Treating Obese or Overweight Individuals Using Low-Intensity, Low-Frequency Ultrasound It is currently believed that the vagus nerve plays an integral role in regulating satiety, food intake, body weight, glucose levels, fat metabolism, and nutrient homeostasis by innervating the stomach, intestines, pancreas, and liver. Along the gut-brain axis in the vago-vagal loop ascending vagal afferents from these organs transmit information regarding nutrients and food intake to the hypothalamus and other brain regions while descending vagal efferents serve to carry signals from the hypothalamus and brain back to the stomach, intestines, pancreas, and liver to govern gastric/intestinal motility and function, as well as the synthesis and secretion of gastrointestinal hormones and metabolic factors such as cholecystokinin, peptide YY, ghrelin, glucagon-like peptide, gastric inhibitory polypeptide, and enterostatin which all regulate to varying degrees appetite, food-intake, and satiety.

Malfunctioning signaling in the vago-vagal loop can lead to obesity since many of the hormonal cues eliciting meal termination do not function properly. Further, obesity can occur when the vagus nerve cannot act in an appropriate manner to regulate fat metabolism or glucose levels. Vagal afferents undergo an increase in activity during meal consumption as receptors in the oropharyngeal cavity, stomach, and small intestines sense the intake of nutrients including fats, carbohydrates, and proteins. These afferents trigger the release of local satiety cues and transmit signals to various regions of the hypothalamus, which in turn leads to an increase in the activity of vagal efferents innervating the stomach, small intestines, liver, and pancreas to regulate gastric delay, gastric motility, various gastrointestinal hormones (described above) which trigger satiety and meal termination, and the production and release of metabolic enzymes such as insulin. The overall net effect of increased vagal afferent and efferent activity during nutrient consumption acts to signal satiety and regulate postprandial fat and glucose metabolism.

The present invention comprises methods and devices for delivering focused or unfocused low-intensity, low-frequency ultrasound to the vagus nerve or the stomach, duodenum, jejunum, liver, or pancreas, or more than one, sequentially or concurrently, prior to, during, and/or shortly following nutrient consumption and/or food intake for the treatment of obese or overweight individuals.

The present invention comprises methods and devices for low-intensity ultrasound that are used to increase the activity of vagal nerves (afferent or efferent) to induce satiety in individuals who are obese and/or overweight (overweight is defined herein as an individual with a BMI greater than about 25 kg/m$^2$ and obesity is an individual with a BMI greater than about 30 kg/m$^2$), engage in compulsive overeating or binge eating disorders, and/or who have abnormal fat or glucose metabolism disorders. For example, low intensity ultrasound is delivered in a focused or unfocused manner to the vagus nerve in a manner that reduces the average caloric intake per nutrient consumption event (meal or snack). Low intensity ultrasound is applied to the vagus nerve in a manner to increase neuronal activity beginning 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60, 90, or 120 minutes prior to the time when a nutrient consumption event including food intake occurs. In one example, the ultrasound is applied 30 minutes prior to food or nutrient intake. The ultrasound treatment can last during and following nutrient consumption for 0, 1, 2, 3, 4, 5, 6, 7, 8, 9, 10, 11, 12, 13, 14, 15, 16, 17, 18, 19, 20 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 51, 52, 53, 54, 55, 56, 57, 58, 59, or 60, 90, or 120 minutes. In one example, ultrasound treatment is continued for 60 minutes after food or nutrient consumption. Low intensity ultrasound application is applied to the vagus nerve in a manner to increase the activity of vagal afferents transmitting signals to the arcuate nucleus and the nucleus solitary tract of the CNS for the purposes of eliciting satiety and/or increased fat and/or glucose metabolism.

The present invention comprises methods and devices for low-intensity, low-frequency ultrasound delivery in a focused or unfocused manner to any of anatomical regions of any of the following gastrointestinal organs: stomach, duodenum, jejunum, liver, and pancreas. An aspect of the invention comprises delivery of low-intensity ultrasound to all or parts of these organs in focused or unfocused fields or to portions of the vagus nerve innervating them for the purposes of eliciting satiety or increasing the production or release of gastrointestinal hormones or to stimulate fat or glucose metabolism (or more than one of those purposes combined) for the treatment of obese or overweight individuals. In this embodiment, the actions of low-intensity ultrasound acts directly on the stomach, duodenum, jejunum, liver, and pancreas to induce an upregulation of the physiological activity of any of the cellular constituents of these organs. An aspect of the invention comprises low-intensity ultrasound delivered in a focused or unfocused manner to any of the distal stomach, duodenum, and proximal jejunum in a manner which increases the release of cholecystokinin (any of its isoforms CCK-83, CCK-58, CCK-39, CCK-33, CCK-22, and CCK-8) for the treatment of obese or overweight individuals or those individuals who suffer from binge eating disorders such as bulimia. In this embodiment low-intensity ultrasound is delivered in a focused or unfocused manner to any portion of stomach, duodenum, and proximal jejunum in a manner which increases calcium activity in CCK-secreting cells to stimulate the release of cholecystokinin from CCK-secreting cells for the treatment of obese or overweight individuals or those individuals who suffer from binge eating disorders.

The present invention comprises methods and devices for delivering low-intensity ultrasound that are wearable or personal use devices. The device is worn under clothing and provides ultrasound to the appropriate location(s) before, during or after consumption of calories. An aspect of the invention comprises a device delivering low-intensity ultrasound used in a clinical setting such as for those patients who need to undergo rapid weight loss programs so that the risks associated with certain surgical procedures (GI surgery, cardiothoracic surgery, for example) can be minimized. In an embodiment a single or multiple ultrasound transducers may be surgically implanted to deliver ultrasound waveforms to the stomach, duodenum, jejunum, liver, and pancreas.

The present invention comprises methods and devices for stimulating the vagus nerve using low-intensity ultrasound (0.001 mW/cm$^2$ to 100 W/cm$^2$; focused or unfocused) at the site of the tissue in a manner which increases the activity of vagal afferents projecting to the arcuate nucleus and/or the nucleus solitary tract for the treatment of obese or overweight individuals. The intensity of ultrasound refers to the intensity generated during the delivery of a single treatment event.

The present invention comprises methods and devices for treating obese or overweight individuals by transmitting low-intensity ultrasound in a focused or unfocused manner to the vagus nerve or any portion of one or more of the stomach, duodenum, jejunum, pancreas, and liver in a continuous wave or pulsed manner ranging in duration from 0.000001 seconds to 100,000 seconds during the delivery of any one ultrasound treatment event (a single ultrasound transmission event). An ultrasound treatment event may be repeated at repetition frequencies ranging from once about every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 60, 100, 120, 150, 180, 200, 240, 280, or 360 days, or more. In one example, treatment is given every 30 days up to 10 KHz for a total cumulative ultrasound treatment not to exceed the life of the patient being treated.

The present invention comprises methods and devices for treating obese or overweight individuals where low-intensity ultrasound is applied in a focused or unfocused manner to the vagus nerve or any portion of the stomach, duodenum, jejunum, pancreas, and liver in a manner which increases their physiological activity in a manner to increase satiety and/or fat and/or glucose metabolism.

The present invention comprises methods and devices for transmitting focused and/or unfocused low-intensity ultrasound to the vagus nerve and/or any portion of any of the stomach, duodenum, jejunum, liver, or pancreas for the treatment of obese or overweight individuals in which the acoustic frequencies of ultrasound delivered represent a single or combination of acoustic frequencies ranging minimally from 0.05 to 50 MHz.

The present invention comprises methods and devices for transmitting focused and/or unfocused low-intensity ultrasound to the vagus nerve and/or any portion of any of the stomach, duodenum, jejunum, liver, or pancreas for the treatment of obese or overweight individuals in which a device may be composed of 1 to 1000 ultrasound transducer elements where plate voltages are applied to the ultrasound transducer elements using analog or digitized waveforms composed singly or as a combination of square, sine, sawtooth, or arbitrary waveforms, and wherein the transducers may be activated in a synchronized or phased manner.

The present invention comprises methods and devices for transmitting focused and/or unfocused low-intensity ultrasound to the vagus nerve and/or any portion of any of the stomach, duodenum, jejunum, liver, or pancreas for the treatment of obese or overweight individuals in which a device delivers ultrasound in at least some portion of the treatment in a focused manner, and delivery of focused ultrasound is uses data acquired by medical imaging modalities such as ultrasound imaging, MRI, PET, or others known in the art.

Figure 15:
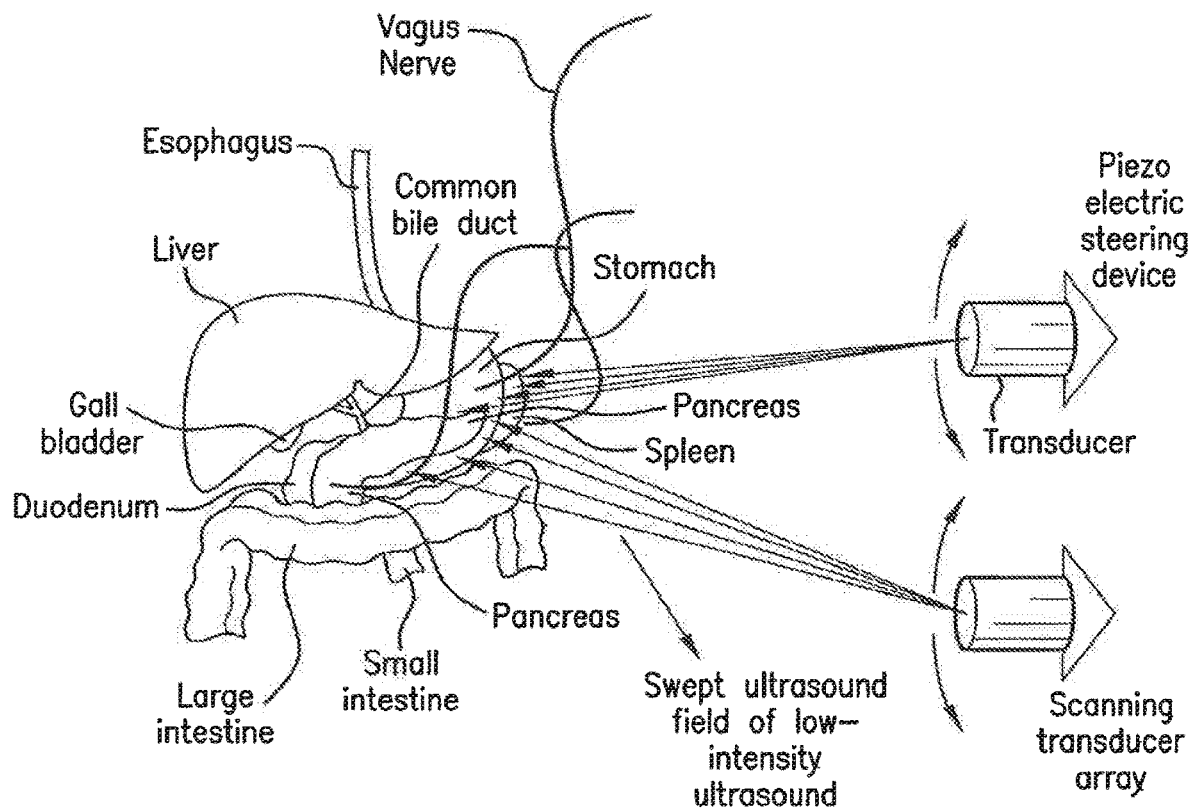
FIG. 15 shows a drawing of methods of the present invention for providing a sweeping ultrasound field to deliver unfocused waves of low-intensity ultrasound to multiple gastrointestinal regions.
Figure 16:
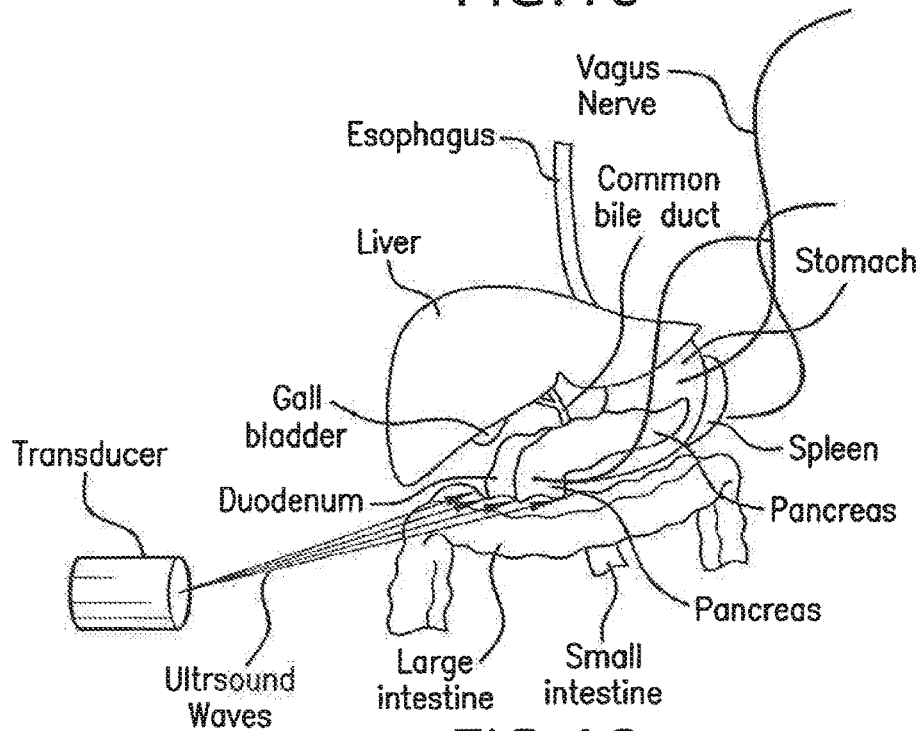
FIG. 16 shows a drawing of methods of the present invention for an array of transducer components to affect vagus nerve efferent and afferent activity for treatment of obesity.

FIGS. 15 and 16 show examples of methods and devices for treatment of obesity. In FIG. 15, ultrasound waves are provided by one or more transducers, such as piezoelectric steering devices, and or by one or more scanning transducer arrays. The vagus nerve efferents and afferents and some portion of one or more gastrointestinal organs may be swept by a low frequency, low intensity ultrasound field. Such a system may be used to deliver a swept, unfocused field of low intensity ultrasound to multiple GI organs and nerves to increase the physiological activity of the vagus nerve and at least a portion of one or more of the pancreas, the stomach, the duodenum, the jejunum and the liver. Not all the organs are shown in the figures. The number of transducers may be 1 to 1000, and may have a mixed range of frequencies. The frequencies of the transducers used may be in a simple design, such that all frequency ranges are the same, or may be in a complex design, in which different transducers have different frequency ranges. For example, one transducer may be at 0.5 MHz, the adjacent transducer at 0.7 MHz, and the adjacent transducer at 0.5 MHz. The transducers may be physically arranged in any known functional design, such as sequentially along a line, or spatially arranged in two or three dimensions to provide unique devices.

FIG. 16 shows methods and devices for direct stimulation with low intensity ultrasound of at least a portion of one or more gastrointestinal organs such as the stomach, duodenum and proximal jejunum. Direct stimulation of at least a portion of one or more gastrointestinal organs may be used in conjunction with stimulation of the vagus nerve afferents or efferents, which may comprise sequential or simultaneous activation by low frequency, low intensity ultrasound. In this example, from 1 to 300 ultrasound transducers are used to modulate the cells of at least a portion of one or more gastrointestinal organs such as the stomach, duodenum and proximal jejunum. An outcome of such stimulation may result in stimulation of CCK signaling.

The present invention comprises methods and devices for stimulating nerves and or organs to decrease fat metabolism and to increase body weight. For example, vagal efferents may be stimulated as described herein, and/or stimulation of hypothalamic regions of the brain may cause weight gain, or inhibit fat metabolism. Such use of ultrasound may be useful in methods of treatment for subjects with anorexia, bulimia, cachexia, or conditions where weight gain is desired, such as during chemotherapy (cancer) treatment or AIDS.

Such weight gain or weight loss methods may be used in conjunction with treatments for conditions such as depression, recovery from surgery or injury, or other conditions wherein weight control is an adjunct issue of the primary condition.

Method and Device Using Low-Intensity, Low-Frequency Ultrasound for Reducing Secondary Brain Damage Following Traumatic Brain Injury of Concussive Event Traumatic brain injury is one of the leading causes of death and morbidity in North America and is a rising global healthcare problem worldwide. Among the patients who die as a result of TBI, approximately 90% die within 48 hours of the primary injury. Over recent years it has been shown that the pathophysiological events associated with TBI or concussive head trauma are delayed and progressive in nature. These delayed and progressive pathophysiological events following head trauma often induce "secondary injury". Secondary injury following head trauma involves a host of molecular cellular signaling cascades and responses in glial cells and neurons including toxicity due to reactive oxygen species (free radicals), glutamate-mediated excitotoxicity, hypoxia, mechanical damage due to high intracranial pressure, excessive calcium influx, disrupted ionic homeostasis, release of pro-inflammatory cytokines, and reactive gliosis. Secondary injuries also occur following mild TBI or concussive head trauma even when the injury may seem "mild" or when the injury does not induce loss of consciousness. Secondary injuries also occur in white matter following traumatic events such as whiplash and can produce diffuse axonal injury (DAI). Secondary injury in both gray and white matter often results from glutamate-mediated excitotoxicity, disrupted calcium homeostasis, and activation of cell death pathways. Preventing the deleterious consequences of these secondary injuries by dampening the effects the molecular cellular signaling cascades triggered following TBI or DAI can lead to improved functional outcomes during recovery processes, as well as increased survival rates by minimizing the impact of the delayed sequelae and progressive pathophysiology.

Methods of treatment comprising early medical attention during pre-hospital care and other acute medical interventions may reduce the damage associated with secondary injury following TBI or DAI. Early medical attention in reducing intracerebral pressure has been attributed to saving many lives and reducing death related to secondary injury following TBI. Several small molecules and biological factors exerting neuroprotective effects have been examined and are thought to protect the brain and nervous system from damage due to secondary injury following TBI or DAI. These factors include anti-inflammatory agents, glutamate receptor modulators (AMPA and NMDA glutamate receptor subtype), neurotrophic factors such as brain-derived neurotrophic factor (BDNF), apoptotic inhibitors, ion channel modulators, nitric oxide modulators, and a host of other pharmacological agents. The invention here describes a method and device for delivering low-intensity, low-frequency ultrasound in a focused or unfocused manner to the brain or nervous system such that the ultrasonic energy induces neuroprotection to mitigate some of the pathophysiological consequences of secondary injury following TBI or DAI.

An aspect of the invention comprises providing low-intensity, low-frequency (0.1 to 10 MHz) ultrasound which penetrates the intact skull and is transmitted into the brain in a focused and/or unfocused manner. Such low-intensity, low-frequency ultrasound methods trigger bioeffects on numerous cellular molecular cascades in a manner to upregulate the production and/or secretion of one or more factors to exert neuroprotection, promote neuronal plasticity, and increase neuronal survival. Low-intensity ultrasound can increase transforming growth factor beta (TGF-$\beta$), insulin-like growth factor receptor-I (IGF), interleukin-8 (IL), basic fibroblast growth factor (bFGF), vascular endothelial growth factor (VEGF), and nitric oxide signaling events in many different cell types. Besides its angiogenic activities, bFGF modulates synaptic transmission, is a potent regulator of neuronal survival and VEGF, TGF-β, and bFGF are also neuroprotective against injury and neurodegeneration. NF-κB is known to regulate neuronal survival and plasticity and the PI3K-Akt signaling pathway is capable of blocking cell death and promoting cell survival of many neuronal cell types. Low-intensity, low frequency ultrasound activates Akt/NF-κB and PI3K/Akt signaling pathway in many cell types. Low-intensity, low-frequency ultrasound increases the synthesis and release of nitric oxide in many cell types, as well as increasing the activity of nitric oxide synthase. Nitric oxide (NO) can mediate neuroprotection, cell death, and neurogenesis following traumatic brain injury. BDNF is a neurotrophic factor, which has cell survival and neuroprotective effects and in addition is a potent regulator of ion channel modulation, as well as neurotransmitter receptors throughout the brain. Here, TBI refers to severe or mild traumatic brain injury where a head trauma has induced a loss of consciousness or not.

The present invention comprises methods and devices for using low-intensity ultrasound (0.001 mW/cm$^2$ to 100 W/cm$^2$; focused or unfocused) at the site of the brain tissue for increasing the signaling activity of neuroprotective molecules (including any of BDNF, NO, NOS, VEGF, TGF-β, bFGF, NF-κB, or PI3K-Akt) to protect the brain (reduce cell death) of any individual from the deleterious consequences of secondary injury following a TBI. The intensity of ultrasound refers to the intensity generated during the delivery of a single treatment event.

The present invention comprises methods and devices for reducing the deleterious consequences of secondary injury following a TBI by transmitting low-intensity ultrasound in a focused and/or unfocused manner to the brain or any portion thereof, where the ultrasound is applied in a continuous wave or pulsed manner ranging in duration from 0.000001 seconds to 1,000,000 seconds during the delivery of any one ultrasound treatment event (a single ultrasound transmission event.) An ultrasound treatment event may be repeated at repetition frequencies ranging from once about every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 60, 100, 120, 150, 180, 200, 240, 280, or 360 days, or more. In one example, treatment is given every 30 days up to 10 KHz for a total cumulative ultrasound treatment not to exceed the life of the patient being treated.

The present invention comprises methods and devices for reducing the deleterious consequences of secondary injury following a TBI by transmitting low-intensity ultrasound in a focused or unfocused manner to the brain or any portion thereof in a manner which modulates calcium activity. Throughout, the term "modulates calcium activity" means that calcium levels in a cell are increased or decreased in comparison to basal levels or to a control.

The methods disclosed herein can reduce the deleterious consequences of secondary injury following a TBI by transmitting low-intensity ultrasound in a focused or unfocused manner to the brain or any portion thereof at any time beginning immediately after TBI up to 1, 2, 3, 4, 5, 6, 7, 8, 9, 10, 11, 12, 13, or 14 days post-injury. The treatment can continue at regular intervals as needed, such as daily, weekly, or monthly. A device of the present invention can be administered by an emergency first responder (i.e., paramedic, EMT), in any pre-hospital first-aid, or during acute medical care (hospital ER). It can also be administered during routine care by a physician, or can be self-administered by a patient. The acoustic frequencies of the ultrasound delivered can represent a single or combination of acoustic frequencies ranging minimally from 0.05 to 50 MHz.

The present invention comprises methods and devices for reducing the deleterious consequences of secondary injury following a TBI or other brain injury by transmitting low frequency, low intensity ultrasound in a focused or unfocused manner to at least a portion of the brain wherein a device comprises from 1 to 1000 ultrasound transducer elements and plate voltages are applied to the transducer elements using analog or analog or digitized waveforms composed singly or as a combination of square, sine, sawtooth, or arbitrary waveforms while the transducers are activated in a synchronized or phased manner. In one embodiment the number of ultrasound transducer elements is less than 300.

The present invention comprises methods and devices for reducing the deleterious consequences of secondary injury following a TBI or other brain injury by transmitting low frequency, low intensity ultrasound in a focused or unfocused manner to at least a portion of the brain in which a device delivers ultrasound in at least some portion of the treatment in a focused manner, and delivery of focused ultrasound uses data acquired by medical imaging modalities such as ultrasound imagining, MRI, PET, or others known in the art. In one embodiment the ultrasound is not focused. In an embodiment, the ultrasound is focused. In an embodiment, the ultrasound may be delivered in a combination of focused and unfocused manners.

Figure 17:
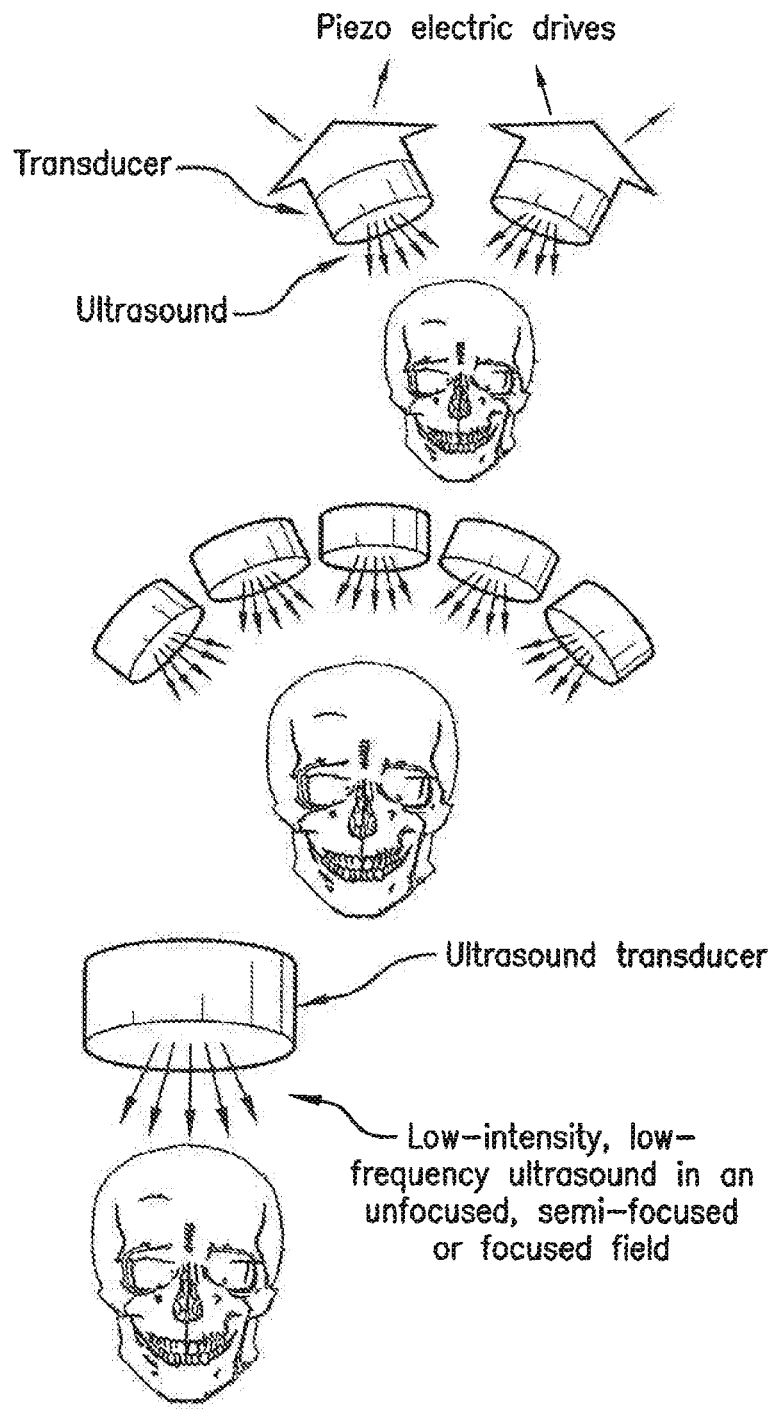
FIG. 17 shows drawings of methods of the present invention for use of an array of transducers for treatment of head injuries that can be portable or used on site by first responders or emergency room personnel.

FIG. 17 is illustrative of methods and devices for rapid treatment of brain injury with low frequency, low intensity ultrasound. A device may comprise one transducer to provide low frequency, low intensity ultrasound or a device may comprise multiple transducers, such as from 2 to 300 transducers spatially arranged to treat the head. Such transducers may be acoustically coupled to the head by elements known in the art. Acoustic coupling may comprise air, water-based media, including, but not limited to, gel, water or fluid filled items such as sponges or other polymer materials, or other materials which have low acoustic attenuation coefficients. These are useful where the skull is fairly intact. A device may also comprise piezoelectric drives or micromotor drives or other components used to translate the spatial position of transducers in order to target particular regions to be modulated by ultrasound. Such devices may be employed in a manner similar to that of AEDs used for rapid cardiac response. The ultrasound devices may be deployed in first responder sites, such as ambulances or helicopters, or on site in buildings such as office towers or airports. Devices may also be deployed in emergency rooms for treatment during triage and acute early intervention. Devices may be used with conscious or unconscious individuals. The delivery of low frequency, low intensity ultrasound is beneficial when applied as soon as possible to the brain of a victim of TBI to provide modulation of cellular activities in the brain and stimulate neuroprotective cellular molecular signaling cascades including, but not limited to, BDNF signaling. Cell death and other secondary injuries are reduced.

Methods and Device Using Low-Intensity, Low-Frequency Ultrasound to Treat Other Neurological Diseases and Conditions The methods and devices of the present invention may be used with organ systems to treat acute and chronic pathologies by modulating cellular activities, including neural and non-neural cells, by providing low frequency, low intensity ultrasound. An effect of providing low frequency, low intensity ultrasound is to stimulate cell signaling pathways. Thus, the methods and devices of the present invention are useful in treatments for many organs, organ systems, nerve systems, and pathological conditions found in humans, animals, plants and other living organisms. For example, the present invention comprises methods and devices for treating cardiac arrhythmia in a subject comprising: acoustically coupling a low intensity ultrasound transducer device to the subject; and driving the ultrasound transducer to form stimulus waveform with an intensity in a range of 0.001 to 900 mW/cm$^2$ at the site of the tissue. Testing with other procedures or patient response may indicate the effectiveness of the treatment, and determine repeating US treatment or altering of US treatment.

The present invention comprises methods and devices for treating a subject in a minimally conscious state, a coma, or a vegetative state, the method comprising acoustically coupling a low intensity ultrasound transducer device to the subject; and driving the ultrasound transducer to form stimulus waveform with an intensity in a range of 0.001 mW/cm$^2$ to 900 milliWatts per square centimeter at the site of the tissue. Testing with other procedures or patient response may indicate the effectiveness of the treatment, and determine repeating US treatment or altering of US treatment.

The present invention comprises methods and devices for treating a subject with locked-in syndrome comprising acoustically coupling a low intensity ultrasound transducer device to the subject; and driving the ultrasound transducer to form stimulus waveform with an intensity in a range of 0.001 to 900 milliWatts per square centimeter (mW/cm$^2$) at the site of the tissue. Testing with other procedures or patient response may indicate the effectiveness of the treatment, and determine repeating US treatment or altering of US treatment.

The present invention comprises methods and devices for treating a subject with a spinal cord injury comprising acoustically coupling a low intensity ultrasound transducer device to the subject; and driving the ultrasound transducer to form stimulus waveform with an intensity in a range of 0.001 to 900 milliWatts per square centimeter (mW/cm$^2$) at the site of the tissue. Testing with other procedures or patient response may indicate the effectiveness of the treatment, and determine repeating US treatment or altering of US treatment.

The present invention comprises methods and devices for treating a subject with back pain comprising acoustically coupling a low intensity ultrasound transducer device to the subject; and driving the ultrasound transducer to form stimulus waveform with an intensity in a range of 0.001 to 900 milliWatts per square centimeter (mW/cm$^2$) at the site if the tissue. Testing with other procedures or patient response may indicate the effectiveness of the treatment, and determine repeating US treatment or altering of US treatment.

The present invention comprises methods and devices for treating a subject with migraine headaches comprising acoustically coupling a low intensity ultrasound transducer device to the subject; and driving the ultrasound transducer to form stimulus waveform with an intensity in a range of 0.001 to 900 milliWatts per square centimeter (mW/cm$^2$) at the site of the tissue. Testing with other procedures or patient response may indicate the effectiveness of the treatment, and determine repeating US treatment or altering of US treatment.

The present invention comprises methods and devices for treating Parkinson's disease or essential tremor in a subject comprising acoustically coupling a low intensity ultrasound transducer device to the subject; and driving the ultrasound transducer to form stimulus waveform with an intensity in a range of 0.001 to 900 milliWatts per square centimeter (mW/cm$^2$) at the site of the tissue or neuronal circuit to be treated. Testing with other procedures or patient response may indicate the effectiveness of the treatment, and determine repeating US treatment or altering of US treatment.

Methods and Device Using Low-Intensity, Low-Frequency Ultrasound for Functional Brain Mapping The present invention comprises methods and devices for conducting non-invasive functional brain mapping using low intensity ultrasound in a subject comprising acoustically coupling a low intensity ultrasound transducer device to the subject; and driving the ultrasound transducer to form stimulus waveform with an intensity in a range of 0.001 to 900 milliWatts per square centimeter (mW/cm$^2$) at the site of the tissue. Devices for reading neuronal activity, such as MEG, MRI, EEG, fMRI, PET, acoustic radiation force imaging, photoacoustic tomography and others can be used in conjunction or combination with providing ultrasound waves such that the neurosignal resulting from the ultrasound is recorded and/or monitored or mapped. Such measurements may occur in >0.0000001 second from the onset of the ultrasound stimulation waveform and last during and following the waveform for a period of up to about 1000 seconds.

The present invention comprises methods and devices for targeted neuromodulation comprising utilizing imaging data in a subject to direct the ultrasound treatment of the subject, wherein the ultrasound is provided by acoustically coupling a low intensity ultrasound transducer device to the subject; and driving the ultrasound transducer to form stimulus waveform with an intensity in a range of 0.001 to 900 milliWatts per square centimeter (mW/cm$^2$) at the site of the tissue. The imaging data may be derived from devices that provide sonography, MRI, PET, photoaccoustic tomography, tissue pulsatility imaging, acoustic radiation force imaging, vibrography or other methods, and such devices may be combined with ultrasound devices of the present invention to provide low frequency, low intensity ultrasound treatments focused by direction from the imaging data. Ultrasound data imaging may comprise use of high intensity ultrasound, such as MR-thermometry, for data relating to location of treatment sites, and such high intensity ultrasound for imaging may comprise ultrasound with up to 1000 W/cm$^2$. The present invention contemplates use of ultrasound imaging techniques wherein data is generated using high or low intensity ultrasound, and such imaging may be used with the modulation of cellular activity, such as neuromodulation, disclosed herein.

In the methods of the present invention, imaging may be accomplished by acoustic radiation force imaging (ARFI) or tissue pulsatile imaging. Use of such imaging techniques may replace the use of MRI. Ultrasound imaging may helpful in visualizing where the ultrasound is being steered through the skull. In an aspect of the invention using ARFI or tissue pulsatile imaging, the frequency of ultrasound may range from 0.01 to 5 MHz. Methods of the present invention comprise conducting ultrasound imaging of a portion of a subject, and then using the imaging data generated, to act as a guide to the location where ultrasound treatment, such as an ultrasound stimulus waveform, is to be provided. For example, the present invention comprises methods, systems and devices for using low intensity ultrasound to acquire a map of the brain vasculature for use as a guide to provide information for conducting ultrasound neuromodulation or other tissue modulation. For example, ultrasound imaging data, or other imaging data, may be used to map metabolic activity in a subject and the data regarding the location of the metabolic activity acts as a guide to the location where ultrasound treatment, such as an ultrasound stimulus waveform, is to be provided.

Methods and Device Using Low-Intensity, Low-Frequency Ultrasound for Neuromodulation The present invention comprises methods and devices for modulating neuronal cellular activity in a subject comprising transcranially transmitting sets of pulsed ultrasound waveforms. Methods for modulating neuronal cellular activity comprise acoustically coupling an ultrasound transducer to an external surface of a subject, and driving the ultrasound transducer to form stimulus waveform with an intensity below about 900 milliWatts per square centimeter (mW/cm$^2$) and an ultrasound frequency below about 0.9 MegaHertz (MHz) at the site of the tissue. The frequencies comprise single components, multiple components, or a combination thereof. An aspect of the present invention comprises ultrasound waveforms having and ultrasound frequency ranging from about 0.25 to about 0.50 MHz. In an aspect of the present invention, the ultrasound waveforms act in a non-thermal fashion without causing significant heating of the tissue being treated.

The present invention comprises methods and devices for modulating neuronal cellular activity in a subject comprising transcranially transmitting sets of pulsed ultrasound waveforms, wherein the waveform comprises a plurality of single pulses. An aspect of the present invention comprises single pulses that have a pulse duration ranging from about 0.16 to about 0.57 msec. An aspect of the present invention comprises single pulses that are repeated at a pulse repetition frequency ranging from about 1.2 to about 3.0 KHz to produce spatial-peak temporal-average intensities ranging from about 21 to about 163 mW/cm$^2$. In an aspect of the present invention, single pulses comprise between about 80 and about 225 acoustic cycles. Pulses can be generated by brief bursts of waves. Waves may be one or more of known wave, including but not limited to, sine, square, saw tooth and triangle. The ultrasound waves may be focused to provide action at a particular site in or on the subject, or the waves may be unfocused and provide action at multiple sites. The waves may be continuous or pulsed, depending on the desired application. The frequency or intensity may be uniform throughout a treatment period, or may alternate or sweep from one number to another, and back to the original number. Those skilled in the art are able to determine such parameters for the desired application. Examples are disclosed herein.

An aspect of the present invention comprises methods and devices for modulating neuronal cellular activity in a subject comprising transcranially transmitting sets of pulsed ultrasound waveforms, wherein the duration of the transcranial transmission ranges from about 26 to about 333 msec.

An aspect of the present invention comprises methods and devices for modulating neuronal cellular activity in a subject comprising transcranially transmitting sets of pulsed ultrasound waveforms, wherein neuronal cellular activity is modulated through ion channel or ion transporter activity. In an aspect of the present invention, the ion channel or ion transporter regulates activity of calcium, potassium, chloride, or sodium. In an aspect of the present invention, the neuronal cellular activity relates to the secretion of signaling molecules, the proliferation of cells, the differentiation of cells, the modulation of protein transcription, the modulation of protein translation, or a combination thereof.

The present invention comprises methods and devices for modulating neuronal cellular activity in a subject comprising transcranially transmitting sets of pulsed ultrasound waveforms, wherein the ultrasound transducer comprises piezoelectric transducers, composite transducers, CMUTs, or a combination thereof. In an aspect of the invention, the ultrasound transducer can be implanted onto the subject's skull or mounted onto the subject's skull. For example, in an aspect, a CMUT is implanted on the skull. In another aspect, a CMUT can also be mounted onto the subject's skull in a chronically wearable device.

The present invention comprises methods and devices for modulating neuronal cellular activity in a subject comprising transcranially transmitting sets of pulsed ultrasound waveforms, wherein the ultrasound transducer comprises up to about 1000 elements. In an aspect of the present invention, the number of elements is 1, 10, 20, 30, 40, 50, 60, 70, 80, 90, 100, 150, 200, 250, 300, 350, 400, 450, 500, 550, 600, 650, 700, 750, 800, 850, 900, 950, or 1000 elements. In an aspect of the present invention, the number of elements ranges from about 1 to about 299.

The present invention comprises methods and devices for modulating neuronal cellular activity in a subject comprising transcranially transmitting sets of pulsed ultrasound waveforms, wherein the method for modulating neuronal cellular activity is used in conjunction with EEG, MEG, MRI, PET, acoustic radiation force imaging, photoacoustic tomography, or a combination thereof. In an aspect of the present invention, the method for modulating neuronal cellular activity further comprising using an algorithm in a closed- or open-loop manner to evaluate feedback of brain activity and modifying the stimulus waveform based on that feedback.

The present invention comprises methods and devices for using acoustic pressure of ultrasound to induce fluid mechanical actions in nervous tissues, brain, or brain circuits in order to modulate neuronal activity.

The present invention comprises transcranial ultrasound waveform for modulating cellular activity. In an aspect of the present invention, the transcranial ultrasound waveform is used in conjunction with an acoustically coupled ultrasound transducer comprising an intensity below about 900 milliWatts per square centimeter (mW/cm$^2$) and an ultrasound frequency below about 0.9 MegaHertz (MHz), preferably ranging from about 0.25 to about 0.50 MHz. In an aspect of the invention, the ultrasound waveform comprises a plurality of single pulses. A single pulse can have a pulse duration ranging from about 0.16 to about 0.57 msec. Single pulses can be repeated at a pulse repetition frequency ranging from about 1.2 to about 3.0 KHz to produce spatial-peak temporal-average intensities ranging from about 21 to about 163 mW/cm$^2$. A single pulse comprises between about 80 and about 225 acoustic cycles. In an aspect of the present invention, the duration of the transcranial transmission ranges from about from about 26 to about 333 msec. In an aspect of the present invention, driving the acoustically coupled ultrasound transducer comprises piezoelectric transducers, composite transducers, CMUTs, or a combination thereof.

Figure 12:
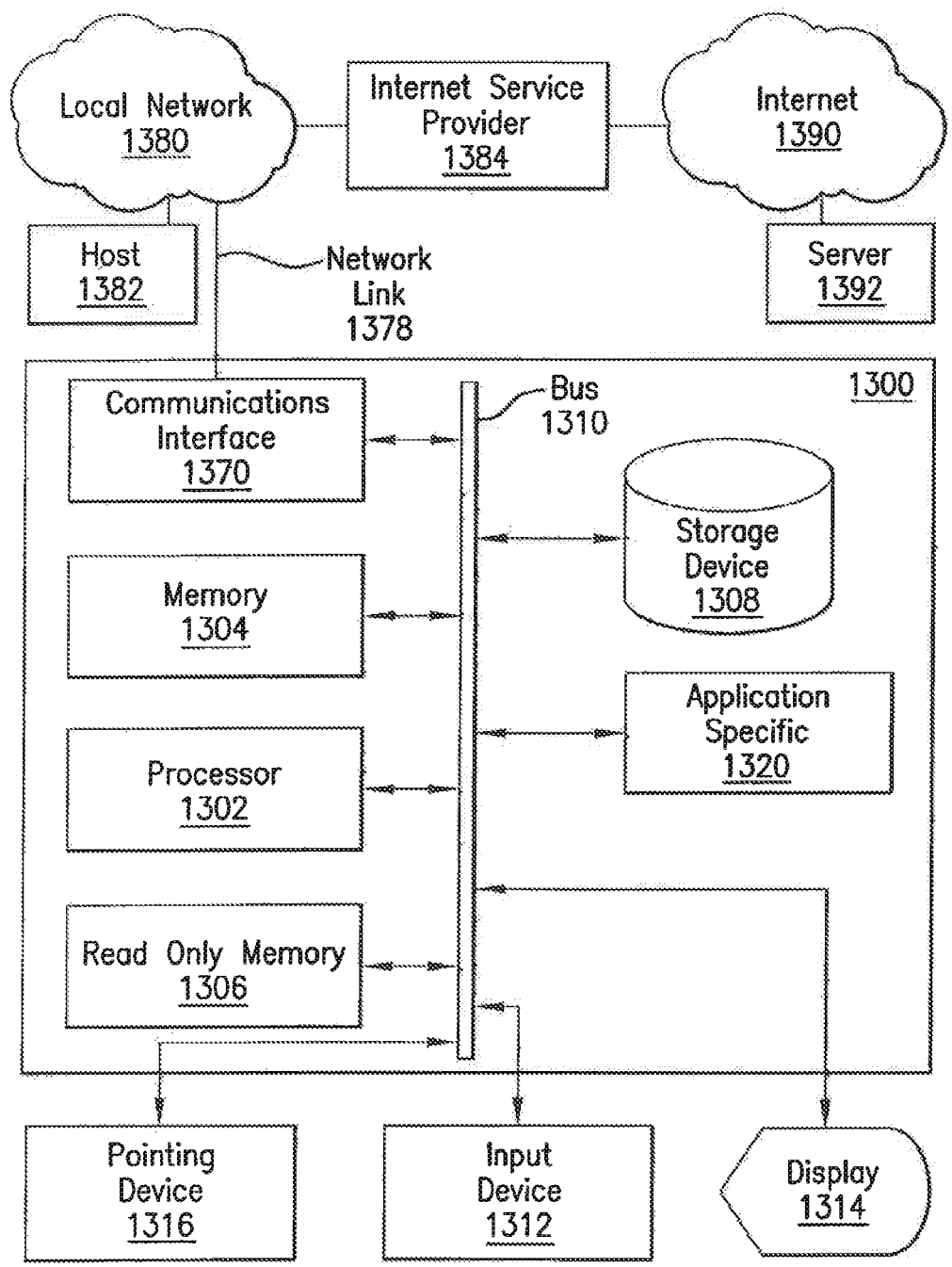
FIG. 12 shows a block diagram that illustrates a computer system upon which an embodiment of the invention may be implemented.

The present invention comprises methods and devices wherein a computer is used. For example, FIG. 12 is a block diagram that illustrates a computer system 1300 upon which an embodiment of the invention may be implemented. Computer system 1300 includes a communication mechanism such as a bus 1310 for passing information between other internal and external components of the computer system 1300. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit). A sequence of binary digits constitutes digital data that is used to represent a number or code for a character. A bus 1310 includes many parallel conductors of information so that information is transferred quickly among devices coupled to the bus 1310. One or more processors 1302 for processing information are coupled with the bus 1310. A processor 1302 performs a set of operations on information. The set of operations include bringing information in from the bus 1310 and placing information on the bus 1310. The set of operations also typically include comparing two or more units of information, shifting positions of units of information, and combining two or more units of information, such as by addition or multiplication. A sequence of operations to be executed by the processor 1302 constitutes computer instructions.

Computer system 1300 also includes a memory 1304 coupled to bus 1310. The memory 1304, such as a random access memory (RAM) or other dynamic storage device, stores information including computer instructions. Dynamic memory allows information stored therein to be changed by the computer system 1300. RAM allows a unit of information stored at a location called a memory address to be stored and retrieved independently of information at neighboring addresses. The memory 1304 is also used by the processor 1302 to store temporary values during execution of computer instructions. The computer system 1300 also includes a read only memory (ROM) 1306 or other static storage device coupled to the bus 1310 for storing static information, including instructions, that is not changed by the computer system 1300. Also coupled to bus 1310 is a non-volatile (persistent) storage device 1308, such as a magnetic disk or optical disk, for storing information, including instructions, that persists even when the computer system 1300 is turned off or otherwise loses power.

Information, including instructions, is provided to the bus 1310 for use by the processor from an external input device 1312, such as a keyboard containing alphanumeric keys operated by a human user, or a sensor. A sensor detects conditions in its vicinity and transforms those detections into signals compatible with the signals used to represent information in computer system 1300. Other external devices coupled to bus 1310, used primarily for interacting with humans, include a display device 1314, such as a cathode ray tube (CRT) or a liquid crystal display (LCD) or a display comprised of light emitting diodes (LED) or organic light emitting diodes (OLED), for presenting images, and a pointing device 1316, such as a mouse or a trackball or cursor direction keys, for controlling a position of a small cursor image presented on the display 1314 and issuing commands associated with graphical elements presented on the display 1314.

In the illustrated embodiment, special purpose hardware, such as an application specific integrated circuit (IC) 1320, is coupled to bus 1310. The special purpose hardware is configured to perform operations not performed by processor 1302 quickly enough for special purposes. Examples of application specific ICs include graphics accelerator cards for generating images for display 1314, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 1300 also includes one or more instances of a communications interface 1370 coupled to bus 1310. Communication interface 1370 provides a two-way communication coupling to a variety of external devices that operate with their own processors, such as printers, scanners and external disks. In general the coupling is with a network link 1378 that is connected to a local network 1380 to which a variety of external devices with their own processors are connected. For example, communication interface 1370 may be a parallel port or a serial port or a universal serial bus (USB) port on a personal computer. In some embodiments, communications interface 1370 is an integrated services digital network (ISDN) card or a digital subscriber line (DSL) card or a telephone modem that provides an information communication connection to a corresponding type of telephone line. In some embodiments, a communication interface 1370 is a cable modem that converts signals on bus 1310 into signals for a communication connection over a coaxial cable or into optical signals for a communication connection over a fiber optic cable. As another example, communications interface 1370 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 1370 sends and receives electrical, acoustic or electromagnetic signals, including infrared and optical signals that carry information streams, such as digital data.

The term computer-readable medium is used herein to refer to any medium that participates in providing information to processor 1302, including instructions for execution. Such a medium may take many forms, including, but not limited to, non-volatile media, volatile media and transmission media. Non-volatile media include, for example, optical or magnetic disks, such as storage device 1308. Volatile media include, for example, dynamic memory 1304. Transmission media include, for example, coaxial cables, copper wire, fiber optic cables, and waves that travel through space without wires or cables, such as acoustic waves and electromagnetic waves, including radio, optical and infrared waves.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read.

Network link 1378 typically provides information communication through one or more networks to other devices that use or process the information. For example, network link 1378 may provide a connection through local network 1380 to a host computer 1382 or to equipment 1384 operated by an Internet Service Provider (ISP). ISP equipment 1384 in turn provides data communication services through the public, world-wide packet-switching communication network of networks now commonly referred to as the Internet

1390. A computer called a server 1392 connected to the Internet provides a service in response to information received over the Internet. For example, server 1392 provides information representing video data for presentation at display 1314.

The invention is related to the use of computer system 1300 for implementing the techniques described herein. According to one embodiment of the invention, those techniques are performed by computer system 1300 in response to processor 1302 executing one or more sequences of one or more instructions contained in memory 1304. Such instructions, also called software and program code, may be read into memory 1304 from another computer-readable medium such as storage device 1308. Execution of the sequences of instructions contained in memory 1304 causes processor 1302 to perform the method steps described herein. In alternative embodiments, hardware, such as application specific integrated circuit 1320, may be used in place of or in combination with software to implement the invention. Thus, embodiments of the invention are not limited to any specific combination of hardware and software.

The signals transmitted over network link 1378 and other networks through communications interface 1370, carry information to and from computer system 1300. Computer system 1300 can send and receive information, including program code, through the networks 1380, 1390 among others, through network link 1378 and communications interface 1370. In an example using the Internet 1390, a server 1392 transmits program code for a particular application, requested by a message sent from computer 1300, through Internet 1390, ISP equipment 1384, local network 1380 and communications interface 1370. The received code may be executed by processor 1302 as it is received, or may be stored in storage device 1308 or other non-volatile storage for later execution, or both. In this manner, computer system 1300 may obtain application program code in the form of a signal on a carrier wave.

Various forms of computer readable media may be involved in carrying one or more sequence of instructions or data or both to processor 1302 for execution. For example, instructions and data may initially be carried on a magnetic disk of a remote computer such as host 1382. The remote computer loads the instructions and data into its dynamic memory and sends the instructions and data over a telephone line using a modem. A modem local to the computer system 1300 receives the instructions and data on a telephone line and uses an infra-red transmitter to convert the instructions and data to a signal on an infra-red a carrier wave serving as the network link 1378. An infrared detector serving as communications interface 1370 receives the instructions and data carried in the infrared signal and places information representing the instructions and data onto bus 1310. Bus 1310 carries the information to memory 1304 from which processor 1302 retrieves and executes the instructions using some of the data sent with the instructions. The instructions and data received in memory 1304 may optionally be stored on storage device 1308, either before or after execution by the processor 1302.

The present invention discloses methods, systems and devices for modulating cellular activity in a subject. In general, the present invention comprises acoustically coupling at least one component for generating ultrasound waves to an external surface of a subject, and driving at least one component for generating ultrasound waves to form at least one ultrasound stimulus waveform, wherein the stimulus waveform comprises one or more frequencies, with an intensity in a range from about 0.0001 to about 900 mW/cm$^2$ and a frequency in a range from about 0.02 to about 1.0 MHz, at the site of the cells to be modulated. The ultrasound stimulus waveform may comprise at least an ultrasound frequency ranging from about 0.10 to about 0.90 MHz. The ultrasound stimulus waveform may comprise single- or multiple-component frequencies. The duration of one or more ultrasound stimulus waveforms may range from about from about 0.01 to about 10000 msec. The ultrasound stimulus waveform may comprise a plurality of single pulses, wherein a single pulse has a pulse duration ranging from about 0.001 to about 10000 msec. In an aspect of the invention, single pulses may be repeated at a pulse repetition frequency ranging from about 0.001 to about 100 KHz to produce spatial-peak temporal-average intensities ranging from about 21 to about 500 mW/cm$^2$. In an aspect of the present invention, a single pulse may comprise between about 1 and about 50,000 acoustic cycles. In the presently disclosed methods, a pulse may be generated by brief bursts of square waves, sine waves, saw-tooth waveforms, sweeping waveforms, or arbitrary waveforms, or combinations of one or more waveforms. The waveforms may be focused or not focused. The method may be repeated. The components for generating ultrasound, such as ultrasound transducer or its elements, are driven using analog or digitized waveforms. Ultrasound transducer elements may be driven using individual waveforms or a combination of square, sine, saw-tooth, or arbitrary waveforms.

Methods for modulating cellular activity in a subject may further comprise detecting modulated cellular activity in cells. Modulated cellular activity includes but is not limited to changes in (i) the ion channel activity, (ii) the ion transporter activity, (iii) the secretion of signaling molecules, (iv) the proliferation of the cells, (v) the differentiation of the cells, (vi) the protein transcription of the cells, (vii) the protein translation of cells, (viii) the protein phosphorylation of the cells, (ix) the protein structures in the cells, or a combination thereof.

In the present invention, at least one component for generating ultrasound waves comprises an ultrasonic emitter, an ultrasound transducer, a piezoelectric ultrasound transducer, a composite transducer, a capacitive micromachined ultrasound transducer, or combinations thereof. In an aspect of the present invention, more than one component for generating ultrasound waves is used and one or more components may be found in an array configuration. In one aspect of the disclosed methods, the component for generating ultrasound waves may be physically attached to, wearably attached to, or implanted in the subject. In an aspect of the present invention, the number of elements of a component, such as the number of elements that comprise an ultrasonic transducer or CMUT, that may be used in an ultrasound device may range from about 1 to 299 transducer or CMUT elements, from about 1 to 1000 transducer or CMUT elements.

Methods for modulating cellular activity may be used with other methods for imaging or acting on a subject. For example, electroencephalogram, magnetoencephalography, magnetic resonance imaging, positron emission tomography, computed tomography, or a combination may used with ultrasound treatments to modulate cellular activity. Methods for modulating cellular activity may comprise a closed- or open-feedback loop, and analyzing means, such as an algorithm or logic device, to evaluate feedback data from the subject and modify the ultrasound stimulus waveform based on that feedback data. Methods may comprise use of a light emitting device. Methods for modulating cellular activity may be repeated, such as performing the method of providing an ultrasound stimulus waveform two or more times.

Methods for targeted cellular modulation comprises combined steps of imaging a portion of the subject and then providing one or more ultrasound stimulus waveforms to modulate cellular activity, and particularly cellular activity in the portion of the subject for which imaging data had been obtained. For example, a method comprises producing ultrasound imaging data of a portion of a subject, wherein the ultrasound imaging data was obtained by acoustically coupling at least one component for generating ultrasound waves to an external surface of a subject, driving at least one component for generating ultrasound waves to form at least one ultrasound waveform, wherein the waveform comprises one or more frequencies, with an intensity in a range from about 0.0001 to about 900 mW/cm$^2$ and a frequency in a range from about 0.01 to 5 MHz, at the site of the cells to be imaged, and using the ultrasound data generated as a guide in determining where to provide at least one ultrasound stimulus waveform, which comprises acoustically coupling at least one component for generating ultrasound waves to an external surface of a subject, and driving at least one component for generating ultrasound waves to form at least one stimulus waveform, wherein the stimulus waveform comprises one or more frequencies, with an intensity in a range from about 0.0001 to about 900 mW/cm$^2$ and a frequency in a range from about 0.02 to about 1.0 MHz, at the site of the cells to be modulated. In an aspect of the invention, the ultrasound waves may be low-intensity ultrasound waves. Methods for modulating cellular activity in targeted neuromodulation comprise using imaging data to map information that may be used in ultrasound treatment for modulation of cellular activity in the brain. For example, neuronal or cellular metabolic activity may be mapped, or the time of a neurosignal may be monitored in response to an ultrasound transmission.

Methods for modulating cellular activity by providing ultrasound treatment include modulating neuronal cellular activity and treating a subject with a brain tumor. In treating a subject with a brain tumor, the at least one component for generating ultrasound waves may comprise 1 to 1000 ultrasound transducer elements. In treating a subject with a brain tumor, the temperature of the tissue in the brain tumor may remain between 30° C. and 44° C. during application of ultrasound, and may not exceed 40° C. for more than 10 seconds. The ultrasound treatment may be provided to the subject in combination with another treatment including but not limited to surgery, chemotherapy, recombinant proteins, small organic molecules, or pharmaceutical agents.

The present invention discloses methods for modulating cellular activity in reducing consequences of secondary injury following a traumatic brain injury in a subject and the treatment may be repeated, may be given at any time beginning immediately after the traumatic brain injury, and may be given to the subject in combination with another treatment for traumatic brain injury. The present invention discloses methods for modulating cellular activity in treating a subject with a spinal cord injury, treating a subject with migraine, treating a subject with back pain, treating a subject with Parkinson's disease, essential tremor, Alzheimer's disease, obsessive compulsive disorder, schizophrenia, bipolar disorder, depression or other disease or condition originating in the central nervous system of a subject, treating a subject in a minimally conscious state, a coma, or a vegetative state, treating a subject with locked in syndrome, treating a subject with a cardiac arrhythmia or treating a subject with diabetes comprising providing ultrasound treatment comprising acoustically coupling at least one component for generating ultrasound waves to the subject, and driving at least one component for generating ultrasound waves to form at least the stimulus waveform, wherein the stimulus waveform comprises one or more frequencies, with an intensity in a range from about 0.0001 to about 900 mW/cm$^2$ at the site of the cells to be modulated. In an aspect, the acoustic frequency may be delivered to the subject in a single or combination of acoustic frequencies ranging from 0.05 to 50 MHz. The stimulus waveform may be administered in a focused manner or in an unfocused manner. In the disclosed methods, the stimulus waveform may be administered in a continuous wave or pulsed manner. In treating diabetes, the stimulus waveform may be provided to the pancreas or vagus nerve of the subject.

The present invention comprises ultrasound wave generating devices for low intensity ultrasound transmission, wherein the ultrasound transducer forms a stimulus waveform with an intensity in a range of 0.001 to 900 mW/cm$^2$ generated at the site of the tissue. The present invention comprises ultrasound stimulus waveforms for modulating cellular activity comprising an intensity in a range from about 0.0001 to about 900 mW/cm$^2$ at the site of the cells to be modulated, one or more ultrasound frequencies in a range from about 0.02 to about 1.0 MHz, at the site of the cells to be modulated, and a plurality of single pulses, wherein a single pulse has a pulse duration ranging from about 0.001 msec to about 10 minutes, wherein single pulses are repeated at a pulse repetition frequency ranging from about 0.001 to about 10 KHz to produce spatial-peak temporal-average intensities ranging from about 21 to about 900 mW/cm$^2$ at the site of cells to be modulated, wherein single pulse comprises between about 10 and about 50000 acoustic cycles, wherein the duration of the ultrasound transmission ranges from about 0.01 msec to about 10 sec.

DEFINITIONS

As used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points.

For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

The term "treating" refers to inhibiting, preventing, curing, reversing, attenuating, alleviating, minimizing, suppressing or halting the deleterious effects of a disease and/or causing the reduction, remission, or regression of a disease. Those of skill in the art will understand that various methodologies and assays can be used to assess the development of a disease, and similarly, various methodologies and assays may be used to assess the reduction, remission or regression of the disease.

"Increase" is defined throughout as 1, 2, 3, 4, 5, 6, 7, 8, 9, 10, 11, 12, 13, 14, 15, 16, 17, 18, 19, 20 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 150, 200, 250, 300, 400, or 500 times increase as compared with basal levels or a control.

Example 1: Quantification of Synaptic Activity in Hippocampal Slice Cultures Hippocampal slice cultures were prepared from thy-1-synaptopHluorin (spH) mice. SynaptopHlourin is expressed in both excitatory and inhibitory hippocampal neurons of thy-1-spH mice. Synaptic vesicle release (exoytosis) at an individual release site from these mice is indicated by spH which fluoresces at a particular wavelength (about 530 nm) in the green portion of the optical spectrum when excited by laser light at 488 nm from laser-scanning confocal microscope. The intensity of fluorescent emissions (F) from all sites in view is measured to quantify synaptic activity. ΔF expressed as a percentage indicates percentage changes in total intensity of the fluorescence; and therefore percentage changes in synaptic activity. Synaptic activity is indicated by spH in both a CA1 stratum radiatum (CA1 SR) region and a CA1 stratum pyramidale (CA1 SP) region—the latter a region with a particularly high density of inhibitory synapses. Thus modulation of neural activity indicated by spH can indicate excitatory or inhibitory modulation or some combination

Figure 6A:
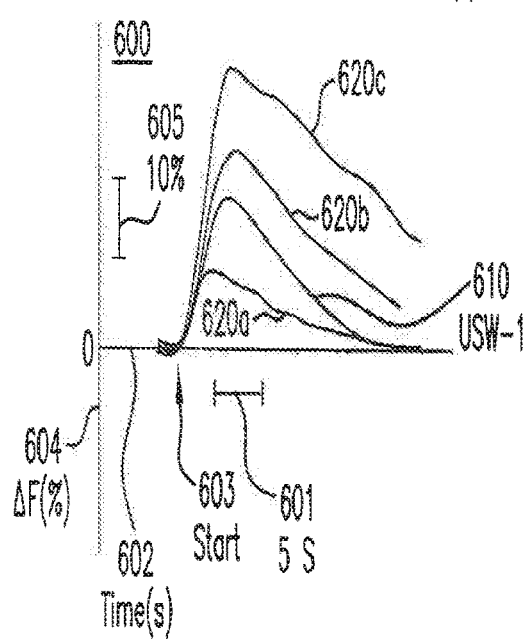
FIG. 6A shows a graph that illustrates comparative temporal responses of neural activity after modulation by electrical impulses and after modulation by an ultrasound waveform.

Example 2: Comparison of Effects of Neural Activity Inducement Between Ultrasound and Conventional Means To determine whether the effects of ultrasound modulation are comparable to neural activity changes induced by more invasive, conventional means, consider FIG. 6A and FIG. 6B. FIG. 6A is a graph 600 that illustrates comparative temporal responses of neural activity after modulation by electrical impulses and after modulation by an ultrasound waveform, according to an embodiment. The horizontal axis 602 is time in seconds; and the horizontal scale is given by segment 601 that corresponds to 5 seconds. The vertical axis 604 indicates ΔF in percent (%); and the vertical scale is given by segment 605 that corresponds to 10%. The start of USW-1 is indicated by tick 603. Curve 610 indicates the average temporal response from USW-1, from over 148 individual responses, as given by average response 540 in graph 530. Curve 620a indicates the response of spH fluorescence in Schaffer collaterals regions of neural tissue to electrical stimulation using monopolar electrodes at 40 action potentials (AP) and 20 Hz (averaged over n=51 individual synapses). Similarly, curves 620b and 620c indicate the response of spH fluorescence in Schaffer collaterals to electrical stimulation using monopolar electrodes at 100 AP/20 Hz (n=63) and 250 AP/50 Hz (n=48), respectively.

Thus, graph 600 shows that the time rate of change (kinetics) and amplitudes of ultrasound triggered spH response, indicated by curve 610, are on the same order as those obtained in response to electrical stimulation, curves 620. The response is also similar to spH responses previously reported for different stimuli. This indicates that ultrasound is as effective as electrical stimulation for the treatment of neural disease and disorders.

Figure 6B:
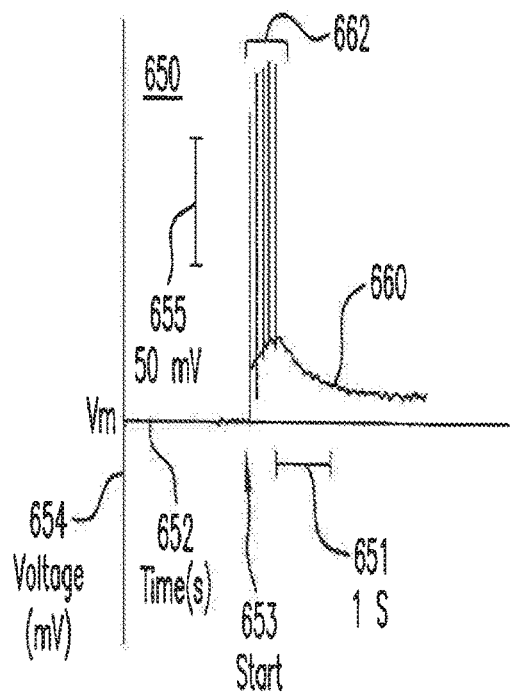
FIG. 6B shows a graph that illustrates temporal electrical responses of a neuron after modulation by an ultrasound waveform.

FIG. 6B is a graph 650 that illustrates temporal electrical responses of a neuron after modulation by an ultrasound waveform, according to an embodiment. The horizontal axis 652 is time in seconds; and the horizontal scale is given by segment 651 that corresponds to 1 second. The vertical axis 654 indicates voltage difference across the neuronal membrane in milliVolts (mV); and the vertical scale is given by segment 655 that corresponds to 50 mV. Here a different ultrasound waveform, referenced as USW-2 is used. USW-2 consists of five pulses, each at 0.44 MHz for 10 square wave cycles for a pulse length of 22.7 μs. The PRF is a constant 10 Hz, so the entire waveform lasts just over 0.5 seconds (one tenth the duration of USW-1). The start of USW-2 is indicated by tick 653.

Trace 660 indicates action potentials (e.g., membrane voltage) in response to pulsed ultrasound waveforms during whole-cell current clamp recordings of CA1 pyramidal neurons. The trace 660 includes five spikes 662 that represent neural firing (transmission of an electrical pulse) along the neuron during the 0.5 seconds of the waveform. However, in general, whole-cell electrophysiological approaches were not very useful in studying ultrasonic neuromodulation due to electrode resonations producing loss of whole-cell seals during ultrasound waveform propagation. Thus, graph 650 shows that the time rate of change (kinetics) and amplitudes of ultrasound membrane potential indicated by trace 660 shows neuron firing induced by low intensity ultrasound waveforms.

Cavitation or other evidence of gross membrane damage was not observed at the low intensities used herein. Slice cultures prepared from thy-1-YFP mice 10 were chronically modulated with USW-1 every 8 minutes for 36-48 hours. The membrane structures of YFP+ neurons receiving such chronic ultrasound modulation were similar to unmodulated controls. According to an embodiment, chronic modulation with ultrasound waveforms does not cause gross membrane damage in CA1 SP region. Using histological techniques, no indications of cell damage are evident. Histology indicates the presence of fine structures such as dendritic spines for both control and chronically modulated conditions. Chronically stimulated neurons appear to have more dendrites. Thus, in some embodiments, ultrasound waveforms are repeated for sufficient duration to modulate neuronal morphology in subtle ways which can mediate neural function.

Thus, low intensity pulsed ultrasound waveforms appear to be highly effective in modulating neural activity, safe for prolonged use, and able to stimulate desirable changes in neuronal morphology.

Example 3: Stimulation of SNARE-Mediated Synaptic Vesicle Exocytosis and Synaptic Transmission by Low-Intensity, Low-Frequency Ultrasound Changes in membrane tension produced by the absorbance of mechanical energy (e.g., sound waves) alter the activity of individual neurons due to the elastic nature of their lipid bilayers and spring-like mechanics of their transmembrane protein channels. In fact, many voltage-gated ion channels, as well as neurotransmitter receptors possess mechanosensitive properties permitting them to be differentially gated by changes in membrane tension. Therefore, a set of methods for investigating the influence of mechanical energy conferred on neuronal activity by ultrasound were utilized. Using these methods, it was found that pulsed ultrasound is capable of stimulating SNARE-mediated synaptic transmission, as well as voltage-gated sodium ($Na^+$) and (calcium) $Ca^{2+}$ channels in central neurons. SNARE proteins are a class of proteins that include neuronal Synaptobrevin (n-Syb), SNAP-25 and Syntaxin 1A (Syx 1A), and Synaptotagmin I (Syt I) that play a role in synaptic transmission and vesicle exocytosis. These measurements utilized the following procedures.

Hippocampal slice cultures were taken from postnatal day 7-8 thy-1-spH, thy-1-YFP, or wild-type mice in a manner similar to previously described methods. Briefly, transverse hippocampal slices (about 400 μm thick) were prepared with a wire slicer (MX-TS, Siskiyou, Inc., Grants Pass, Oreg., USA) and maintained in vitro on Millicell-CM filter inserts (PICMORG50, Millipore, Bedford, Mass.) in a 36° C., 5% $CO_2$, humidified (99%) incubator. Slices were used for experiments between 7 and 12 days in vitro. To cleave SNARE-proteins in some experiments, BoNT/A at 250 nanograms per milliliter (ng/mL, 1 ng=$10^{-9}$ grams and 1 mL=$10^{-3}$ Liters) was added to the slice culture media 24-36 hours prior to experiments.

Following $CO_2$ inhalation, mice were rapidly decapitated and their entire brains were removed, the dura was carefully removed, and the brain was then placed in ice-cold dissection artificial CSF (aCSF) containing 83 milliMoles (mM, 1 mM=$10^{-3}$ Moles of a compound) NaCl, 2.5 mM KCl, 3.3 mM $MgSO_4$, 1 mM $NaH_2PO_4$, 26.2 mM $NaHCO_3$, 22 mM glucose, 72 mM sucrose, and 0.5 mM $CaCl_2$, and equilibrated with 95% $O_2$/5% $CO_2$. Brains were allowed to recover for 5 minutes in ice-cold aCSF before recovering for about 20 minutes at 37° C. before being bulk loaded for some experiments with OGB-1 AM dye at room temperature (21-23° C.).

In order to load slice cultures prepared from wild-type mice with CoroNa Green AM (Invitrogen, Carlsbad, Calif., USA) 5 microLiters (AL, 1 μL=$10^{-6}$ Liters) 20% Pluronic F-127 in DMSO (Invitrogen) was added to a 50 microgram (μg, 1 μg=$10^{-6}$ grams) vial of CoroNa Green AM. The dye solution was then vortexed for 15 minutes before adding 100 μL culture medium. Then 5 μL of the dye-containing solution was added to 1 μL culture medium underneath culture inserts, as well as adding 5 μL to the surface of slices. Following a 10 minute loading time at 36° C., slices were washed three times with slice culture medium, allowed to recover an additional 10 minutes, and then used for experiments. To load slice cultures with OGB-1 AM (Invitrogen), 2 μL, 20% Pluronic F-127 in DMSO (Invitrogen) and 8 μL was added to a 50 μg vial of OGB-1 AM. The dye-containing solution was then vortexed for 30 minutes before adding 90 μL culture medium. Then 20 μL of this dye-containing solution was added to 3 mL culture medium and slices were incubated in this solution for 30-40 minutes at 37° C. Slices were washed three times with slice culture medium, then loaded with sulforhodamine 101 (Invitrogen; 10 μM in slice culture medium for 15 minutes) or allowed to recover for 30 minutes before being used in experiments. In order to load ex vivo brains with OGB-1 AM we used a procedure similar to that described above, but substituted the slice culture medium for dissection aCSF (see above)—60 μl of the dye-containing solution was added to 9 mL dissection aCSF. Brains were loaded for 30 minutes at room temperature then rinsed three times and allowed to recover for an additional 30 minutes at room temperature before use.

Slice cultures or whole ex vivo brains were transferred to a recording chamber containing normal aCSF. Normal aCSF contains 136 mM NaCl, 2.5 mM KCl, 1.3 mM $MgSO_4$, 10 mM HEPES, 10 mM glucose, and 2.5 mM $CaCl_2$), pH 7.4 at room temperature. Recording chambers were affixed over transducers on a custom built-stage on an Olympus Fluoview FV-300 laser-scanning confocal microscope (Olympus America, Inc., Center Valley, Pa., USA). Excitation of spH, OGB-1 AM, and CoroNa Green AM was performed using a 488 nanometer (nm, 1 nm=$10^{-9}$ meters) optical wavelength of an argon laser and in some experiments DiI was excited using a 546 nm HeNe laser. Time-series images were acquired using 20× (lens with 0.5 numerical aperture, NA) or 40× (0.8 NA) Olympus UMPlanFL water-immersion lenses.

Slice recording chambers consisted of culture inserts and a constructed aCSF reservoir held in place either by vacuum grease or superficial tension between the silicon face of transducers and the insert. This approach produced a 4.5 mm standoff distance between the face of the transducer and the imaging plane on the surface of slices. In some cases, to test remote transmission of ultrasound waveforms on neuronal activity, slice cultures were mounted at the top of an aCSF column in a 500 mL beaker containing immersed transducers, which were affixed to the bottom beakers providing a 45 mm standoff distance. The ventral (bottom) surface of whole ex vivo brains were glued to the bottom of polystyrene 6-well plates using superglue, which were filled with aCSF and mounted on transducers using ultrasonic coupling gel. Confocal imaging of OGB-1 in ex vivo brains was conducted on the superficial dorsal (top) surface of ex vivo brains during and after transmission of pulsed ultrasound waveforms through the brain from the ventral surface.

Whole-cell current clamp recordings from visually identified CA1 pyramidal neurons were performed using standard approaches. Briefly, patch electrode pipettes filled with an intracellular solution containing 130 mM KCl, 10 mM Na-HEPES, 10 mM Di-Tris-P-creatine, 0.2 mM EGTA, 3 mM Mg-ATP, and 0.5 mM Na-GTP, 280-290 mM mOsm, pH 7.2; the final resistance of these unpolished patch electrodes was 5-7 megaOhms (MΩ, 1 MΩ=$10^6$ ohms). Current clamp recordings were performed using a MultiClamp 700B patch-clamp amplifier with pCLAMP 10 software (Molecular Devices, Sunnyvale, Calif., USA). Following 5-10 minutes of whole-cell access, changes in membrane voltage were recorded in response to stimulation with pulsed ultrasound waveforms.

Confocal images were analyzed offline using ImageJ (see, e.g., http://rsb.info.nih.gov/ij/) or the Olympus Fluoview 5.0 software. We express changes in spH fluorescence as a percent change from baseline fluorescence levels. For OGB-1 and CoroNa Green signals, $\Delta F/F_0$ was calculated using standard approaches $\Delta F = F - F_0$. Characteristics of ultrasound waveforms and electrophysiological analyses were performed offline using Igor Pro (WaveMetrics, Lake Oswego, Oreg., USA). Data shown are mean±S.E.M. The resulting measurements provide insight into the mechanisms for ultrasound control on neural activity.

Transmission of USW-1 into slices triggered synaptic vesicle exocytosis producing a ΔF due to spH of 18.52%±2.2% at individual release sites (148 samples) in CA1 stratum radiatum (as shown above in FIG. 5). Several other pulsed ultrasound waveforms were identified, which were effective at triggering synaptic vesicle release as listed below in Table 1. For example, an ultrasound waveform composed of pulses with f=0.67 MHz, PL=74.5 μs, c/p=50,000 delivered at PRF=10 Hz with Np=5 (for a 0.5 duration) also stimulated synaptic vesicle release, as indicated by an ΔF due to spH=12.86%±2.6%, for 74 samples.

TABLE 1

Effectiveness of Low Intensity Pulsed Waveforms in Stimulating Synaptic Vesicle Release According to Multiple Embodiments

| PL | c/p | F (Mhz) | PRF | Np | p-p sq. wave amplitude | spH response |
|---|---|---|---|---|---|---|
| 22.7 μs | 10 | 0.44 | 5 s ramp 0-100 Hz | 250 | 500 mV | + |
| 74.5 ms | 50,000 | 0.67 | 10 Hz | 5 | 150 mV | + |
| 74.5 ms | 50,000 | 0.67 | 10 Hz | 150 | 100 mV | + |
| 22.7 μs | 10 | 0.44 | 5 s ramp 0-100 Hz | 250 | 100 mV | − |
| 2.27 μs | 1 | 0.44 | 5 s ramp 0-100 Hz | 250 | 500 mV | − |
| 11.35 μs | 5 | 0.44 | 5 s ramp 0-100 Hz | 250 | 500 mV | + |
| 11.35 μs | 5 | 0.44 | 5 s ramp 0-100 Hz | 250 | 100 mV | − |
| 2.27 μs | 1 | 0.44 | 20 Hz | 100 | 500 mV | − |
| 22.7 μs | 10 | 0.44 | 20 Hz | 100 | 500 mV | + |
| 22.7 μs | 10 | 0.44 | 250 Hz | 250 | 500 mV | − |
| 22.7 μs | 10 | 0.44 | 10 s ramp 0-100 Hz | 500 | 500 mV | + |
| 22.7 μs | 10 | 0.44 | 15 s ramp 0-100 Hz | 750 | 500 mV | + |
| 113.5 μs | 50 | 0.44 | 5 s ramp 0-10 Hz | 25 | 500 mV | − |
| 113.5 μs | 50 | 0.44 | 5 s ramp 0-200 Hz | 500 | 500 mV | + |
| 113.5 μs | 50 | 0.44 | 5 s ramp 0-100 Hz | 250 | 500 mV | + |
| 170.25 μs | 75 | 0.44 | 5 s ramp 0-100 Hz | 250 | 500 mV | + |
| 227.0 μs | 100 | 0.44 | 5 s ramp 0-100 Hz | 250 | 500 mV | + |
| 22.7 μs | 10 | 0.44 | 50 Hz | 250 | 500 mV | − |

Using a DiIoistic labeling approach to visualize dendritic spines, populations of putative excitatory terminals were examined. No difference was found between the ultrasound induced ΔF due to spH obtained from terminals impinging on dendritic spines and somatic synapses impinging on cell bodies. The spine synapses showed ΔF due to spH=19.94%±1.7%; and somatic synapses ΔF due to spH=20.55%±2.7%, with 45 samples for each.

To determine the mechanisms affected by low intensity ultrasound waveforms, various inhibitors known to affect certain processes were introduced to the slices of neural tissue. For example, SNARE-mediated exocytosis is inhibited by BoNT/A. Introducing 250 ng/mL BoNT/A nearly abolished exocytosis in response to low intensity ultrasound waveforms. Thus it is concluded that low intensity ultrasound waveforms excite SNARE-mediated exocytosis. Sodium ion ($Na^+$) conductance is inhibited by voltage gated $Na^+$ channel pore blocker tetrodotoxin (TTX). Introducing 1 μM of TTX nearly abolishes exocytosis in response to low intensity ultrasound waveforms. Thus it is concluded that low intensity ultrasound waveforms relies on Na conductance. Synaptic transmission other than exocytosis is blocked by CNQX and APV. Adding 20 μM CNQX and 100 μM APV blocked excitatory network activity and reduced ΔF due to spH by about 6 percentage points (50% of the low intensity ultrasound effect), thus indicating that low intensity ultrasound waveforms stimulates synaptic transmission and not just exocytosis.

Figure 7:
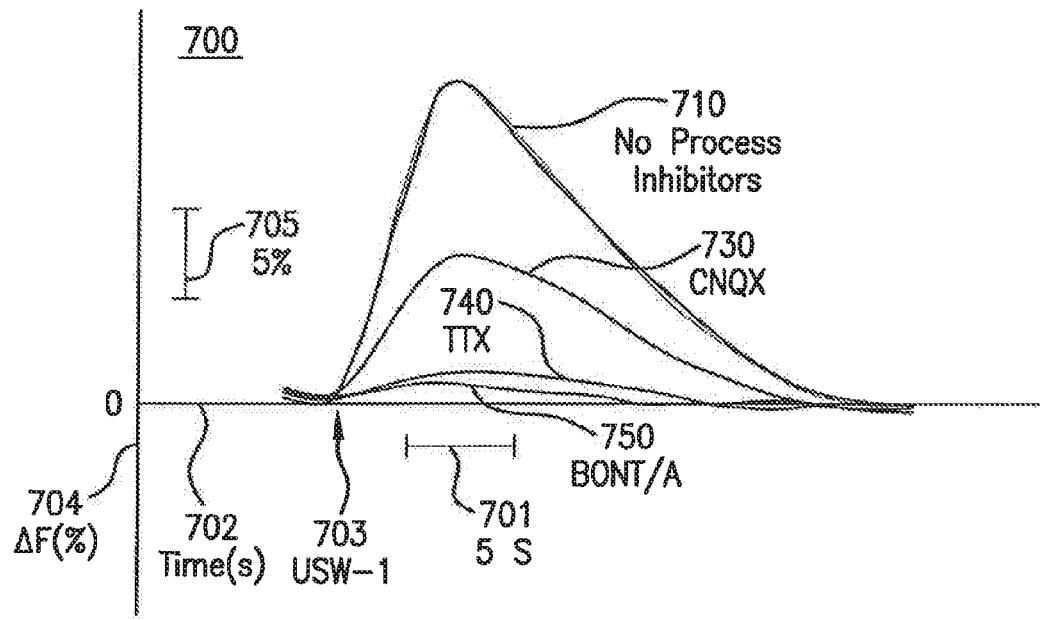
FIG. 7 shows a graph that illustrates example effects of some process inhibitors on neural activity modulated by an ultrasound waveform, according to an embodiment; is an image that illustrates an example effect on neural sodium ($Na^+$) transients after modulation by an ultrasound waveform.

FIG. 7 is a graph 700 that illustrates example effects of some process inhibitors on neural activity modulated by an ultrasound waveform, according to an embodiment. The horizontal axis 702 is time in seconds; and the horizontal scale is given by segment 701 that corresponds to 5 seconds. The vertical axis 704 indicates ΔF in percent (%); and the vertical scale is given by segment 705 that corresponds to 5%. The start of USW-1 is indicated by tick 703. Curve 710 indicates the average temporal response to USW-1 when no process inhibitors are introduced to the neural tissue. Curve 730 indicates the average temporal response when 20 μM CNQX and 100 μM APV are added to block excitatory network activity, reducing the effect of USW-1 by half to about 6%. Curve 740 indicates the average temporal response when 1 μM of TTX is added to inhibit sodium ($Na^+$) conductance, nearly abolishing the effect of USW-1. Curve 750 indicates the average temporal response when 250 ng/mL BoNT/A is added to inhibit SNARE-mediated exocytosis, again nearly abolishing the effect of USW-1.

Figure 8:
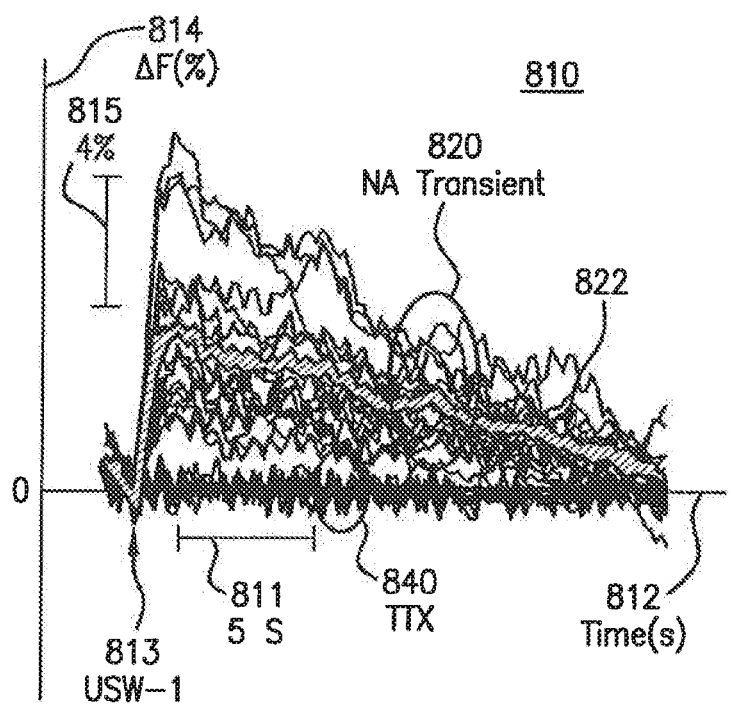
FIG. 8 shows a graph that illustrates an example temporal effect on neural sodium ($Na^+$) transients after modulation by an ultrasound waveform.

Example 4: Stimulation of Voltage-Dependent Calcium Transients in Neurons by Low-Intensity, Low-Frequency Ultrasound Using the $Na^+$ indicator CoroNa Green AM, as known in the art, in cultures prepared from wild-type mice, it was found that USW-1 triggered $Na^+$ transients in CA1 pyramidal neurons (CA1 SP). According to an embodiment, FIG. 8 is a graph 810 that illustrates an example temporal effect on neural Na transients after modulation by an ultrasound waveform, according to an embodiment. The horizontal axis 812 is time in seconds; and the horizontal scale is given by segment 811 that corresponds to 5 seconds. The vertical axis 814 indicates ΔF due to CoroNa Green in percent (%); and the vertical scale is given by segment 815 that corresponds to 4%. The start of USW-1 is indicated by tick 813. Individual responses of Na transients after each ultrasound waveform are given by traces 820 and the average response indicated by curve 822. The maximum response was $\Delta F/F_0 = 5\% \pm 0.6\%$ for n=18 measurements. This response was blocked by the addition of tetrodotoxin (TTX) as indicated by the individual responses 840.

To determine if pulsed ultrasound waveforms were also capable of activating $Ca^{2+}$ transients, slice cultures prepared from wild-type mice were loaded with the $Ca^{2+}$-indicator Oregon Green 488 BAPTA-1 AM (OGB-1 AM) and Sulforhodamine 101 to differentiate between neurons and glial cells, as known in the art. According to an embodiment, USW-1 activation of $Ca^{2+}$ transients in both neurons and glial cells can be visualized using histological techniques that include, but are not limited to, the use of green fluorescence from OGB-1 in neurons, and by yellow fluorescence from Sulforhodamine in glial cells.

Figure 9:
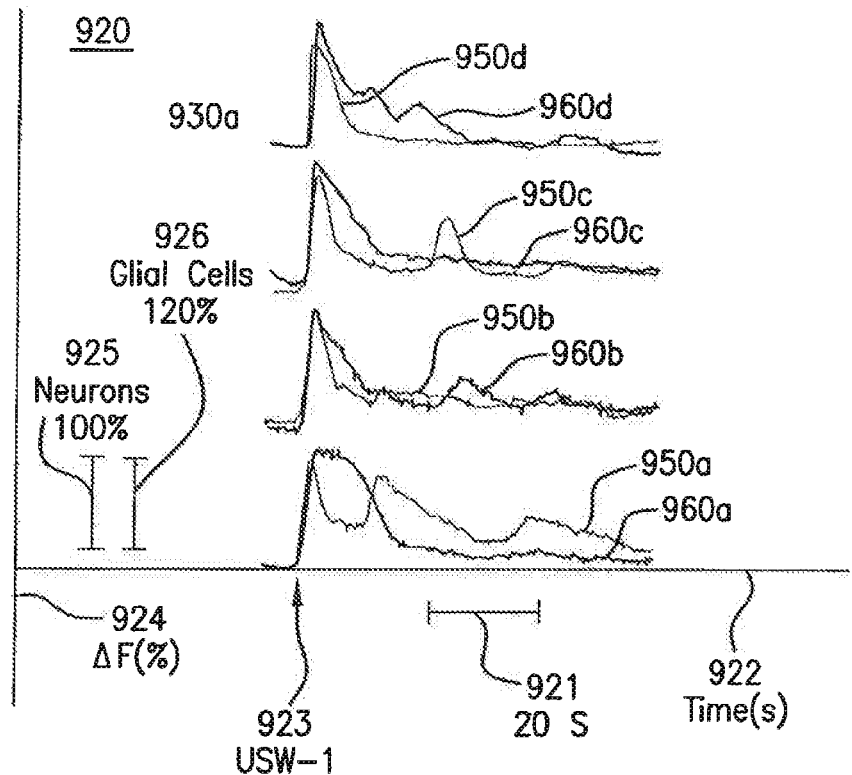
FIG. 9 shows a graph that illustrates example temporal effects on neural and glial calcium ($Ca^{2+}$) transients after modulation by an ultrasound waveform.

FIG. 9 is a graph 920 that illustrates example temporal effects on neural and glial Ca transients after modulation by an ultrasound waveform, according to an embodiment. The horizontal axis 922 is time in seconds; and the horizontal scale is given by segment 921 that corresponds to 20 seconds. The vertical axis 924 indicates ΔF in percent (%); and the vertical scale is given by segment 925 that corresponds to 100% for neurons and segment 926 that corresponds to 120% for glial cells. The zero value is offset for each set of curves to visually separate them. The start of USW-1 is indicated by tick 923. Individual responses of $Ca^{2+}$ transients after each of four USW-1 instances are given by traces 950a, 950b, 950c and 950d for neurons and by traces 960a, 960b, 960c and 960d for glial cells, respectively. For neurons, $F/F_0=114\%\pm10\%$ in 61 samples. For glial cells, $\Delta F/F_0=140\%\pm12\%$ for 55 samples. There are some differences in the time rate of change between the two cell types.

Modulation with USW-1 also induced presynaptic $Ca^{2+}$ transients in CA1 SR. According to an embodiment, USW-1 activation of presynaptic $Ca^{2+}$ transients in CA1 SR can be visualized using histological techniques that include, but are not limited to, the use of green fluorescence from OGB-1 in neurons. The observed $\Delta F/F_0=76\%\pm7\%$ for 31 samples.

Figure 10:
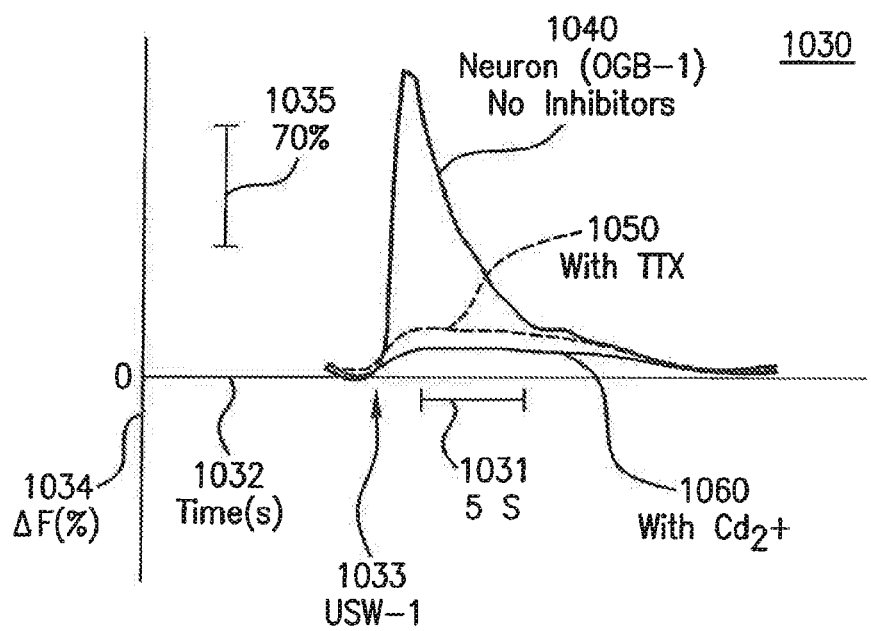
FIG. 10 shows a graph that illustrates an example temporal effect on neural presynaptic activity by modulation with an ultrasound waveform.

Example 5: Activation of Voltage-Gated Sodium Channels in Neurons by Low-Intensity, Low-Frequency Ultrasound To determine whether ultrasound triggered $Ca^{2+}$ transients are primarily mediated by voltage-gated $Ca^{2+}$ channels, $Cd^{++}$ was added to block voltage gated $Ca^{2+}$ channels. Adding 500 μM $Cd^{++}$ nearly abolished OGB-1 signals in response to USW-1. Likewise, the addition of TTX blocked about 85% of the OGB-1 signal produced by USW-1. FIG. 10 is a graph 1030 that illustrates an example temporal effect on neural presynaptic activity by modulation with an ultrasound waveform, according to an embodiment. The horizontal axis 1032 is time in seconds; and the horizontal scale is given by segment 1031 that corresponds to 5 seconds. The vertical axis 1034 indicates ΔF of OGB-1 in percent (%); and the vertical scale is given by segment 1035 that corresponds to 70%. The start of USW-1 is indicated by tick 1033. Curve 1040 indicates the average presynaptic temporal response of OGB-1 to USW-1 when no process inhibitors are introduced to the neural tissue. Curve 1050 indicates the average temporal response when TTX is added to inhibit $Na^+$ conductance, nearly abolishing the effect of USW-1. Curve 1060 indicates the average temporal response when $Cd^{++}$ is added to block voltage-gated $Ca^{2+}$ channels, again nearly abolishing the effect of USW-1. Residual $Ca^{2+}$ transients not blocked by $Cd^{++}$ or tetrodotoxin (TTX) are likely to involve other $Ca^{2+}$ sources such a NMDA or TRPC 1 receptors, which interestingly both possess mechanosensitive properties and are expressed in hippocampal neurons. Using ultrasound waveforms with shorter duration (e.g., f=0.44 MHz, PL=0.18 ms, c/p=80, PRF=10 Hz, and Np=3), $Ca^{2+}$ transients were observed in neurons ($\Delta F/F_0=38\%\pm2\%$, for 24 samples) with faster kinetics.

Since salt-containing solutions confer low acoustic impedance ($\sim1.56\times10^6$ N·s/m³), $Ca^{2+}$ transients were observed in response to low intensity pulsed ultrasound waveforms even when transducers were placed 45 mm away from slices (data not shown). Soft biological tissues (including brain) have acoustic impedances ranging from 1.5-1.8× $10^6$ N·s/m³. To determine whether $Ca^{2+}$ responses could be obtained by transmitting low intensity pulsed ultrasound through intact brain, OGB-1 fluorescence was measured on the dorsal surface of ex vivo brains obtained from wild-type adult mice while transmitting low intensity pulsed ultrasound waveforms through their ventral surfaces. In this ex vivo brain preparation, $Ca^{2+}$ transients were observed in response to low intensity pulsed ultrasound waveforms, which were similar to those observed in slice cultures.

Enhanced effects were noted for some low intensity waveforms. For example, one such low intensity waveform included three pulses (Np=3) at PRF=10 Hz with c/p=80, but with different ultrasound frequencies at alternating pulses, e.g., f=0.44 MHz in the first and third pulse and f=0.67 MHz in the second pulse. This pulse produced substantially greater excitation of neural activity compared to other waveforms tested at an intensity less than 10 mW/cm².

Example 6: Examination of the Influence of Ultrasound Stimulus Waveforms on Intact Brain To conduct transcranial ultrasound (US) stimulation of intact motor cortex, mice were anesthetized using a ketamine-xylazine cocktail (70 mg/kg ketamine, 7 mg/kg xylazine) administered intraperitoneally. The hair on the dorsal surface of the head over regions corresponding to motor cortex was trimmed using microdissection scissors. Mice were then placed in a Cunningham mouse stereotax and affixed to a vibration isolation table. Ultrasound transducers with affixed focusing guides were lowered to points above the skin corresponding to motor cortex identified using standard coordinates. Focusing tubes were then placed on the dorsal surface of the skin above motor cortex and acoustically coupled to the skin using ultrasound coupling gel. Transcranial pulsed US stimulus waveforms were delivered to the targeted motor cortex using a standard TTL triggering protocol and a digital I/O device (Digidata 1440; Molecular Devices, Sunnyvale, Calif., USA) connected to a PC controlled using pClamp software (Molecular Devices) to activate function generators. TTL signal markers indicated the onset and length of US stimulus waveforms. Video recordings of stimulation trials were acquired using a standard webcam. During stimulation trials, electrophysiological data (multi-unit activity (MUA), LFP, and EMG were acquired; see below). Following stimulation, animals were either allowed to recover from anesthesia or processed as described in the materials and methods below.

More specifically, low-intensity US waveforms were transmitted through acoustic focusing guides to the intact motor cortex of anesthetized mice (n=127). FIG. 18A shows an illustration of the method used to transmit laterally focused US stimulus waveforms to intact mouse motor cortex. The optimal gains between transcranial transmission and brain absorption occurs for US at acoustic frequencies (f)<1.0 MHz. Thus, transcranial stimulus waveforms in the frequency range of 0.25 to 0.50 MHz were constructed, while also varying intensity and using 80 to 225 cycle pulses.

Figure 21:
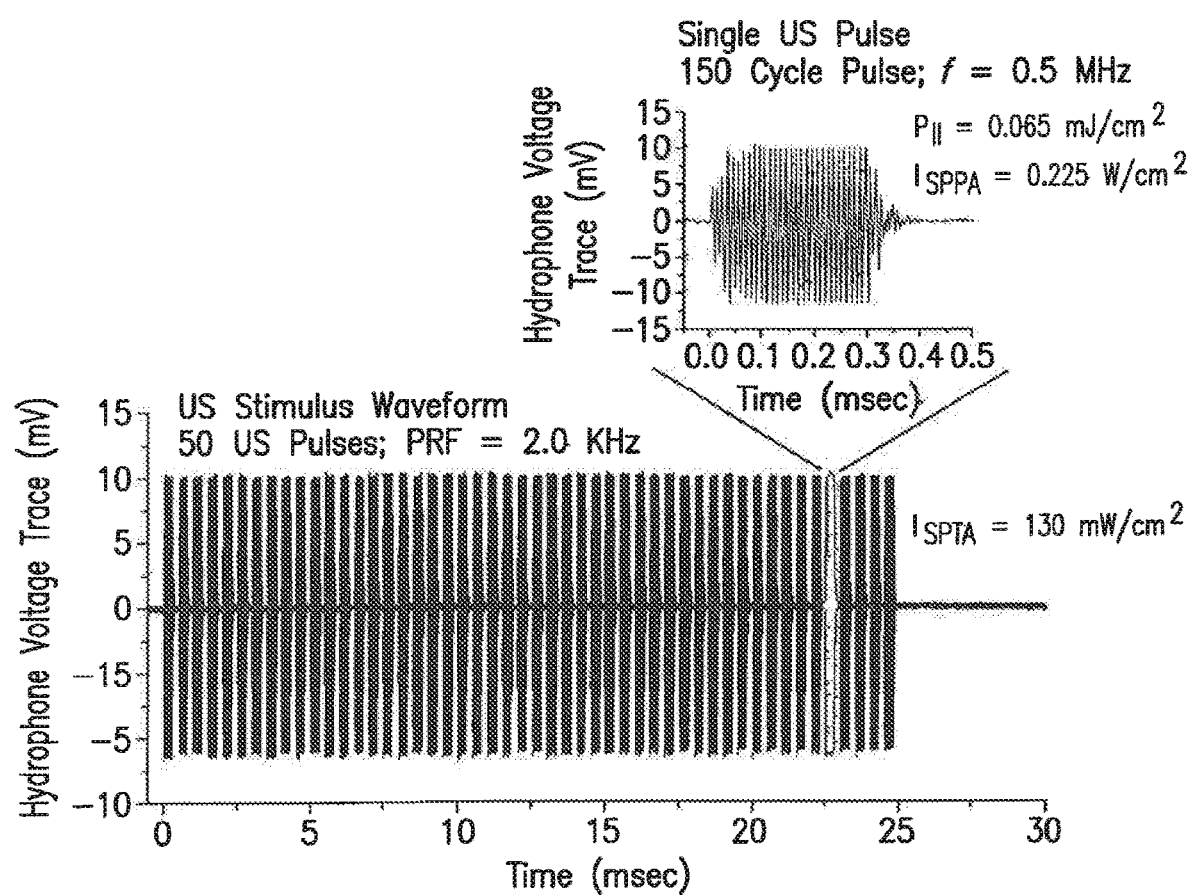
FIG. 21 shows the strategy for constructing typical low-intensity ultrasound waveforms.

FIGS. 18B and 21 show examples of the strategy and parameters used in constructing low-intensity US stimulus waveforms. Intensities generated by the illustrated stimulus waveform are given in the yellow-box. Ultrasound (US) stimulus waveforms were constructed using methods similar to those previously described. Twenty-five (25) mm diameter, water-matched, broadband US transducers having a center frequency of 0.5 MHz (V301-SU, Olympus NDT, Waltham, Mass., USA) were used. Ultrasound (US) pulses were generated by brief bursts of square waves (0.2 μsec; 0.5 mV peak-to-peak) using an Agilent 33220A function generator (Agilent Technologies, Inc., Santa Clara, Calif., USA). Square waves were further amplified (50 dB gain) using an ENI 240L RF amplifier. US pulses were repeated at a pulse repetition frequency by triggering the above referenced function generator with a second Agilent 33220A function generator.

Single ultrasound pulses had pulse durations (PD) lasting from 0.16 to 0.57 msec, peak rarefactional pressures ($p_r$) of 0.070 to 0.097 MPa, pulse intensity integrals (PII) of 0.017 to 0.095 mJ/cm$^2$, and spatial-peak pulse-average intensities ($I_{SPPA}$) of 0.075 to 0.229 W/cm$^2$. Single US Pulses were repeated at pulse repetition frequencies (PRF) ranging from 1.2 to 3.0 KHz to produce spatial-peak temporal-average intensities ($I_{SPTA}$) of 21 to 163 mW/cm$^2$ for transcranial stimulus durations of 26 to 333 msec. The above reported intensities were measured transcranially at points corresponding to intact motor cortex in fresh ex vivo heads. It was observed that <10% intensity loss due to transmission of US waveforms through the hair, skin, skull, and dura of mice (FIG. 22).

Figure 22:
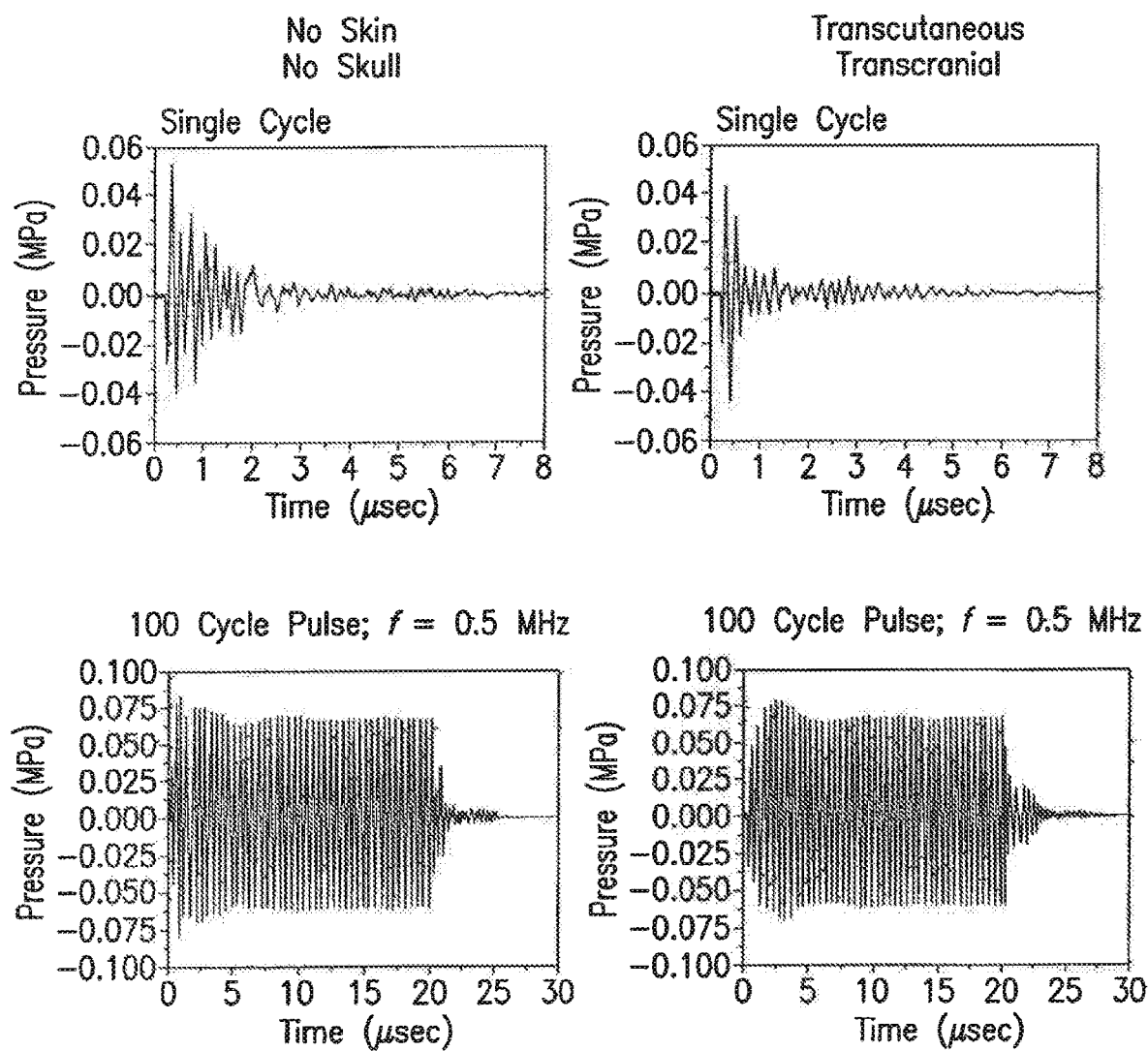
FIG. 22 shows attenuation of ultrasound stimulus waveforms by transcranial transmission.

In FIG. 22, a single cycle (top) and 100 cycle pulse (bottom) of 0.5 MHz was transmitted through ultrasonic coupling gel from the transducer face directly to the face of a hydrophone (left) or through a fresh ex vivo head (right) containing hair, skin, skull, and dura to the face of a hydrophone.

Figure 23A:
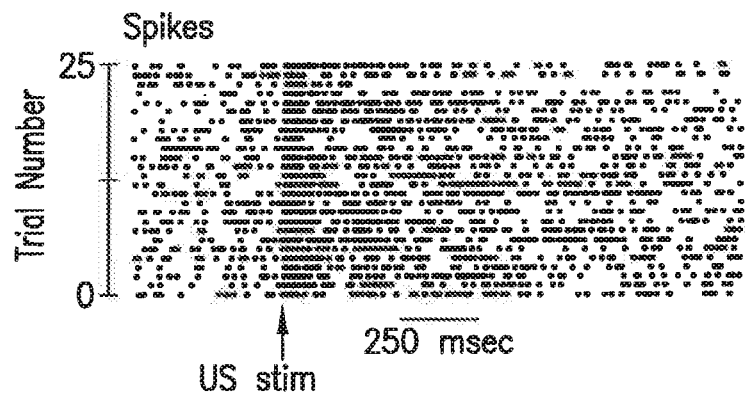
FIG. 23A shows a spike raster plot that illustrates an increase in cortical spikes as a function of time in response to ultrasound stimulation.
Figure 23B:
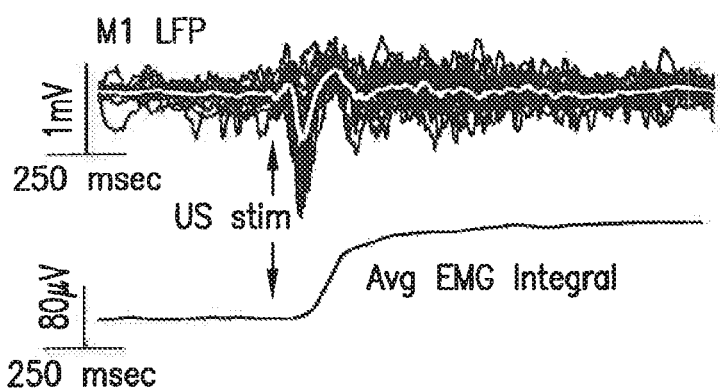
FIG. 23B shows extracellular neuronal activity traces recorded in response to ultrasound stimulation.

Table 2 provides an overview of the US stimulus waveforms used in this Example. In Table 2, a single asterisk (*) indicates that standard US waveforms were used during the investigation. In Table 2, a double asterisk (**) indicates relatively high-intensity US waveforms were used to assess safety.

of cortical spiking in a temporally precise manner (ANOVA, $F_{19, 480}$=69.72, P<0.001; FIG. 18C and FIG. 23). Delivery of US stimulus waveforms to M1 produced local field potentials (LFP) with mean amplitudes of −350.59±43.34 μV (FIG. 18C). Application of tetrodotoxin (TTX) to the motor cortex blocked US-evoked cortical activity, indicating that transcranial US elicits action potentials mediated by voltage-gated sodium channels (FIG. 18C; raw control (black), average control (blue), and average TTX (red)).

Figure 24A:
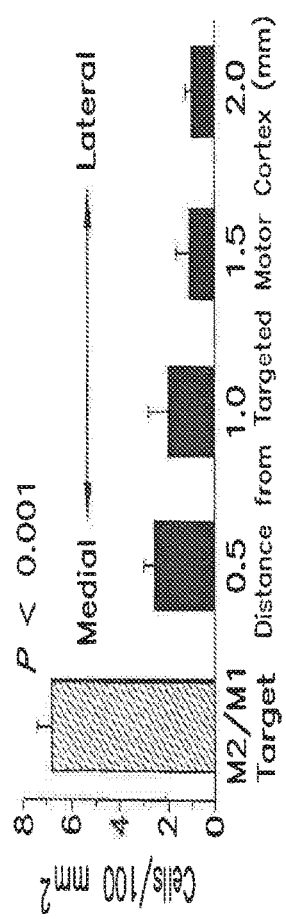
FIG. 24A shows a histogram illustrating the mean density of c-fos positive cells from ultrasound-stimulated hemispheres as a function of targeted region.
Figure 24B:
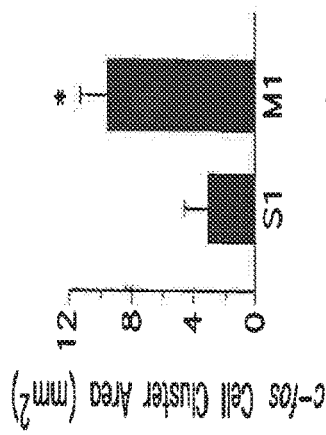
FIG. 24B shows a histogram illustrating the mean area of clusters containing c-fos positive cells.
Figure 25:
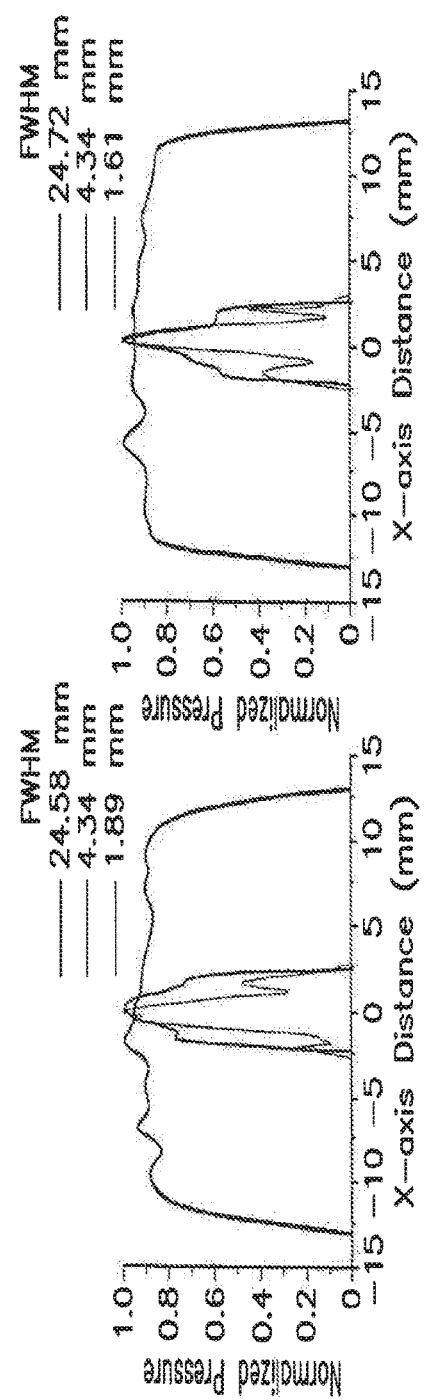
FIG. 25 shows normalized pressure profiles following ultrasound stimulation.

Example 7: Determination of the Area of Intact Motor Cortex Activated by Ultrasound Using a c-fos labeling technique, studies were conducted in order to determine the area of motor cortex activated by laterally focused US stimulus waveforms (n=5 mice). An ANOVA revealed a significantly higher density of activated cells in the targeted motor cortex compared to adjacent untargeted motor and primary somatosensory (S1) cortex ($F_{4,45}$=17.1, P<0.001; FIG. 24A). Further densiometric analyses revealed significantly larger clusters of activated cells in targeted M1 compared to the untargeted and adjacent S1 (targeted M1 cluster area=9.45±1.81 mm$^2$, untargeted S1 cluster area=3.01±1.54 mm$^2$; T-test, P<0.05; FIG. 24B). The size of the activated area is consistent with the implemented US wavelengths (≈3-6 mm in brain tissue), as well as the area of acoustic pressure fields produced by the laterally restricted spatial envelope of US stimulus waveforms generated by focusing guides (≈8-10 mm$^2$; FIG. 25).

Multi-dimensional pressure output profiles obtained using a 25 mm planar US transducer alone (top) and with an attached 5 mm diameter focusing guide (middle) or an attached 5 mm guide tapered to a 2 mm output diameter (bottom) used to differentially target US stimulus waveforms to the motor cortex were obtained. FIG. 25 shows the

TABLE 2

Low-Intensity Transcranial Ultrasound (US) Waveform Properties used to Stimulate Intact Mouse Motor Cortex

| f | c/p | PD (msec) | PRF (KHz) | Np | US Stim length (sec) | $P_r$ (MPa) | $P_{II}$ (mJ/cm$^2$) | $I_{SPPA}$ (W/cm$^2$) | $I_{SPTA}$ (mW/cm$^2$) | MI |
|---|---|---|---|---|---|---|---|---|---|---|
| *0.250 | 120 | 0.480 | 1500 | 80 | 0.053 | 0.089 | 0.082 | 0.167 | 123.40 | 0.18 |
| 0.250 | 80 | 0.320 | 1200 | 100 | 0.083 | 0.088 | 0.051 | 0.161 | 60.78 | 0.18 |
| 0.350 | 200 | 0.571 | 1500 | 40 | 0.027 | 0.071 | 0.044 | 0.077 | 65.98 | 0.12 |
| 0.350 | 180 | 0.514 | 1500 | 80 | 0.053 | 0.072 | 0.040 | 0.077 | 59.38 | 0.12 |
| *0.350 | 80 | 0.229 | 2500 | 150 | 0.060 | 0.070 | 0.017 | 0.075 | 42.90 | 0.12 |
| 0.350 | 120 | 0.343 | 1500 | 80 | 0.053 | 0.071 | 0.027 | 0.076 | 40.76 | 0.12 |
| 0.350 | 125 | 0.357 | 1200 | 100 | 0.083 | 0.071 | 0.027 | 0.076 | 32.61 | 0.12 |
| 0.350 | 100 | 0.286 | 1500 | 80 | 0.053 | 0.072 | 0.022 | 0.076 | 32.40 | 0.12 |
| 0.350 | 80 | 0.229 | 1200 | 100 | 0.083 | 0.070 | 0.017 | 0.075 | 20.59 | 0.12 |
| 0.425 | 100 | 0.235 | 3000 | 1000 | 0.333 | 0.082 | 0.025 | 0.107 | 74.97 | 0.13 |
| 0.425 | 80 | 0.188 | 3000 | 150 | 0.050 | 0.083 | 0.019 | 0.103 | 57.80 | 0.13 |
| 0.425 | 80 | 0.188 | 3000 | 800 | 0.267 | 0.083 | 0.019 | 0.103 | 57.80 | 0.13 |
| 0.425 | 80 | 0.188 | 2750 | 200 | 0.073 | 0.083 | 0.019 | 0.103 | 52.98 | 0.13 |
| 0.425 | 80 | 0.188 | 1500 | 200 | 0.133 | 0.083 | 0.019 | 0.103 | 28.90 | 0.13 |
| 0.500 | 150 | 0.300 | 2500 | 150 | 0.060 | 0.097 | 0.065 | 0.225 | 162.74 | 0.14 |
| **0.500 | 225 | 0.450 | 1500 | 80 | 0.053 | 0.092 | 0.095 | 0.216 | 142.20 | 0.13 |
| 0.500 | 200 | 0.400 | 1500 | 40 | 0.027 | 0.095 | 0.087 | 0.223 | 130.17 | 0.13 |
| 0.500 | 125 | 0.250 | 1500 | 100 | 0.067 | 0.097 | 0.054 | 0.225 | 80.78 | 0.14 |
| *0.500 | 100 | 0.200 | 1500 | 80 | 0.053 | 0.097 | 0.043 | 0.228 | 64.53 | 0.14 |
| 0.500 | 80 | 0.160 | 1200 | 100 | 0.083 | 0.097 | 0.034 | 0.229 | 40.81 | 0.14 |

The influence of US stimulus waveforms was examined on intact brain activity by recording multi-unit activity (MUA) from the primary motor cortex (M1) of mice (n=6). Low-intensity US stimulus waveforms focally restricted to unilateral M1 induced a significant increase in the frequency normalized pressure profiles obtained with a 25 mm planar transducer (black) and with a 5 mm (blue) or tapered 2 mm output diameter (red) focusing guide attached are illustrated for X (top) and Y (bottom) planes. The full-width half-maximum (FWHM) values are illustrated for each plane.

Example 8: Determination of Effects of Ultrasound on Intact Central Nervous System Activity To determine the effects of low-intensity transcranial US on intact central nervous system activity (CNS) activity, its influence on known descending corticospinal motor circuits was investigated. Fine-wire electromyogram (EMG) recordings of muscle activity in response to the transcranial delivery of US stimulus waveforms to intact motor cortex were acquired (n=43 mice; FIGS. 18D and 18E). For example, in FIG. 18D, the schematic (top) illustrates the experimental approach to stimulating descending corticospinal tracts with transcranial ultrasound. Raw electromyogram (EMG) traces (bottom) in response to right transcranial M1 stimulation illustrate US-evoked activity of the left triceps brachii. FIG. 18E shows that raw (left) and full-wave rectified (FWR; right) EMG traces for a spontaneous (top) and average (10 trials) US-evoked (bottom) event. The duration of the US stimulus waveform (black), average US-evoked EMG trace (grey), and EMG integral (green) are superimposed at lower-right.

Descending corticospinal motor circuits were successfully stimulated in 90.3% of the cases. Bilateral US stimulation of motor cortex produced bilateral motor activation of several muscle groups. Transcranial US delivered through focusing guides, however, led to selective activation of muscle groups depending on the cortical region targeted. For example, targeted unilateral stimulation of right M1 triggered left forelimb muscle contractions sufficient to induce paw movements (FIG. 18D). In most cases, the location of US focusing guides over motor cortex was changed to produce differential movement behaviors (whisker movements compared to forelimb and tail movements. Although the spatial resolution for focusing US is currently limited by the acoustic wavelength employed, recent advances in focusing US with adaptive optics permit US to gain spatial resolutions below the diffraction limits as has been achieved in light microscopy.

Figure 19A:
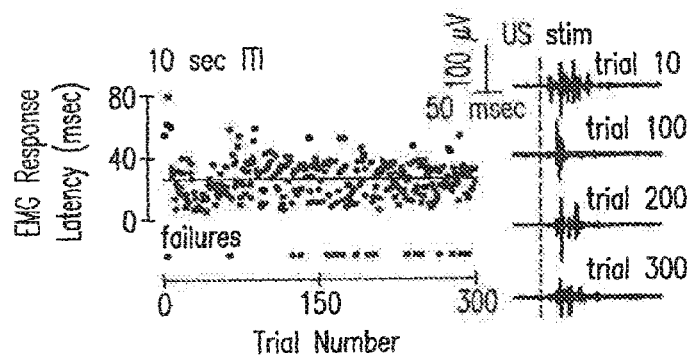
FIG. 19A shows plot of the electromyogram response latency of left triceps brachii in response to right M1 activation as function of repetitive trial number.
Figure 19B:
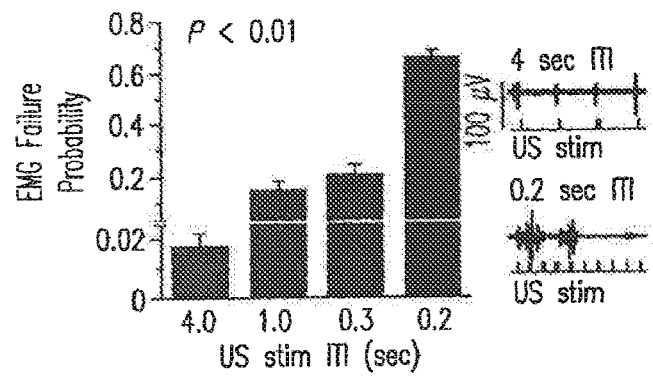
FIG. 19B shows electromyogram failure probability histograms for four progressively decreasing ITIs.
Figure 19C:
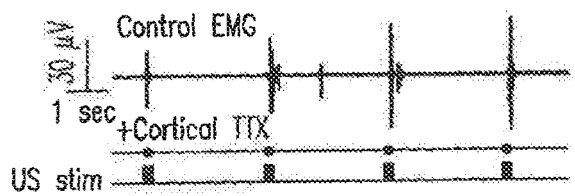
FIG. 19C shows raw electromyogram traces illustrating application of tetrodotoxin (TTX) to the motor cortex blocks ultrasound-evoked descending corticospinal circuit activity.

Unilateral US stimulation of motor cortex triggered EMG activity in the contralateral triceps brachii muscle (n=17 mice) with a mean response with latency of 20.88±1.46 msec and was consistent across trials. FIG. 19A shows EMG response latency of left triceps brachii in response to right MI activation is plotted as a function of repetitive trial number (left) for a 10 sec ITI. Individual US-evoked raw EMG traces are shown for different trials (right). Bilateral stimulation of motor cortex to trigger tail movements was similarly consistent and elicited EMG activity in the lumbosacrocaudalis dorsalis lateralis muscle (n=26 mice) with a response latency of 22.65±1.70 msec. These response latencies are consistent with the observations of others using optogenetic and electrical methods to stimulate motor cortex. The repeatability of motor activation functioned as the inter-trial interval (ITI) between US-stimulus events decreased was studied next. An ANOVA revealed the EMG failure probability significantly ($F_{3,\ 92}$=120.40; P<0.001) increased as the ITI was reduced. FIG. 19B shows EMG failure probability histograms are shown for four progressively decreasing ITIs (left). Raw US-evoked EMG traces are shown for two different ITI times (right). To determine if US-evoked cortical activity drives the EMG response, in some experiments tetrodotoxin (TTX) was applied to the motor cortex during stimulation trials. It was observed that the application of TTX to motor cortex blocked EMG activity, which indicates transcranial US elicits cortical action potentials to stimulate motor circuit activity and peripheral muscle contractions (n=4 mice). FIG. 19C shows raw EMG traces illustrating that application of TTX to the motor cortex blocks US-evoked descending corticospinal circuit activity.

Example 9: Evaluation of the Effects of Ultrasound on Brain Temperature

To evaluate the influence of low-intensity pulsed ultrasound on brain temperature, however, the temperature of motor cortex was monitored during transcranial ultrasound transmission while varying acoustic intensity and pulse duration (PD) times. Equations for estimating thermal absorption of US in biological tissues predict that 0.5 MHz US pulses exerting a $p_r$ of 0.097 MPa for a PD of 0.57 msec can induce a temperature increase of $2.8 \times 10^{-6}$° C. in brain. Briefly, the maximum temperature change ($\Delta T_{max}$) is estimated to be:

$$\Delta T_{max} = \frac{Q \Delta t}{C_V}$$

where $\Delta t$ is the pulse exposure time, where $C_v$ is the specific heat capacity for brain tissue≈3.6 J/g/K and where Q is the rate at which heat is produced defined by (Nyborg 1981):

$$Q = \frac{\alpha p_0^2}{p0}$$

where p is the density of the medium, c is the speed of sound in the medium as described above, where α is the absorption coefficient of brain (≈0.03 Np/cm for 0.5 MHz ultrasound), and $p_0$ is the pressure amplitude of US stimulus waveforms.

In some experiments, prior to transmitting transcranial ultrasound waveforms into intact brains, a small craniotomy (d≈2 mm) was performed on mouse temporal bone. Following removal of dura, a 0.87 mm diameter thermocouple (TA-29, Warner Instruments, LLC, Hamden, Conn., USA) was inserted into motor cortex through the cranial window. The thermocouple was connected to a monitoring device (TC-324B, Warner Instruments), which was connected to the Digidata 1440A in order to record temperature (calibrated voltage signal=100 mV/° C.) using pClamp connected to a PC. To facilitate off-line analyses, TTL signal markers indicated the onset of US stimulus waveforms.

Figure 19D:
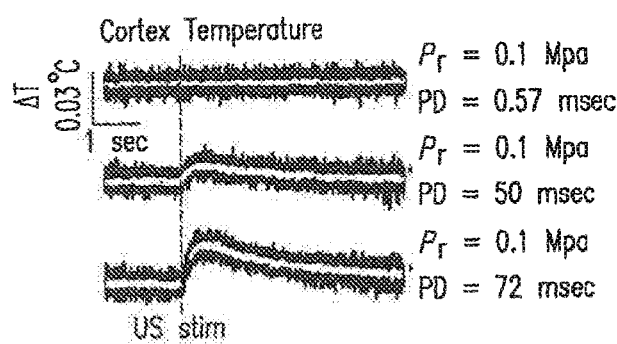
FIG. 19D shows temperature recordings from M1 in response to transmission of ultrasound waveforms.

All US stimulus waveforms used had $p_r$ values <0.097 MPa and PD times ≤0.57 msec. None of the US waveforms used to stimulate cortical activity elicited a significant change in cortical temperature within the resolution limits (FIG. 19D). Under these experimental conditions, US pulses with $p_r$ values of 0.1 MPa and PD times >50 msec were required to produce a temperature change (ΔT) of≈0.02° C. FIG. 19D shows the raw (black) and average (grey) temperature recordings from M1 in response to transmission of US waveforms with different intensity characteristics. FIG. 19D illustrate stimulus waveforms (top) do not produce an increase in cortical temperature as observed with higher intensity waveforms (middle and bottom). These observations bolster the idea of a predominantly mechanical (non-thermal) mechanism of action and highlight the safety margins of stimulus waveforms.

Figure 19E:
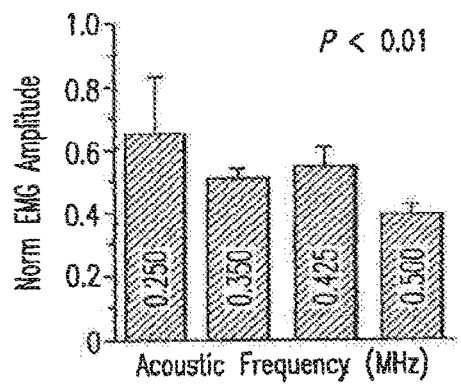
FIG. 19E shows normalized ultrasound-evoked electromyogram amplitude histograms plotted for four ultrasound frequencies.
Figure 19F:
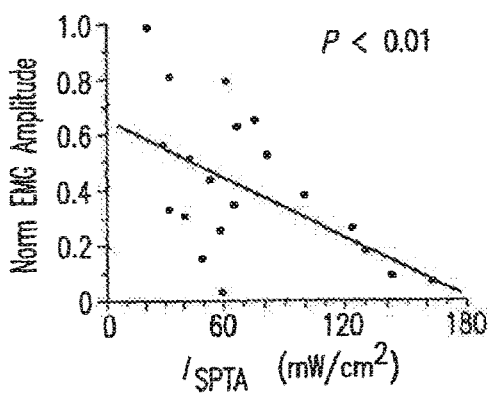
FIG. 19F shows normalized ultrasound-evoked electromyogram amplitudes plotted as function of ultrasound intensities.

Example 10: Determination of Effects of Variations of the Acoustic Frequency and Intensity of Ultrasound on Neuronal Circuit Activity Experiments were designed in order to determine how the acoustic frequency and intensity of US stimulus waveforms influenced neuronal circuit activity. The effect of four different US frequencies (0.25, 0.35, 0.425, 0.500 MHz) on EMG amplitudes produced by triceps brachii in mice was examined (n=20). A two-way ANOVA revealed a significant main effect of US frequency on EMG amplitudes ($F_{3,\ 1085}$=3.95, P<0.01) whereby lower frequencies produced more robust EMG responses (FIG. 19E). To better understand how the intensity of US stimulus waveforms influences neuronal activity, focus was put on the acoustic intensity measure $I_{SPTA}$ since it takes into account both the pulse intensity integral (PII) and pulse repetition frequency (PRF). Across the range of acoustic frequencies examined above, 20 distinct waveforms having different $I_{SPTA}$ values were studied (Table 2). The two-way ANOVA also revealed a significant main effect of $I_{SPTA}$ on EMG amplitude ($F_{19,\ 1085}$=9.78, P<0.001; FIG. 19F), indicating lower $I_{SPTA}$ values triggered larger EMG amplitudes. Specifically, FIG. 19F shows the normalized US-evoked EMG amplitudes are plotted as a function of US intensities (ispTA) produced by 20 distinct stimulus waveforms. In FIG. 2G, the interaction between US intensity ($I_{SPTA}$) and US frequency is plotted as a function of normalized EMG amplitudes and the two-way ANOVA also revealed a significant frequency by intensity interaction ($F_{3,\ 1085}$=7.25, P<0.01). Collectively, these data indicate low-intensity, low-frequency transcranial US is effective at driving cortical circuit activity in intact animals.

Example 11: Characterization of the Intensity of Ultrasound Stimulus Waveforms

To characterize the intensity characteristics of pulsed US stimulus waveforms, voltage traces produced by US pressure waves were recorded using a calibrated needle hydrophone (HNR 500, Onda Corporation, Sunnyvale, Calif., USA) and an Agilent DS06012A 100 MHz digital oscilloscope connected to a PC. To confirm transducers were operating at the intended acoustic frequency, an FFT was performed on hydrophone voltage traces recorded in response to US waveforms. Using a xyz micromanipulator (MP-225, Novato, Calif., USA) to scan hydrophone placement across US fields, all intensity measurements were made in the far-field by recording pressures transmitted through fresh ex vivo heads (intact hair, skin, skull, and dura) using focusing guides. More specifically, intensity measurements were made from targeted points corresponding to motor cortex 0.8 mm below the skull surface, as well as at the same distance from the transducer face without transmitting through ex vivo heads (FIG. 22). The transcranial US waveforms were transmitted to intact motor cortex from US transducers using custom-designed lateral focusing guides consisting of 5 mm diameter polyethylene tubing or 5 mm diameter tubing tapered to a 2 mm diameter output opening (FIG. 25). Focusing guides were filled with ultrasound coupling gel.

The intensity characteristics of US waveforms were calculated based on technical standards and equations published by the American Institute of Ultrasound Medicine (AIUM) and the National Electronics Manufacturers Association (NEMA) (NEMA 2004). The pulse intensity integral (PII) was defined as:

$$PII = \int \frac{p2(t)}{Z_0} dt$$

where p is the instantaneous peak pressure, $Z_0$ is the characteristic acoustic impedance in Pa s/m defined as pc where p is the density of the medium, and c is the speed of sound in the medium. The p is estimated to be 1028 kg/m³ and c to be 1515 m/s for brain tissue based on previous reports (Ludwig 1950). The spatial-peak, pulse-average intensity ($I_{SPPA}$) was defined as:

$$I_{SPPA} = \frac{PII}{PD}$$

where PD is the pulse duration defined as (t)(0.9PII–0.1PII) 1.25 as outlined by technical standards established by AIUM and NEMA (NEMA 2004). The spatial-peak temporal-average intensity ($I_{SPTA}$) was defined as:

$$I_{SPTA}=PII(PRF)$$

where PRF is equal to the pulse repetition frequency in hertz. The mechanical index (MI; see Table 2) was defined as:

$$MI = \frac{p_r}{\sqrt{f}}$$

Example 12: Examination of the Effects of Ultrasound on Cellular Infrastructure

Several experimental approaches were implemented to examine the effects of ultrasound on cellular infrastructure and cerebrovasculature. A relatively high-intensity US stimulus waveform (see Table 2) repeated at an ITI of 10 sec for >20 min was delivered to motor cortex prior to all such experiments. Quantitative transmission electron microscopy was used to examine the ultrastructure of excitatory synapses in motor cortex. Tissue was prepared for electron microscopy and imaging was performed using standard procedures. Following stimulation, animals were transcardially perfused with 2% glutaraldehyde, 2.5% formaldehyde in sodium cacodylate buffer. Brains were subsequently removed and post-fixed in 2% glutaraldehyde, 2.5% formaldehyde in sodium cacodylate buffer overnight in 4° C. Following post-fixation, brains were washed 3 times in sodium cacodylate buffer and sliced in into 300 μm sections using a vibratome. Slices containing motor cortex were identified and washed 5 times (15 min each) sodium cacodylate buffer with a final wash overnight. Secondary fixation was performed the next day with 0.2% osmium textroxide in sodium cacodylate buffer for 1 hr at room temperature. Sections were washed 3 times in sodium cacodylate buffer and 3 times in water before being bock-stained overnight at 4° C. with 0.25% uranyl acetate. Samples were dehydrated in a 20%, 40%, 60%, 80%, and 100% graded ethanol series (3 washes each) and finally by washing two times in 100% acetone. Samples were infiltrated with 25%, 50%, 75% and 100% in Spur's resin (three incubations each) during the next 3 d before being flat embedded on Teflon coated glass slides and polymerized overnight at 60° C.

Motor cortex was then identified under dissecting microscope and trimmed out for block mounting. Trimmed sections containing motor cortex were mounted on resin blocks, trimmed again and then ultra-thin sectioned at 70 nm on an ultramicrotome (Leica Ultra Cut R, Leica Microsystems, Inc., Bannockburn, Ill., USA). Samples were collected on formvar coated copper slot grids and post-stained with 1% uranyl acetate in ethanol and Sato's lead citrate for 5 and 3 min respectively. Samples were imaged at 80 kV on a Phillips CM12 transmission electron microscope and images acquired with a Gatan CCD camera (model 791, Gatan, Inc., Warrendale, Pa., USA). Images were acquired at 8,000× for analysis of overall ultrastructure, 19,500× for analysis of synaptic density and 40,000× quantitative analysis of synapse specific parameters.

Figure 20A:
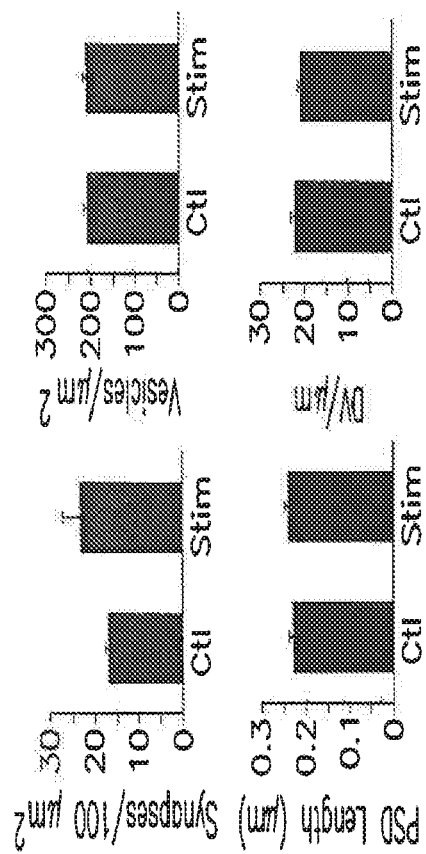
FIG. 20A shows histograms for mean synaptic density, mean axonal bouton synaptic vesicle density, mean postsynaptic density length, and mean number of docked vesicles occupying active zones.

FIG. 20A also shows histograms (right) from control (n=5) and stimulated (n=6) mice for mean synaptic density (top-left), mean axonal bouton synaptic vesicle density (top-right), mean PSD length (bottom-left), and mean number of DV occupying active zones (bottom-right). An independent samples T-test revealed no significant difference in the density of synapses between groups (control=16.59±0.81 synapses/100 um$^2$ from 2.3 mm$^2$ cortex, ultrasound stim=22.99±4.07 synapses/100 um$^2$ from 4.2 mm$^2$ cortex; P>0.10; FIG. 20A). Further T-tests revealed no significant differences in the postsynaptic density (PSD) length (control=0.225±0.009 μm from 99 synapses, ultrasound stim 0.234±0.009 um from 130 synapses; P>0.10), the area of presynaptic terminals (control=0.279±0.02 μm$^2$, ultrasound stim=0.297±0.02 μm$^2$; P>0.10), the density of vesicles in presynaptic boutons (control=206.89±9.52 vesicles/μm$^2$, ultrasound stim=209.85±8.14 vesicles/μm$^2$; P>0.10), or the number of docked vesicles (DV) occupying active zones (control=21.71±0.91 DV/μm, ultrasound stim=20.26±0.61 DV/μm; P>0.10) between treatment groups as shown in FIG. 20A. Overall, there were no qualitative differences in the ultrastructure of cortical neuropil between treatment groups.

Figure 20B:
FIG. 20B shows histograms for the mean density of cleaved-caspase 3 positive glial cells and neurons in the motor cortex of control and ultrasound-stimulated hemispheres.

A change in the density of apoptotic glial cells (control=0.26±0.02 cells/100 mm$^2$ from 17.0 cm$^2$ cortex from 5 mice, ultrasound stim=0.22±0.02 cells/100 mm$^2$ from 15.6 cm$^2$ cortex from 5 mice; P>0.05) or apoptotic neurons (control=0.032±0.02 cells/100 mm$^2$, ultrasound stim=0.067±0.02 cells/100 mm$^2$; P>0.10) in response to ultrasound stimulation as assayed by quantitative immunocytochemistry of cleaved-Caspase-3 was not observed (FIG. 20B). Confocal images of NeuN and cleaved-Caspase 3 positive cells were obtained from 50 μm sections of motor cortex from control and US stimulated brain hemispheres at low- and high-magnification. Histograms illustrate the mean density of cleaved-Caspase 3 positive glial cells (top) and neurons (bottom) in the motor cortex of control and US-stimulated hemispheres.

Example 13: Examination of the Effects of Ultrasound on Cerebrovasculature

In another set of experiments the integrity of cerebrovasculature was examined. Prior to experiments, mice received an intravenous administration of fluorescein isothiocyanate-dextran (10 kDa), which does not cross the blood-brain barrier (BBB) under normal conditions. During post-stimulation analysis of targeted cortex using confocal microscopy, it was observed that US stimulus waveforms did not produce damage to cerebrovasculature or disrupt the blood-brain barrier (control=353.35 cm$^2$ cortical area and 17.96 cm vasculature length examined from 5 mice, ultrasound stim=352.96 cm$^2$ cortical area and 18.34 cm vasculature length examined from 5 mice.

In a separate set of experiments, intravenous fluorescein-isothiocyanate-dextran was co-administered with an ultrasound-microbubble contrast agent (Optison®) known to elicit BBB disruption during ultrasound administration to intact brain. Results from these positive control experiments (n=3 mice) confirmed the ability to detect cerebrovasculature damage or BBB disruption had it occurred in response to ultrasound stimulus waveforms. Confocal images of TO-PRO-3 labeled cells and fluorescein-dextran filled cerebrovasculature were obtained from 75 μm sections of motor cortex from a control and ultrasound-stimulated brain. A positive control ultrasound-stimulation was performed in the presence of Optison®, an ultrasound-microbubble contrast agent known to elicit cavitationally-mediated vasculature damage.

Figure 20C:
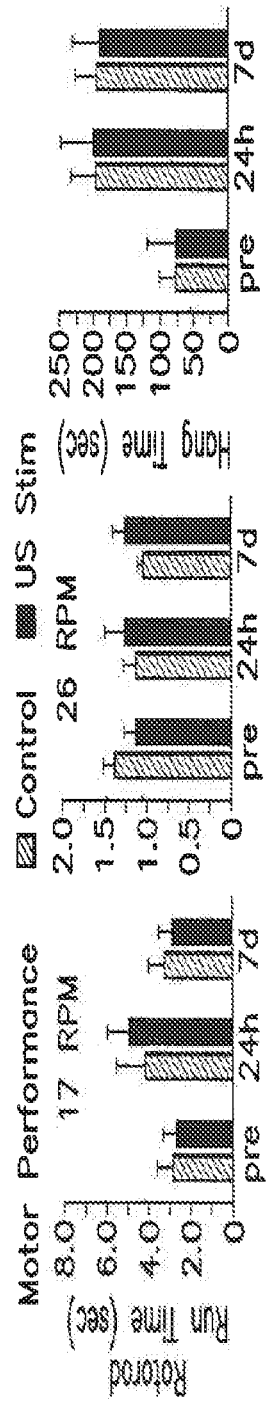
FIG. 20C shows histograms for mean rotorod running times and mean wire hang times at 24 h pre-treatment and 24 h and 7 d post-treatment.

Although no histological evidence for tissue damage was found, experiments were conducted in order to determine if transcranial US stimulation of motor cortex produced impaired motor behaviors. The day before stimulation, 24 hours post-stimulation, and again 7 days post-stimulation, a series of experiments designed to assay motor function was performed. A repeated measures ANOVA revealed no significant effect of US stimulation (n=9 mice) compared to sham-treated controls (n=9 mice) on motor behavior as determined by a rotorod running task, which was designed to evaluate coordination, balance and equilibrium ($F_{1,9}$=0.211, P>0.1; FIG. 20C). Motor function and grip strength was also measured by subjecting mice to wire-hanging task. Again, repeated measures ANOVA revealed no significant group effect on hang time ($F_{1,9}$=0.05; P>0.1; FIG. 20C). During daily monitoring, no differences were observed in feeding behavior, grooming behavior, or startle reflexes between US stimulated mice and sham controls. Based on these observations, the conclusion is that low-intensity transcranial US provides a safe and noninvasive mode of stimulating cortical activity.

Example 14: Examination of the Effects of Ultrasound on Motor Behavior

In those experiments utilizing behavioral assays, a series of behavioral analyses were performed to assess the influence of US stimulation of motor cortex on coordination, balance, equilibrium, and grip strength. Ultrasound stimulated and sham-treated control mice were subjected to behavioral testing using a rotorod task and a wire-hanging task. For both groups, pre-treatment baseline testing was conducted on both tasks 24 h prior to treatment. On treatment day, sham-treated controls and US stimulated animals were anesthetized with ketamine/zylazine and their hair was trimmed as described above. Following ultrasound stimulation or sham-treatment, motor skill testing was administered on rotorod and wire-hanging tasks again at 24 h and 7 days later. On each testing day, animals ran on the rotorod (25.4 cm circumference, 10.8 cm wide rod) until failure (time in seconds before falling from rotorod) for 5 trials each at two speeds (17 and 26 RPM). Following rotorod trials, animals performed wire-hanging tests until failure time (time in seconds before falling from suspended wire) for 5 trials. In the wire-hanging tasks, mice were hung by their forepaws from a wire (76.2 cm long×0.16 cm diameter) suspended 51.0 cm above the ground. Data from each of the five trials were averaged for each task on each test day.

Example 15: Examination of the Effects of Acoustic Pressure on Brain Fluids

The mechanical wave properties of acoustic pressure affect these brain fluids. With respect to the local actions of US, the extracellular space can be considered a continuous medium. An examination of the Knudsen number ($Kn=\lambda/L$, where λ is the molecular mean free path length and L is the characteristic length scale for the physical boundaries of interest). Thus, with regard to the effects of US on the dynamics of cerebrospinal fluid (CSF) in the extracellular space of the brain, the λ, of water ($\approx 10^{-11}$ m) provides a reasonable estimate for that of CSF (especially considering that large molecular proteins found in CSF and intracranial pressure would further reduce λ, values). Then taking the extracellular space between cells in the brain (L) to be $\approx 10^{-8}$ m, a Kn value of 0.001 is calculated. When Kn<1, continuum mechanics formulations (opposed to quantum mechanics for which Kn»1) are valid and can be applied. Furthermore, the combination of a continuous extracellular space with the presence of both Newtonian (CSF) and non-Newtonian (viscoelastic cell membranes) fluids in brain supports this position. US can noninvasively modulate neuronal activity through a combination of pressure/fluid/membrane actions involving stable cavitation and acoustic streaming (microjet formation, eddying, and turbulence) in addition to acoustic radiation force, shear stress, Bernoulli effects, and other fluid-mechanical consequences, which stem from small acoustic impedance mismatches (boundary conditions) between lipid bilayers, surrounding intra/extracellular fluids, and interleaved cerebrovasculature.

For example, Table 3 presents the speed of sound, media density, and acoustic impedance in brain and its surrounding tissues. The speed of sound (c) varies in different media (biological fluids including tissues in this case) depending on the bulk modulus and density (p) of a given medium. The physical properties of the medium determine its characteristic acoustic impedance (Z) defined as Z=pc. An acoustic impedance mismatch is defined as the difference in Z across two media ($Z_2-Z_1$) and establishes a boundary condition. Acoustic impedance mismatches at cellular interfaces underlie many bioeffects of US and serve as the basic principle enabling diagnostic imaging by causing US to be differentially reflected and transmitted. When considering how US behaves and influences brain activity, the transmission, absorption, reflection, refraction, scattering, and attenuation coefficients of US for given media are important factors to consider. The boundary conditions established by cellular interfaces mediate fluid behaviors, which can influence neuronal activity.

TABLE 3

Approximate Values for Speed of Sound, Media Density, and Acoustic Impedance

| Tissue/Media | c (m/s) | P (Kg/m³) | Z(Kg/s/m²) × 10⁶ |
|---|---|---|---|
| Air | 333 | 0.0012 | 0.0004 |
| Water | 1480 | 1000 | 1.48 |
| CSF | 1515 | 1006 | 1.52 |
| Skull | 4080 | 1912 | 7.80 |
| Brain | 1505-1612 | 1030 | 1.55-1.66 |
| Fat | 1446 | 920 | 133 |
| Artery | 1532 | 1103 | 1.69 |
| Blood | 1566 | 1060 | 1.66 |
| Muscle | 1542-1626 | 1077 | 1.65-1.74 |

Figure 26A:
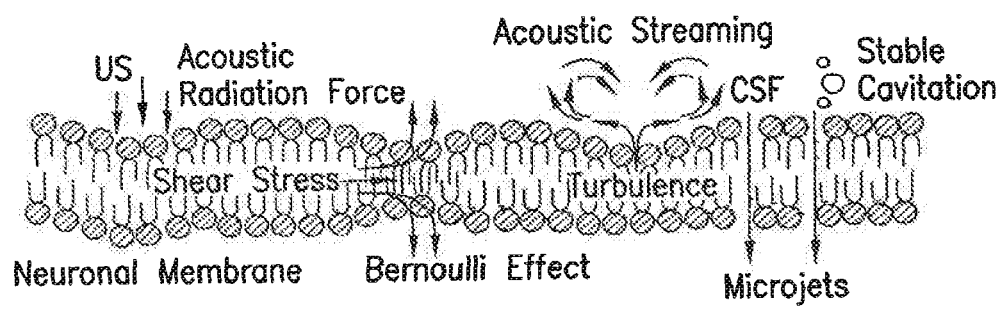
FIG. 26A shows an illustration depicting some of the proposed fluid mechanical actions by which ultrasound can modulate neuronal activity.
Figure 26B:
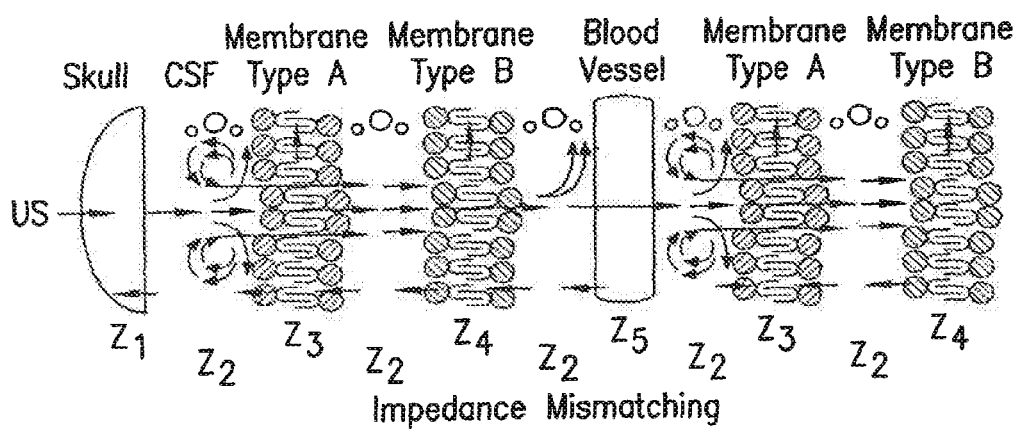
FIG. 26B shows an illustration of a composite model of brain tissue, where different cellular interfaces establish boundary sites having different properties due to acoustic impedance mismatches.

Regarding the mechanisms that underlie ultrasonic neuromodulation, experiments illustrate (i) the viscoelastic responses of neurons produced by US, (ii) the presence of acoustic streaming and turbulent flow produced compressible bubbles approximating the size of neurons, and (iii) the presence of stable cavitation in response to US pulses that increase neuronal activity. For example, using confocal line scans illustrate the influence of radiation force produced by longitudinal ultrasound on CA1 pyramidal neurons in an acute hippocampal slice stained with a fluorescent membrane dye (DiO). Membrane compression in response to US pulses can be detected by an increase in fluorescence intensity within the indicated regions of interest. The effects of shear stress can be observed by elevated pixel intensities extending vertically beyond the highlighted regions of interest. A horizontal smearing of elevated pixel intensities following the termination of ultrasound pulses illustrates millisecond membrane relaxation times and neuronal viscoelasticity. Furthermore, time-lapsed confocal images of microbubbles in a fluorescent dye-containing solution serve to illustrate acoustic streaming, microjet formation, and fluid turbulence in response to ultrasound. Similarly, experiments yielded examples of a small microbubble undergoing stable cavitation and a larger microbubble undergoing inertial cavitation before exploding. FIG. 26A shows an illustration depicting some of the fluid mechanical actions by which US can modulate neuronal activity. FIG. 26B shows a composite model of brain tissue, where different cellular interfaces establish boundary sites having different properties due to acoustic impedance mismatches.

In those experiments utilizing histological investigations of stimulated and unstimulated brain regions of mice receiving transcranial US stimulation of motor cortex, the tissue was prepared as follows. Mice were transcardially perfused using 4% paraformaldehyde in PBS. Mouse brains were removed and post-fixed in 4% paraformaldehyde overnight. Coronal slices of stimulated and adjacent unstimulated motor cortex were then made using a vibratome or a cryotome. Transmitted light microscopy analysis of electrolytic lesions made following extracellular recordings were performed using 30 m thick coronal cryosections stained with cresyl violet.

Following transcardial perfusion and postfixation, coronal sections (50 µm) were prepared using a vibratome and the brains of some mice unilaterally stimulated by US waveforms. Brain sections were double-labeled by fluorescence immunocytochemistry as similarly described. Brain sections were labeled with antibodies against cleaved Caspase-3 (1:250; Asp 175-9661, Cell Signaling Technology, Beverly, Mass., USA) or c-fos (1:250; SC-253, Santa Cruz Biotechnology, Inc., Santa Cruz, Calif., USA) and NeuN (1:1000, MAB377, Millipore, Billerica, Mass., USA). Following primary antibody incubation, sections were washed and incubated in appropriate Alexa Fluor 568 (1:500; Invitrogen, Carlsbad, Calif., USA) and Alexa Fluor 633 (1:500; Invitrogen) secondary antibodies. Sections were then washed 3 times in PBS, mounted on glass slides, and coverslipped with fluorescence mounting solution (H-1000; Vector Laboratories, Burlingame, Calif., USA). Two-channel fluorescence images were acquired on an Olympus Fluoview FV-300 laser-scanning confocal microscope (Olympus America, Inc., Center Valley, Pa., USA).

Prior to US stimulation trials, some animals received an intravenous infusion of 5% fluorescein isothiocyanate-dextran (10 kDa; Sigma, St. Louis, Mo., USA) in a 0.9% sodium chloride solution (0.35 mL), which does not cross the blood-brain barrier (BBB) under normal conditions (Kleinfeld 1998). Following US stimulation, mice were euthanized using $CO_2$ inhalation and rapidly decapitated to prevent loss of fluorescein loss from the vasculature. Brains were rapidly removed and following overnight fixation in 4% paraformaldehyde, coronal sections (75 µm) were prepared using a vibratome. Floating sections were then labeled with TO-PRO-3 (1:1000; Invitrogen) to identify cell bodies. Following washing and mounting as described above, the cerebrovasculature of stimulated and unstimulated motor cortex was examined using confocal microscopy. In a separate set of mice, the detection of BBB or cerebrovascular damage using the above described approach was confirmed. In these positive control experiments mice received an intravenous infusion of 5% fluorescein isothiocyanate-dextran in conjunction with an ultrasound-microbubble contrast agent (Optison®; GE Healthcare, Piscataway, N.J., USA) known to elicit BBB disruption during US administration to intact brain (Raymond 2008). Brain sections were prepared processed similar to described above and imaged using confocal microscopy.

Figure 23C:
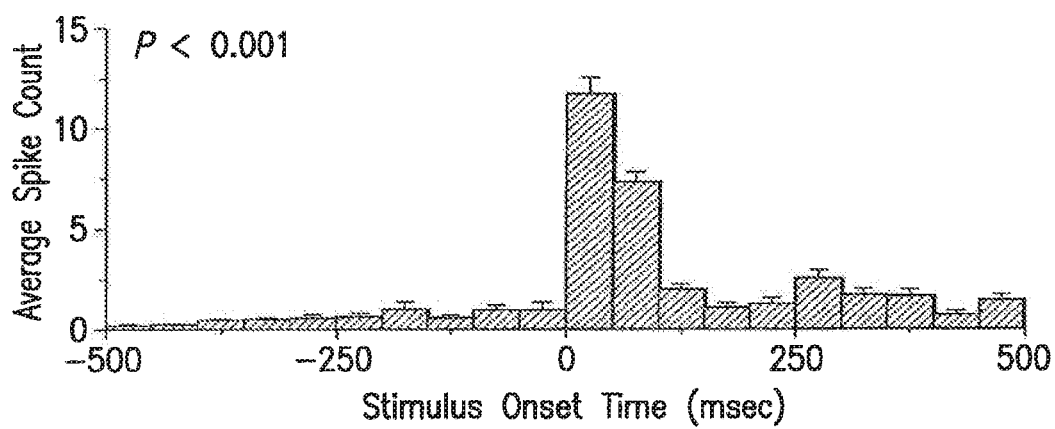
FIG. 23C shows a post-stimulus time histogram illustrating the average multi-unit activity (MUA) spike count before and after ultrasound stimulation.

In those experiments utilizing extracellular recordings, extracellular activity was recorded using standard approaches with tungsten microelectrodes ($\approx 1$ M$\Omega$, FHC, Inc., Bowdoin, Me., USA). Anesthetized mice were placed in a Cunningham mouse stereotax and a craniotomy (d$\approx$1.5 mm) was performed above primary motor cortex (M1). Tungsten microelectrodes were then lowered (0.3 to 0.8 mm) into the apical dendritic field of M1 layer 5 pyramidal neurons (FIG. 23). Tungsten microelectrodes were connected to a Medusa PreAmp (RA16PA; Tucker-Davis Technologies, Alachua, Fla., USA) and a multichannel neurophysiology workstation (Tucker-Davis Technologies) consisting of a RX5 Pentusa multiprocessor base station to acquire of extracellular activity. Raw extracellular activity was acquired at a sampling frequency of 24.414 kHz. The MUA signal was filtered between 0.3 to 6 kHz while the LFP signal was filtered between 1 and 120 Hz with both signals being re-sampled at 1.017 kHz. Transcranial US waveforms were subsequently delivered to the ipsilateral M1 recording location by positioning the lateral edge of focusing guide-coupled transducers <1 mm caudal to the cranial window. To facilitate off-line analyses, TTL signal markers indicated the onset of ultrasound stimulus waveforms. At the end of experiments, electrolytic lesions were made to confirm recording sites in histological evaluations (FIG. 23). FIG. 23A shows a spike raster plot illustrates an increase in cortical spikes as a function of time in response to US stimulation, while FIG. 23 B shows raw (black) and average LFP (grey) traces recorded in response to US stimulation are illustrated (top). FIG. 23C shows the average EMG integral recorded from the left triceps brachii in response to transcranial US stimulation of right motor cortex is illustrated (bottom). FIG. 23D shows a post-stimulus time histogram (50 msec bins) illustrates the average MUA spike count recorded 500 msec prior to and 500 msec following the delivery of US stimulus waveforms to motor cortex.

In those experiments utilizing EMG recordings, fine-wire EMG recordings were made using standard approaches and a four-channel differential AC amplifier (model 1700, A-M Systems, Inc., Sequim, Wash., USA) with 10-1000 Hz band-pass filter and a 100× gain applied. Electrical interference was rejected using a 60 Hz notch filter. EMG signals were acquired at 2 kHz using a Digidata 1440A and pClamp. To facilitate off-line analyses, TTL signal markers indicated the onset of US stimulus waveforms. Small barbs were made in a 2 mm uncoated end of teflon coated steel wire (California Fine Wire, Co., Grover Beach, Calif., USA). Single recording wires were then inserted into the appropriate muscles using a 30 gauge hypodermic syringe before being connected to the amplifier. Ground wires were similarly constructed and subcutaneously inserted into the dorsal surface of the neck.

All electrophysiological data (MUA, LFP, and EMG) were processed and analyzed using custom-written routines in Matlab (The Mathworks, Natick, Mass., USA) or Clampfit (Molecular Devices). Ultrasound waveform characteristics were analyzed using hydrophone voltage traces and custom written routines in Matlab and Origin (OriginLab Corp., Northampton, Mass., USA). All histological confocal images were processed using ImageJ (http://rsb.info.nih.gov/ij/). Electron microscopy data were quantified using ImageJ and methods similar to those previously described. Immunohistochemical data were analyzed using previously described methods. All statistical analyses were performed using SPSS (SPSS, Inc., Chicago, Ill., USA). Data shown are mean±S.E.M unless indicated otherwise.

The Examples described herein demonstrate that ultrasound stimulus waveforms stimulate neuronal activity in both in vitro and in vivo constructs. Generally, stimulus waveforms constructed using ultrasound pulses having a high PII ($\approx$4.0 J/cm$^2$) repeated at slower PRFs ($\approx$50 Hz) for longer durations ($\approx$5 sec) effectively modulated neuronal activity in vitro (e.g., hippocampal slice culture). Generally, stimulus waveforms constructed using ultrasound pulses having a low PII (<0.1 mJ/cm$^2$) repeated at high PRFs (1.0-3.0 KHz) for short durations (<0.4 sec) effectively modulated neuronal activity in vivo (e.g., intact brain).

It is to be understood that the disclosed compounds, compositions, articles, devices, and/or methods are not limited to specific methods or devices unless otherwise specified, or to particular reagents unless otherwise specified, as such may, of course, vary. It is also to be understood that the terminology used herein is for the purpose of describing particular embodiments only and is not intended to be limiting.

In the description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

The invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense.

What is claimed is:

1. A method for modulating neuronal cellular activity of a neuronal cellular site in a subject, comprising:
    acoustically coupling at least one component for generating ultrasound waves to an external surface of the subject to stimulate the subject's vagus nerve or pancreas, and
    driving the at least one component for generating ultrasound waves to form at least one stimulus waveform at the subject's vagus nerve or pancreas, the stimulus waveform comprising a plurality of pulses, each pulse of the plurality comprising a plurality of acoustic cycles having one or more frequencies in a range from about 0.02 to about 100 MHz at the site of the cells to be modulated, wherein said each pulse of the plurality comprises a plurality of frequencies and wherein pulses of the plurality are repeated to produce spatial-peak temporal-average intensities of no more than 100 W/cm2.

2. The method of claim 1, wherein the method is a method of treating diabetes.

3. The method of claim 1, wherein the stimulus waveform is administered in a focused manner.

4. The method of claim 1, wherein driving comprises triggering the (β-cells of pancreatic islets to increase one or more of insulin synthesis and insulin secretion.

5. The method of claim 1, wherein the stimulus waveform is administered in a continuous wave or pulsed manner.

6. The method of claim 1, wherein the stimulus waveform is administered in a pulsed manner ranging from every 0.000001 seconds to 1,000,000 seconds during the delivery of any one ultrasound transmission event.

7. The method of claim 1, wherein the treatment regime is repeated.

8. The method of claim 1, wherein the acoustic frequency is delivered to the subject in a single or combination of acoustic frequencies ranging from 0.05 to 50 MHz.

9. The method of claim 1, wherein the at least one component for generating ultrasound waves is composed of 1 to 1000 ultrasound transducer elements.

10. The method of claim 9, wherein the ultrasound transducer elements are driven using analog or digitized such that the stimulus waveforms contain one or multiple ultrasound frequencies.

11. The method of claim 10, wherein the ultrasound transducer elements are composed singly or in a combination of square, sine, saw-tooth, or arbitrary waveforms.

12. The method of claim 1, wherein the ultrasound treatment is given to the subject in combination with another treatment regime for treating diabetes.

13. The method of claim 12, wherein the ultrasound stimulus waveform is given to the subject in combination with other therapies, including recombinant proteins or small organic molecules.

14. A method for modulating cellular activity in treating a subject with diabetes, comprising, providing ultrasound treatment comprising:
   acoustically coupling at least one component for generating ultrasound waves to the subject to stimulate the subject's vagus nerve, and
   driving at least one component for generating ultrasound waves to form at least one ultrasound stimulus waveform, wherein the stimulus waveform comprises one or more frequencies, with an intensity in a range from about 0.0001 to about 900 mW/cm2 at the site of the cells to be modulated.

15. The method of claim 14, wherein driving comprises triggering the (β-cells of pancreatic islets to increase one or more of insulin synthesis and insulin secretion.

16. The method of claim 14, wherein the stimulus waveform is administered in a focused manner.

17. The method of claim 14, wherein the stimulus waveform is administered in a continuous wave or pulsed manner.

18. The method of claim 14, wherein the stimulus waveform is administered in a pulsed manner ranging from every 0.000001 seconds to 1,000,000 seconds during the delivery of any one ultrasound transmission event.

19. The method of claim 14, wherein the acoustic frequency is delivered to the subject in a single or combination of acoustic frequencies ranging from 0.05 to 50 MHz.

20. The method of claim 14, wherein the ultrasound treatment is given to the subject in combination with another treatment regime for treating diabetes.

* * * * *